United States Patent [19]

Quintero et al.

[11] Patent Number: 5,293,479
[45] Date of Patent: Mar. 8, 1994

[54] DESIGN TOOL AND METHOD FOR PREPARING PARAMETRIC ASSEMBLIES

[75] Inventors: Stephen Quintero; Jim Smith, both of Los Angeles, Calif.

[73] Assignee: Quintero Smith Incorporated, Los Angeles, Calif.

[21] Appl. No.: 871,310

[22] Filed: Apr. 20, 1992

Related U.S. Application Data

[63] Continuation-in-part of Ser. No. 727,819, Jul. 8, 1991, abandoned.

[51] Int. Cl.$^5$ .......................... G06F 15/60; G06F 3/00
[52] U.S. Cl. ..................................... 395/161; 395/921; 395/919; 364/512
[58] Field of Search ............... 395/155, 161, 120, 156, 395/160, 75, 77, 921, 919, 923; 364/512, 474.24

[56] References Cited

U.S. PATENT DOCUMENTS

| | | | |
|---|---|---|---|
| 4,275,449 | 6/1981 | Aish | 364/512 |
| 4,642,780 | 2/1987 | Thomson | 364/512 |
| 4,651,284 | 3/1987 | Watanabe et al. | 364/491 |
| 4,700,317 | 10/1987 | Watanabe et al. | 364/488 |
| 4,813,013 | 3/1989 | Dunn | 364/900 |
| 4,831,546 | 5/1989 | Mitsuta et al. | 364/512 |
| 4,835,709 | 5/1989 | Tsai | 395/921 X |
| 4,868,766 | 9/1989 | Oosterholt | 364/522 |
| 4,870,591 | 9/1989 | Cicciarelli et al. | 395/921 X |
| 4,875,162 | 10/1989 | Ferriter et al. | 364/401 |
| 4,916,634 | 4/1990 | Collins et al. | 364/513 |
| 4,926,344 | 5/1990 | Collins et al. | 364/513 |
| 4,928,221 | 5/1990 | Belkhiter | 364/191 |
| 4,928,233 | 5/1990 | Millis | 364/522 |
| 4,939,668 | 7/1990 | Brown et al. | 364/513 |
| 4,943,932 | 7/1990 | Lark et al. | 364/513 |
| 4,947,322 | 8/1990 | Tenma et al. | 364/401 |
| 4,964,060 | 10/1990 | Hartsog | 364/512 |
| 5,038,294 | 8/1991 | Arakawa et al. | 395/921 X |

OTHER PUBLICATIONS

Coates, D., "Daemonic CAD: The Practical Implementation of AI," Cadence, Feb. 1991, pp. 40–44.

Primary Examiner—Heather R. Herndon
Assistant Examiner—Raymond J. Bayerl
Attorney, Agent, or Firm—David J. Larwood

[57] ABSTRACT

An expert system is described for use in designing a connected collection of components which are available or can be made in different forms, e.g. which can be described by a selected number of variables. The expert system includes a knowledge base and an inference engine. The knowledge base includes records pertaining to constant and variable characteristics of connectable components and rules for combining a component with other components. The inference engine allows selecting a record for a first component, then a record for only those second components which can be connected to the first component, and storing information about the connections.

24 Claims, 31 Drawing Sheets

7-1-1991   14:25:56
Project:   HAVEFUN
           testing, testing, testing
Product List: PATENT

| Item | | Description | Qty | PQty | $UList | $XList | $Xdealer | $Xcustomer |
|---|---|---|---|---|---|---|---|---|
| 1 | E1110.7048L | Frame, Power 4 Circ Shielded 70H 48W<br>NN None<br>BUS Black Umber | 2 | 2 | 441.00 | 882.00 | 441.00 | 565.38 |
| 2 | E1260.48W | Top Cap, Frame-Wood 48W<br>RK Mahogany Dark Recut Veneer | 2 | 2 | 96.00 | 192.00 | 96.00 | 123.08 |
| 3 | E1420.1648W | Tile, Face Recut Veneer 16H 48W<br>RK Mahogany Dark Recut Veneer | 4 | 4 | 117.00 | 468.00 | 234.00 | 300.00 |
| 4 | E1421.1648 | Tile, Acoust 16H 482<br>32 Iota 01 Bramble | 4 | 4 | 97.00 | 388.00 | 194.00 | 248.72 |
| 5 | E2310.3048W | Work Surf, Rect B/Nose Wood/Wood 300 48W<br>RK Mahogany Dark Recut Veneer<br>BUS Black Umber | 1 | 1 | 473.00 | 473.00 | 236.50 | 303.21 |
| 6 | E3110.48WK | Storage Cab, Veneer 48W<br>BUS Black Umber<br>RK Mahogany Dark Recut Veneer | 1 | 1 | 461.00 | 461.00 | 230.50 | 295.51 |
| 7 | E4401.1830A | Support Cabinet Top, Oversall Back/Side/F<br>RK Mahogany Dark Recut Veneer | 1 | 1 | 229.00 | 229.00 | 114.50 | 146.79 |
| 8 | E4410.7030W | Work Cabinet, Veneer Door 70H 30W<br>BUS Black Umber<br>RK Mahogany Dark Recut Veneer<br>BUS Black Umber | 1 | 1 | 2319.00 | 2319.00 | 1159.50 | 1486.54 |
| 9 | G5010. | Pencil Drawer 2H 21W 16D<br>BUS Black Umber | 1 | 1 | 33.00 | 33.00 | 16.50 | 21.15 |
| 10 | G5142.190AK | Ped, D-Frt Suspended 6,6,6 Veneer 20H 15W<br>RK Mahogany Dark Recut Veneer | 1 | 1 | 593.00 | 593.00 | 296.50 | 380.13 |
| 11 | G6110.48 | Task Light, General 48W<br>BUS Black Umber | 1 | 1 | 183.00 | 183.00 | 91.50 | 117.31 |

Total List Price:    $ 6221.00
Total Dealer Cost:   $ 3110.50
Total Customer Cost: $ 3987.82
Total Margin:        %   22.0000

WARNING CLUSTER(S) IN SET FAILED DRC

FIGURE 2

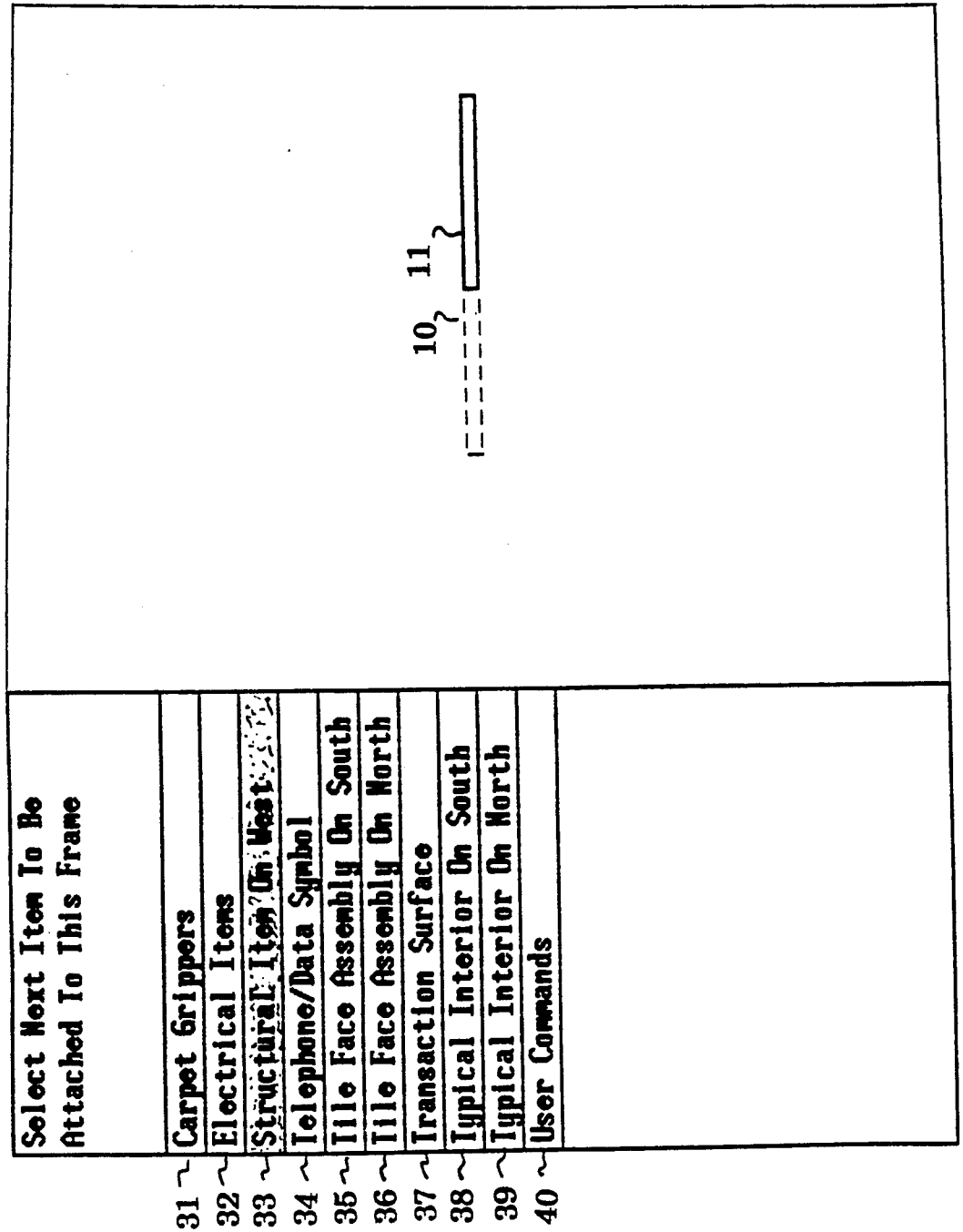

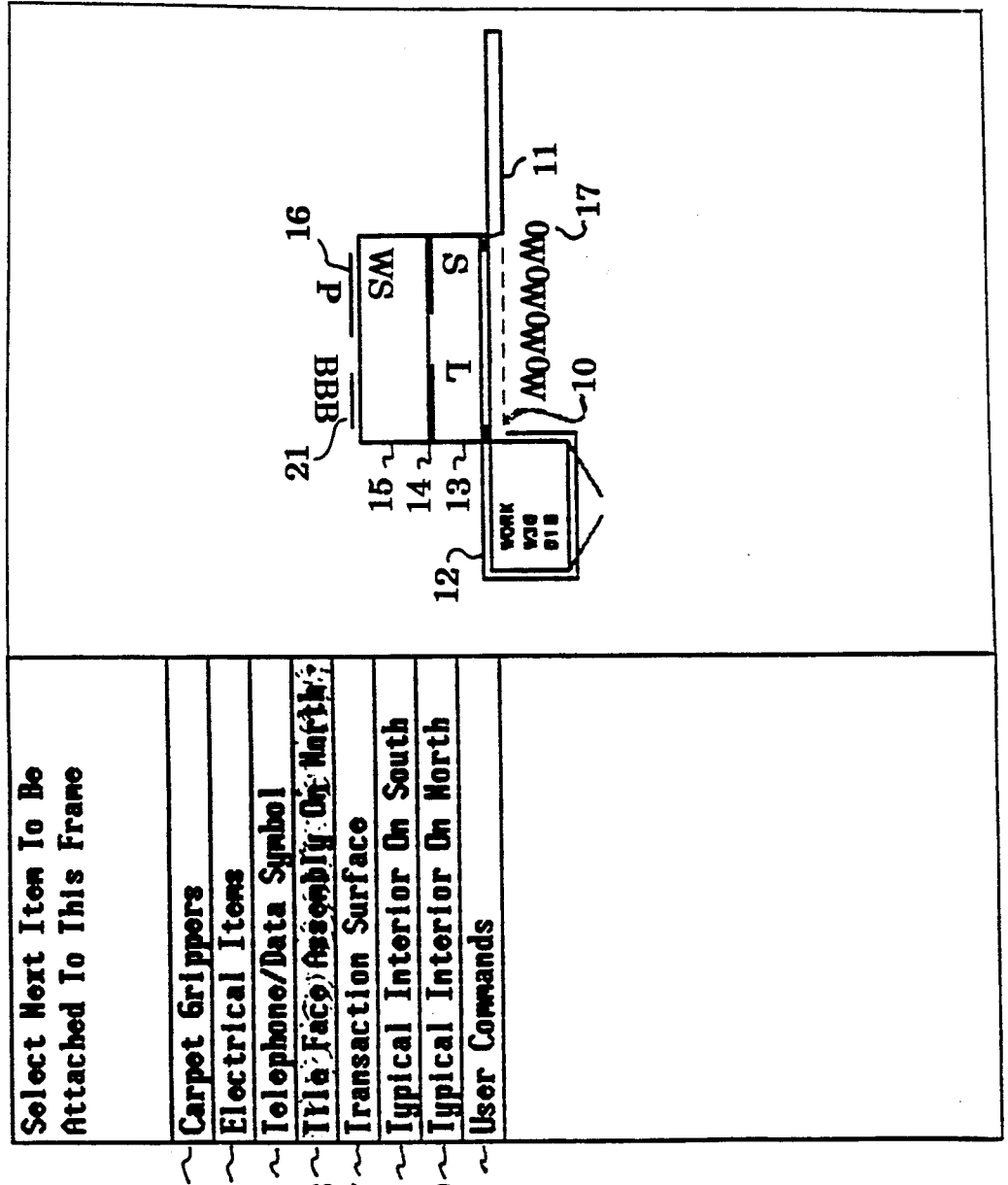

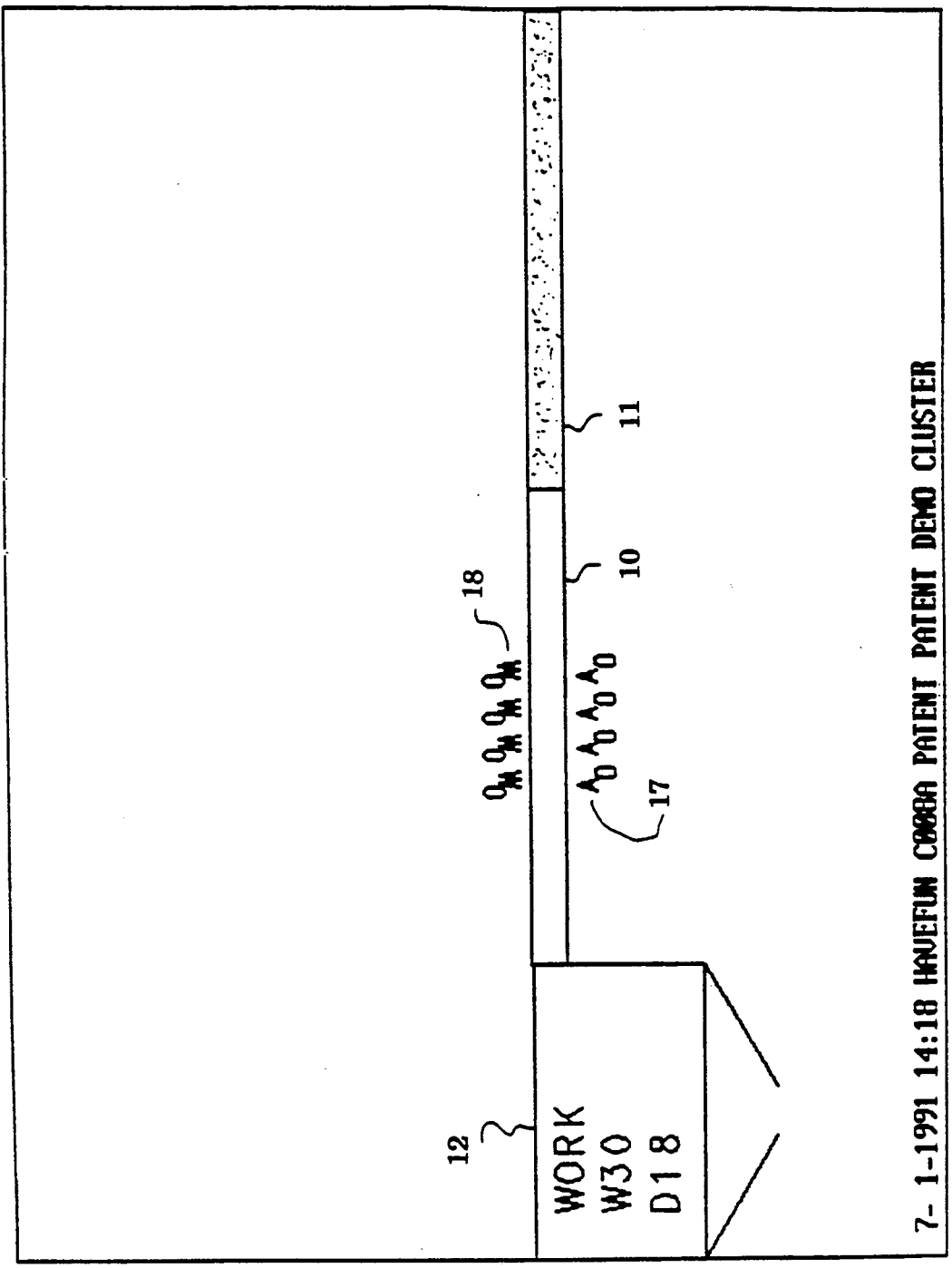

| Initially, All Frames In This Cluster Are |
|---|
| 38" |
| 54" |
| 70" |
| 86" |
| Do Not Auto Select |

Local Default Variable Set

| Width Of This Frame |
|---|
| 24" |
| 30" |
| 36" |
| 42" |
| 48" |

FIGURE 14

| Structural Item Options | |
|---|---|
| Frame | |
| 2-Way Connector | |
| 3-Way Connector | |
| 4-Way Connector | |
| Finished End | |
| Power Entry, Ceiling | |
| Spacer | |
| Support Cabinet | |
| Wall Start | |

Select Tile Face Assembly
Height: 70
Width: 48

AA AA AA AA AA
CB GB NB AA
HB GB DB AA
WB WB WB WB
Make New Tile Assembly
No Selection List of legal Tile Typicals
derived from CIT Database

WORK
VCA
B10
010

FIGURE 24

DESIGN TOOL AND METHOD FOR PREPARING PARAMETRIC ASSEMBLIES

This application is a continuation in part of U.S. patent application Ser. No. 07/727,819 filed Jul. 8, 1991, now abandoned.

I. FIELD OF THE INVENTION

This invention relates to a design tool and process for selecting and organizing interconnectable components and for designing, describing, displaying and manufacturing products having a number of variable characteristics. In particular, this invention is useful for specifying and designing assemblies of modular furniture components and perfusion kits and for manufacturing wire harness assemblies, propellers, bolts and other fasteners.

II. BACKGROUND OF THE INVENTION

Many industries are faced with the problem of assembling diverse components into final products which generally are different for each customer or application. For example, in the office furniture business, several manufacturers, including Herman Miller, Steelcase and Westinghouse, offer lines of components which can be interconnected to assemble modules with partitions, writing surfaces, storage, lights, etc., in a nearly infinite variety of different configurations. In some office environments, different modules are assembled to provide work rooms, secretarial stations and offices for all levels of employees.

Another industry facing similar problems is the manufacture of perfusion kits. A perfusion kit is used by doctors during surgery to handle blood outside of the patient's body. A perfusion kit may include an assembly of any of a number of tubes, branch points, valves, needles, injection ports and monitoring options.

A persistent problem in designing and assembling collections of diverse components is the need to keep track of a large number of small components. For example, a typical modular secretarial station might consist of several wall units, multiple filing units, a typewriter surface, a desk, power inputs, lighting, plus numerous fasteners and plates which vary depending whether the module is free standing, adjacent to another module, or between two or more other modules. If a facility has 25 secretarial stations which are essentially identical but have some variations, the number of individual components can be very large. In order to keep track of all of these parts, the industry has developed specifiers or computer programs that facilitate counting how many of each type of component are needed. Some manufacturers distribute current pricing and other information periodically in a computer readable format, which can be read into a specifier to generate a purchase order.

The designer must order enough parts to assemble the modules, the manufacturer or distributor must ship enough parts and the assembly crew must be able to locate the parts to assemble each module. In practice, even with the assistance of a specifier it is difficult to keep track of the large number of discrete parts and industry practice is to order excess basic components, such as fasteners, to be sure enough are on hand to do the final assembly. This is wasteful of resources and adds to the cost of each assembly.

Others have used expert systems for layout and design (see Watanabe et al., U.S. Pat. Nos. 4,651,284 and 4,700,317; Hartsog, U.S. Pat. No. 4,964,060) or have sought to develop improved modelling or space planning methods (see Thomson, U.S. Pat. No. 4,642,780; Aish, U.S. Pat. No. 4,275,449). None of these references teach the present device or method or have been able to produce or manipulate the sophisticated and easily editable assemblies of the present device and method.

III. SUMMARY OF THE INVENTION

The present system and method provides a design tool for designing an assembly which is a combination of components, each of which can be described by a selected number of variables and which may be available or may be made in different forms. The design tool includes a rule base, a knowledge base and an inference engine. The knowledge base includes a plurality of records pertaining to types of connectable components, where there is a record containing characteristics for a connectable component and rules as needed to define combining the component with other connectable components. The inference engine includes means for selecting a record for a first component, means for selecting a record for another component to be connected to the first component, and means for storing information about a plurality of connected components to form an assembly.

The design tool makes use of constant and variable characteristics to define and manipulate components and assemblies. Constant characteristics include component name, component description, manufacturer identification number, price information, availability information, dimensions, color or texture. Variable characteristics of an assembly may include information about whether more than one component has been selected and, if so, information about a second component and how and where the second component is connected to a first component.

One object of the present invention is to provide a convenient system and method for selecting interconnectable components and designing assemblies of the components where only allowed connections can be selected and a corresponding physical assembly can actually be constructed.

Another object of this invention is to provide a system for inventory and ordering control.

IV. BRIEF DESCRIPTION OF THE DRAWINGS

FIGS. 1A, 1B, 1C and 1D, respectively, illustrate four different views of an assembly with three frames, a work cabinet on one side and a workstation, with desk, light, shelf and drawers on the other side.

FIG. 2 illustrates a product list for the assembly in FIG. 1.

FIG. 3 illustrates a screen display with menu choices which can be selected for the displayed Active Component in an assembly.

FIG. 4 illustrates another screen display with menu choices which can be selected for the displayed Active Component in an assembly.

FIG. 7 illustrates a screen displayed after DRC, showing items which failed a completeness check.

FIGS. 9-29 illustrate screen displays for a design process.

V. DETAILED DESCRIPTION

A. Overview

Figure 1A:
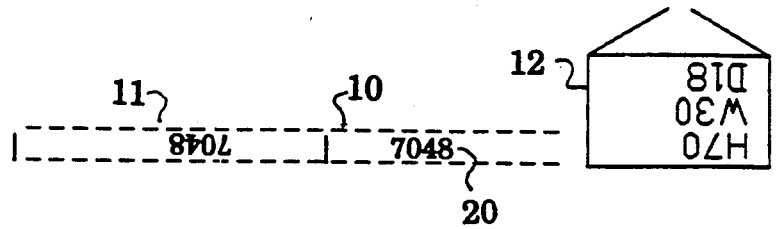

The present invention may be utilized with a variety of different systems. A system is a functionally related group of elements or components or an object describable by a bounded group of parameters. The present invention is capable of organizing and interrelating components of a system according to the characteristics of the components and predetermined rules. The components of a system are used by the design tool of the present invention to form a design. This design is described by a design database.

The basic criteria which make a particular system well suited to present invention, are: 1) the components of the system can be combined in many different ways; and 2) a limited amount of information can describe a combination of the components of the system.

For example, systems which are well suited to the design tool include but are not limited to:

a. Systems Furniture. This is furniture which exists in large numbers of components which are assembled according to customers' designs. A system may consist of several hundred to several thousand different components which fit with other components of the system. Several manufacturers manufacture one or more systems some of which include components which may be used interchangeably between systems.
b. Perfusion Kits. These are assemblies of standard and variable components made and assembled on a custom basis according to physicians' designs. They may be used to handle extracorporeal blood during surgery.
c. Other Assemblies: wire harness assemblies; HVAC; plumbing telephone cable routing; motors.
d. Impellers and Propellers. These generally are single component designs which are generated from a system whose elements are materials and geometric constraints.
e. Other Single Component Designs: fasteners; bolts.

For purposes of illustration, this document will deal with the systems furniture application of the design tool. Compass directions assume north is up, east is right, etc.

The following description is set forth in sections. The first section contains definitions of terms frequently used in connection with the description of the invention. The second section deals with the structure of the design tool as a framework for use in different applications with reference to the currently preferred embodiment of the furniture systems. The third section discusses customization of the design tool for specific applications, e.g., for a specific manufacturer's line of systems furniture. This process is typically implemented under the direction of a programmer and an experienced designer. The fourth section describes the system specific features of the present invention in greater detail and the last section deals with examples operation of the present preferred embodiment. This process is typically carried out by everyday users, who need have little experience yet can design functional assemblies.

B. Definitions

A number of basic definitions are set out in this section which may assist the understanding and explanation of the present invention. The following explanatory discussion is not meant as a complete glossary, since many terms are introduced elsewhere, in the logical flow of the description.

In a systems furniture application of the present invention, the system is a collection of different furniture items, such as wall-units, shelves, connectors for same, etc. These furniture items are components within the system made by a manufacturer. Components are designed to fit together interchangeably, for example, a shelf may be available in a predetermined number of widths (e.g. 24", 36" and 48") which are the only widths available for shelf supports (frame, tile, etc.).

One of the basic components of a furniture system is a frame, a generally rectangular structural component. A frame can support various components such as storage cabinets or work surfaces. Referring to FIG. 1, a number of components are illustrated. Frame 10 is attached to empty frame 11 and wall cabinet 12. Frame 10 has been completed by adding attachable components storage cabinet 13, light 14, work surface 15, pencil drawer 16, and suspended drawers 21. The remaining open spaces on each side of frame 10 are filled, in this example, with a full set of tile faces, four acoustic tile faces 17 and four mahogany wood tile faces 18. FIGS. 1A, 1B, 1C and 1D represent views of the same assembly.

A component can be described in terms of its attributes, preferably defined by one or more constant characteristics generally sufficient to describe the component. A constant characteristic is constant for a specific component but variable between components and might include color, height, width, depth, texture, powered, non-powered, and other characteristics needed to describe the component and distinguish it from other components in the furniture system. Other useful constant characteristics may be associated with a component such as a description of the component suitable for use with a CAD display program (e.g., a to library file for AutoCAD ®). Still other useful constant characteristics may define points on the component at which other components can be connected. The constant characteristics of individual components may be stored as variables in one or more constant databases such as the part database, geometry database and option database described below in Example 1.

Some components are primitive components which are unitary components, not divisible into other components. Some components are custom components which may be defined and recorded in a design database or incorporated into records similar to the records for individual components. Once defined, these custom components function just like other individual components or primitive components.

An assembly is a collection of one or more linked components. The design tool allows linking components in essentially any configuration which is possible with the actual, physical components. Each assembly is represented by a design database which will be described in detail below. An assembly may include not only individual components but also other assemblies, sometimes referred to as "sub-assemblies" or included assemblies.

The design database contains individual records for each component of the assembly. Each record references information which describes the component, e.g., a record in the part database for that component. A design database for an assembly can include entries for essentially any combination of components and assemblies. A design database entry for a component references pertinent information about that component in one or more constant databases. A design database entry for an included assembly references another design database, one for the included assembly.

In one application of the design tool, the final product is a single component but the design tool is used to select materials and geometric features, e.g., the pitch of threads on a bolt. In such a system, an assembly is a collection of parameters or other constant characteristics. Other examples of a single component system are manufacturing of impellers and propellers which have variable structural characteristics and materials as system components.

The design tool can accommodate certain special assemblies such as a "Tile Typical" or an "Interior Typical." These special assemblies consist of a group of components fixed in space relative to each other but without a specific position or orientation in absolute space. In general, these components do not need to be, and are not, connected to each other. These special assemblies can be connected during the design process to another component or assembly to complete certain design needs.

A Tile Typical is a characteristic choice and arrangement of tiles for use on the surface of a frame. One or more tile Typicals can be preselected to accommodate the design goals for a project. Referring to FIGS. 1B and 1D, tile descriptor 17 refers to a Tile Typical consisting of four acoustic tiles, 48 inches wide. Information on the specific part numbers, dimensions, etc. is available. In FIG. 1D, the tiles are shown in a three-dimensional projection, largely hidden by the tiles of Tile Typical 18. Tile Typical 18 consists of four wood tiles, also 48 inches wide. Tile Typical 17 has been selected for the "north" side of frame 10 and Tile Typical 18 has been selected for the "south" side of frame 10. A menu selection of predefined Tile Typicals is illustrated in FIG. 24.

An Interior Typical is a special assembly of interior components. An Interior Typical might consist of a series of work surfaces, drawers, cabinets, etc., for use in a typical work area for an employee cubicle. Another Interior Typical might be the interior for an executive module with a high grade of finishes, certain storage or light facilities, or other components selected by the system designer.

Since assemblies can be used in other assemblies, each time an assembly is changed, that change can be marked, e.g., with a flag, so the design tool knows to check all marked included assemblies to determine the impact of any changes. If a change in an included assembly renders the existence of the including assembly logically impossible, the included assembly is deleted from the design database for the including assembly. For example, a change to an included assembly may result in that assembly being too large for the available volume in the including assembly in which it is installed.

A cluster is another special assembly, one that is "complete" or one which has no open connection point which must be connected to another assembly or individual component. For example, a component such as a frame should be filled on essentially all faces and edges, by, for example, a complete set of tiles or other components plus a top cap and either a connector to one or more other frames, or an edge cap. It may be possible to add additional components, e.g. one or more shelves to a frame in a cluster, but no component in a cluster needs to be connected to any additional component to be complete.

One or more clusters can be placed in space to complete a design. For example, a complete design may have one cluster designed as a secretarial work group, another cluster designed as an engineer work group, and a third cluster designed as an executive work group. A complete design might consist of a certain number of secretarial clusters, a number of engineering clusters and a number of executive clusters. The complete design could be the sum collection of each of these clusters.

Another feature of the design tool is a "space plan." In a preferred implementation, the space plan begins with an outline of the available space, for example, a blueprint of the building shell. Clusters or other assemblies can be placed within the building shell in a non-contiguous manner. For example, one suitable assembly can be a mere outline of a cluster without completing the entire cluster. A user may represent a large design schematically without finalizing details until overall design criteria have been satisfied.

Clusters can be placed within a "building shell" in a non-contiguous manner to form a "space plan," which encompasses the entire design. Building shells are volumes defined by the system. Accordingly, a design database for a space plan assembly may reference design databases for one or more cluster assemblies or free standing components used in the space plan. Cluster assemblies may reference one or more Tile Typical or Interior Typical assemblies. Throughout this description where the use of an individual component is contemplated, a primitive component, custom component, or assembly may be used interchangeably depending on the physical constraints of the system.

The design tool for a given system is fully determined, which is to say that preferably all legal assemblies can be designed and no illegal assemblies can be designed. In actual practice, it is sufficient to design most legal assemblies and almost no illegal assemblies.

A design is all the furniture in one project and how it is combined. A project is the user's requirement of systems furniture for a specific application. For example, a customer may commission a vendor to complete a project which consists of furnishing an office. As a part of this project, the vendor will use the design tool to arrive at a furniture design.

The concept of variables as used in the present invention is important to the design process. For example, variables define the status of an assembly during the design process. The status of a component is the combination of constant and variable characteristics which are relevant to the design tool at the time the design tool is performing an operation which modifies or checks the current configuration of a component. For a preferred embodiment of the systems furniture application, the software maintains the values of some three hundred different variables in the form of unsigned short integers. These variables govern the actions of the design tool. A selected subset of these variables is saved with each record in the design database and describes the variable characteristics of the logical condition of the component which corresponds to that record. The number of variables required depends to a large extent on how many types of components are available from the manufacturer, how they fit together, which combinations are and are not allowed, etc.

C. Structure of the Design Tool

As described below, the design tool consists of several parts, including a knowledge base, a rule base, an inference engine, an expert user interface and a graphic system. These parts of the design tool are integrated with information regarding the specific characteristics of the components of the furniture system and how they interrelate so that the design tool will be capable of creating a design for the particular furniture system.

Other parts of the design tool which will be discussed in this section include the documentation control and automated output control. This section will describe the general structure and functional interrelationship of the parts of the design tool.

1. Knowledge Base.

The knowledge base is a set of databases containing information pertaining to components within the system which are the subject of the design tool application. Generally, this information consists of the constant characteristics for each component. As discussed above, constant characteristics for a component which may be stored in the knowledge base include connection vectors, graphical information such as drawings of the component, assembly instructions and availability. Connection vectors are represented by vector variables which correspond to potential connection points for a component and whose corresponding values as stores in design databases describe the current geometry of the connections for that component.

The knowledge base is a basic component of the design tool, although the specific databases required to describe and manipulate a given system may vary with the application. The following discussion and examples describe a series of databases useful for the preferred implementation of the design tool for the systems furniture. One skilled in the art can select and create appropriate databases for a variety of applications that come within the teachings and claims of this invention.

The information to be entered in the knowledge base depends on the particular system modelled in the design tool. This information might come from a manufacturer's catalog or from other sources. In general, this information should be entered and checked carefully. This entry typically is done by or under the supervision of an experienced programmer.

2. Rule Base.

The rule base contains rules for what components can be combined with other components and under what conditions they can be combined plus what components must be present under certain conditions. Rules are used in the design process to allow proper combinations of components and disallow improper combinations. These rules are preferably based on characteristics of each component which depend, in turn, on the system in use, e.g., a certain frame or type of frame can be connected to a certain type of connector or a certain type of tile. The rules should accommodate different states of a component, for example, a combination of the first component with a second component may be allowed for the first component alone but a subsequent combination with a third component may be affected by the fact and nature of the combination of the second component with the first.

In the preferred embodiment of the present invention the rule base consists of two parts: (1) a menu database which includes rules for menu selections and (2) global rules. The menu database contains rules which define whether and how a component can be connected to another component. The rules included tests for various conditions, e.g., the presence or availability of certain types of connections or components. The rules also control the display of menu options, preferably showing only options which are possible at a given stage of the design process and not showing or otherwise indicating choices which are not possible at that stage. Preferably, the present invention is menu driven. That is, during the design process the user makes selections from a list of displayed selections. These rules operate to constrain the design process by limiting the selections available depending upon the component upon which another component is to be added.

Some rules govern the selection of defaults by a user. Before beginning the design process the user may select certain options which will either limit subsequent menu selections or cause selections to be made automatically.

Global rules govern the interaction of components which are not necessarily directly linked to one another. Global rules might not be useable during the design process to determine what components may be combined with other components and how the components can be combined. That is, the combinability or state of a component may change dependent upon the addition of other components in such a way that the change cannot be detected during menu traversal. During menu traversal the rules are dependent upon the known information for a component to which another component is being connected. Thus, there is limited access to or use of information during menu traversal during the design process regarding other components which may impact the combination of two directly linked components.

3. Inference Engine.

The inference engine selects and applies rules from the rule base using information from the knowledge base to direct and implement the design process. The inference engine passes information from the design database to the graphic system, described below, to display selected information from the knowledge base according to the rules in the rule base. During the design process the inference engine accepts input including user choices through menu selection and input based on application of rules.

The inference engine calls the design rule check (DRC) when a design is saved. The design rule check applies the global rules to the complete design database to detect errors in design. In the preferred embodiment, the design rule check checks local design rules which are for the most part taken care of by the design process. The global design rules test for design completeness and for proper interaction of components and not just the characteristics of individual components. Example 6 below further describes the design rule check in connection with its operation.

4. Expert User Interface.

The expert user interface includes a series of menus, presented to the user by the inference engine in accordance with the rules and conditions in effect at the time. The expert user interface is applicable to many parts of the design tool and minimizes the program user's steps required to control the design process.

The expert user interface is responsive to user commands to control program operation and cause the creation of a design. The expert user interface directs the creation of the design by means which will be described more fully below through examples but which employ the knowledge base, rule base and inference engine.

The user may select a component by a user mouse digitization (mouse button press at a screen location) which makes the selected component active. The design tool permits components to be randomly accessed or selected from within the design when selecting a component.

The expert user interface minimizes the required input into the design process by the user by only allowing the user to select viable menu selections during the design process and by outputting meaningful messages as a result of the design rule check. Additionally, the expert user interface will make selections for the user whenever possible. For example, if certain default conditions have been established (typically stored in a default database) then whenever the interface can make a decision based on default information, it will do so. If a user preselects a default that all new frames will be powered and have a certain height, then whenever the user would have been presented with the option of selecting powered or not, the interface will automatically make the selection of powered. Similarly, when the user would have been presented with the option of selecting frame height, the interface will assign the frame height based on the default values. These defaults can be applied to many types of components without preconfiguring each component type.

As another example, if the height of an attached component is required to be a certain value in order to be attached, the expert user interface will make the height selection without consulting the user. As another example, if a group of frames has the correct configuration to connect to the components of an Interior Typical, the expert user interface and the inference engine will effectively make all required connections automatically.

5. Graphic System.

The graphic system produces graphic representations of the design or portions of the design during the operation of the design tool. The graphic system can display images of components, assemblies and designs by referring to the design database and knowledge base. The graphic representations of the current design are updated and displayed as the design is changed.

The graphic system includes tools which allow the user to make basic display modifications such as zooms, pans, windowing, and graphic displays of different information about the design. Graphics are produced automatically based on information in the databases; the user never manipulates the graphics directly but the graphics visually "echo" the design database. METAGRAPHICS version 3.8A now version 3.7C used) was used to provide the graphics environment (primitive graphics functions) under DOS.

Figure 1B:
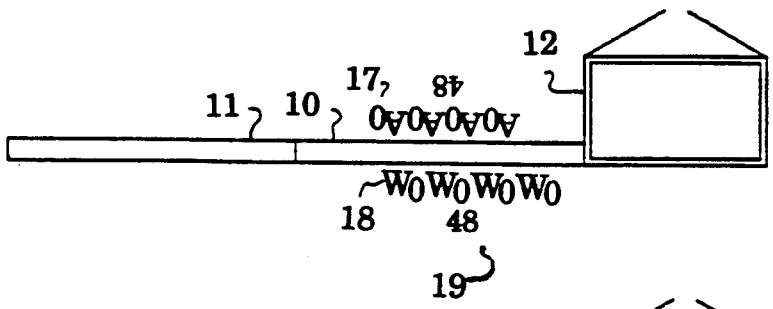

The graphic system also can display part numbers, e.g., 20 in FIG. 1A, or information about components or surfaces. FIGS. 1B, 4 and 7 include readouts for Tile Typicals 17 (four acoustical tiles, in order, top to bottom along the frame) and 18 (four wood tiles).

6. Documentation Control.

These tools control the automatic filing and revision assignment of the design database for a design of the project. Filing and revision information is stored in the Project Database and in an assembly level database, i.e., the CIT database.

7. Automated Output Tools.

At various points in the design process, or external to the design process, the user may elect to automatically produce various forms of output. The design tool refers to the design database and knowledge base, which together completely define a design, to automatically create reports or representations of the design in other usable forms such as:

a. Bills of materials.
b. Inventory modification and order entry information.
c. Manufacturing and QA instructions.
d. Just-In-Time manufacturing process.
e. Plots, e.g. on paper media.
f. Quotations.
g. Assembly/Inspections times.
h. Shipping information (volume, weight, delivery schedule).
i. Manufacturing Resource Planning (M.R.P.)

Design information can be accessed in a usable form to create representations of the design in many other forms. These forms include the output listed above, as well as representations of the constraints under which the design was created (this could include, for example, a listing of the user selectable rules in place during design). The design database, or a set of design databases, can also be referenced for statistical analyses of their components.

One of the automated output tools interfaces with computer aided design software to produce two or three-dimensional representations according to a CAD image database. These CAD models can be wire-framed, surfaced or solid modeled. See FIGS. 1A-1D. Tool paths and/or post processed numerical control (NC) files used for the automated machining of parts may be produced from the CAD models automatically.

External to the design process, or within the process by way of constraining the possible generation or insertion of sub-assemblies, the design tool is ideally suited to the incorporation of group technology. Group technology can be used to assign certain values to database entries which are dependent on or reflect selected parameters within the database entry. That value can be used to quickly search for database entries that have selected parameters. In addition, group technology can be used to examine the design databases.

One useful platform for implementing this invention is INTEL-386-based computer running under MS-DOS 3.2 or higher. A color VGA monitor is useful, although an EGA monitor can be used. A hard disk is recommended, e.g. 40 MByte. Some implementations of a program using this invention may require more than 640K base RAM. PHAR LAP Software 386|DOS Extender can be used to avoid this limitation. The protected mode version of METAGRAPHICS (METAGRAPHICS PREMIUM, Version 3.8A), version 6.0 of C-TREE File Handler, and the Watcom C 8.0/386 compiler were used. One skilled in the art will recognize other platforms, compilers and software accessories that can be used successfully to implement the present invention.

Currently, RTLinkPlus made by Pocket Soft is used instead of the PHAR LAP DOS Extender. Further, the real mode of the METAGRAPHICS graphics software is used, as well as, version 4.3 of the C-TREE File Handler, and a MICROSOFT C compiler.

D. Customizing the Design Tool to Specific Applications

The design tool must be customized to operate with specific systems. Information specific to each system must be input into the various parts of the design tool for that particular system application. The type of information which must be integrated into the design tool includes design constraints and component information. As discussed above there are many systems to which the present invention may be applied. In a present preferred embodiment the design tool is applied to furniture systems.

Design constraints are generally those rules which govern the formation of designs. As discussed above in the definition section, rules are stored in the rule base. In the furniture systems application an exemplary type of rule governs connection of components or classes of components which have corresponding connection points which match in height and type of connector so adjacent components may be physically connected.

Some overlap exists between design constraints or rules and component characteristics in that the rules for a particular system are heavily dependent on component characteristics. Many rules relating to the compatibility of components to be linked refer to the dimensions of the respective component and, therefore, are a source of component characteristics.

Design constraints and component characteristics are generally entered by a programmer or designer of the particular application for the design tool since this information defines the design process and effectiveness of the expert user interface in facilitating the use of the system by individuals who are not designers for the particular system. Entry of the design constraints includes determining appropriate operational choices to be displayed in the menus of the design tool. Further the storage of the component information must be structured effectively to enhance the overall operation of the design tool.

Customization of the design tool to a particular system also involves structuring the graphic system and automated output tools. The graphic system is designed to enhance the visualization of the ongoing design process. The automated output tools are designed to produce outputs which are useful to the user.

E. Using the Design Tool

Using the design tool to produce a design database is an interactive process wherein the user is allowed to make legal designs, that is, physically constructable designs, and prevented from making illegal designs, all without requiring any specific technical knowledge of the software and generally without extensive knowledge of the components available in the system. This interactive process is menu driven and mouse controlled, with a menu on the left side of the screen and a graphic window on the right side.

The design process is menu driven in the sense that the expert user interface operates to furnish a number of possible operational choices in a menu which the user selects from. The menu lists available legal operations which may currently be performed on the design including components which may legally be added. The graphic window shows a graphic representation of the design in its current state. The user may use the mouse to make a menu selection or to select a component of the design represented in the graphic window. This process of mouse selection is often referred to as digitizing (or "diging") a menu selection or component.

Example 8 below illustrates the operation of the design tool in forming an assembly. The process of Example 8 is illustrated in connection with FIGS. 3, 4, and 9-29 which are screen dumps taken from the display screen during the design process. This example illustrates the physical operations that a user performs in implementing the processes described throughout the current application.

1. Summary of Operation a. Set Default Values

In a presently preferred embodiment of the invention, the user may set certain defaults, if desired, which will govern the general characteristics of the design, e.g., selection of materials or the height of a structural component such as a frame. For each variable which is not set to a default value, the user will have to enter the appropriate information for each component affected by that variable. Thus, use of defaults facilitates both consistent and rapid design of an assembly. The default information is stored in a default database.

Information in default databases allows automatic selection on some menus during the design process. They also set some basic conditions of the design environment. This information in the default databases can be modified by the user prior to or during the design process (through the user commands). In setting these default conditions the user is placed in the same expert menu environment used to govern the creation of design databases, generally without a graphic area. For the furniture systems application, the setting of user defaults is sufficiently complex to warrant such control to prevent conflicting or incomplete default conditions. Menu traversal while setting user defaults modifies the default databases rather than a design database.

b. The Design Process

Design begins by selecting and inserting a first component in the design. After the user selects the class of component, e.g., a frame, the design tool provides a series of menus from which the user can specify characteristics, e.g., height and width, powered or not, and color, necessary to select a unique component. Some of these characteristics may have been predetermined and stored in the default database so that they are autoselected.

An activatable component may be selected from a menu or from the currently active design by using a mouse to position the screen cursor over the component and clicking ("digitizing" or "diging") the component. Selection of an activatable component makes it the Active Component. The Active Component is highlighted and an active menu is displayed listing all of the operations which may be performed on or with the newly activated component.

Components are generally of two types: activatable or non-activatable. An activatable component can be made the Active Component while a non-activatable component can not. Typical non-activatable components are unique components which can be connected to only one other component and cannot be modified, e.g., frame caps, carpet grippers or socket cover plates. Typical activatable components can be connected to more than one other component and are modifiable, e.g., a frame which may connect to one or more other frames, to tiles, to top caps, to carpet grippers, to work surfaces, to cabinets, and to many other components.

The design tool provides for a hierarchy of components. In a preferred embodiment of the present invention, activatable components are generally classified in an hierarchy and non-activatable components are classified in a separate hierarchy. The hierarchy is a deletional hierarchy in the present invention. For example, when an activatable component is deleted all non-activatable components linked to that component are deleted because the non-activatable components are in a lower deletional hierarchy.

Where there are other types of components which share consistent design rules and relationship to other components, e.g., a deletional preference, these components may be grouped into a hierarchy of components. Thus, the hierarchical classification of activatable and non-activatable components is not meant to be restrictive.

When creating a new assembly, the first component is selected through initial menu traversal and placed in the assembly coordinate system by aligning the assembly coordinate axes with the component coordinate axes at both coordinate origins. See Examples 1 and 8, below. The design tool is used to design assemblies into building shells. Building shells are defined volumes into which an assembly must fit. Each assembly is assigned its own coordinate system. The coordinate system of the graphic area of the screen corresponds to the coordinate system of the assembly currently being designed.

The active menu for essentially each activatable component has a selection called "User Commands" which allows the user to access the user commands. In a space plan assembly this process is different in that all clusters are inserted from the user commands menu, while digitizing a cluster on screen opens the design database corresponding to that cluster assembly for modification and makes a component in the digitized cluster the Active Component. See Example 5 and FIG. 8 for a flow chart of the addition of a component to a design database.

Once the user selects a component or existing assembly to be added to the design, information about that component is entered in appropriate databases and the graphic display is updated to show the component. The menu is updated to show legal additions or changes to the component, plus some system options. The user continues by choosing and specifying additional components or assemblies, gradually building up an assembly.

Each component in an assembly of components is assigned a component number specific to that component with reference to that assembly. In a preferred embodiment, the lowest available component number is assigned in the order that the component is added to the assembly. Thus, the first component selected for an assembly is assigned a first, i.e., least component number, initially, and the second component is assigned that number plus one. Each succeeding component is assigned the lowest, next available component number.

In the systems furniture design tool, every component except one is linked to exactly one other component of lower component number; this component of lower number is called the destination component for the corresponding linked component. One component of the assembly, called a root component, will have no destination component to which it is linked.

A component may be a destination component for more than one component. In most cases the linkage of a component to its destination corresponds to a physical connection but in some cases the components may be linked and have a fixed spatial relationship relative to each other but not be physically connected. For example, two adjacent, connected frames have a physical connection but a chair and a desk may be linked together logically in an assembly without any physical connection.

The interconnection of components for an assembly is available from the design database records but is also available from indexed values. That is, there is a list of all the component numbers used in an assembly and the destination component corresponding to each component.

In order to illustrate a preferred implementation of the device and method of this invention, the specific example of systems furniture design is described here. Example 1, below, provides additional detail regarding the various databases used by the design tool as a precursor to examining the design process itself. Examples 2 and 3 detail variables, menu structure and the process of menu traversal. Example 4 describes the process which occurs when a user digitizes a new Active Component from the graphic display.

While designing an assembly, the user can elect to modify an included assembly design databases "on the fly". The user may also elect to create an assembly and may preload pertinent conditions of the current assembly into this new assembly. This preloading of design constraints ensures that the new assembly will fit logically into the current assembly at the current Active Component. Both of these processes allow the user to make design decisions about an assembly while considering (or being limited by) its use in another assembly.

When designing an assembly the user works within the coordinates for that assembly regardless of whether the assembly being worked on is part of another assembly. Thus, the user only sees the graphical interface for the assembly currently being designed whether or not it is being created or modified. As part of this display, preloaded pertinent conditions may appear as phantom frames.

The assembly of primitive components into contiguous assemblies is accomplished by fitting them together within the assembly coordinate system in accordance with a set of expert rules. The expert user interface in conjunction with the rule base governs the design process. The records in the menu database are indexed by menu number, each corresponding to a different set of selections to be displayed in the menu area of the screen. In addition to this text, each menu contains the expert information which governs its display, its basic reaction to a menu selection, and some basic environmental descriptions such as whether or not the user may currently digitize a new Active Component. The reactions to a selection include: loading the next menu; adding a new component or subassembly to the design database; and changing variable values. See also Examples 2 and 3, below.

The number of, and the logical and physical relationships among, the components in a Tile Typical are completely determined by the design tool. Menu traversal under these conditions can be thought of as a branching system of logical possibilities beginning at the first component and ending at the predetermined point of the last component.

Figure 1C:
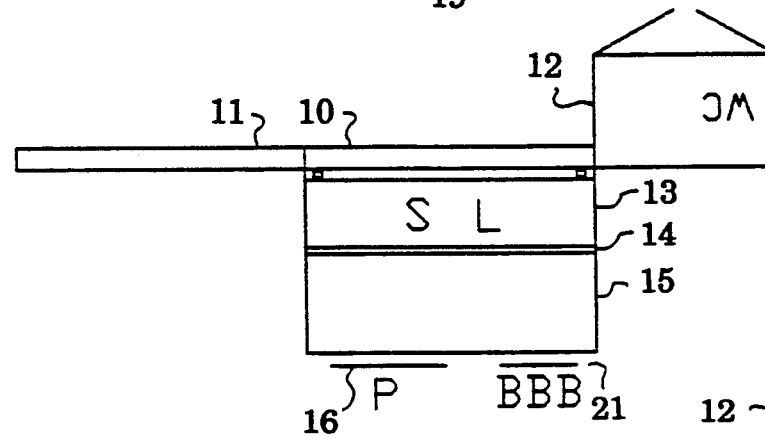
Figure 1D:
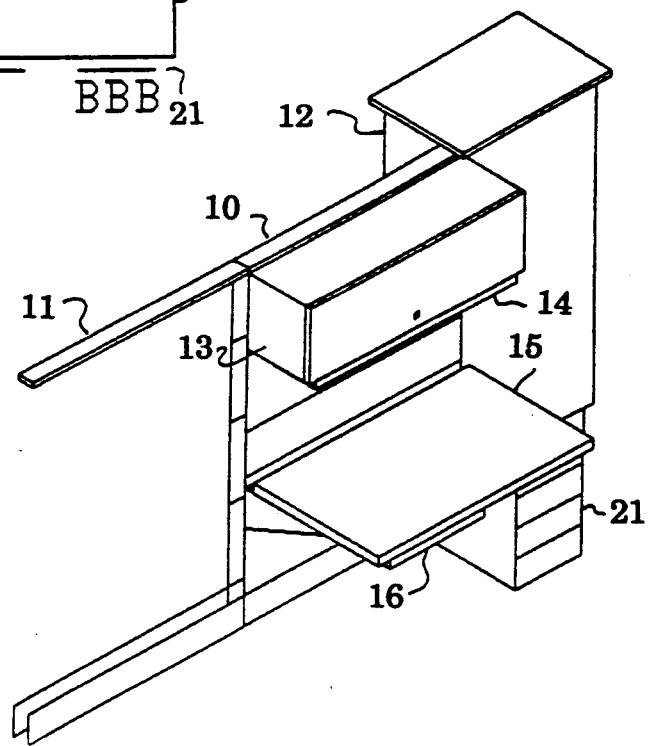
Figure 26:
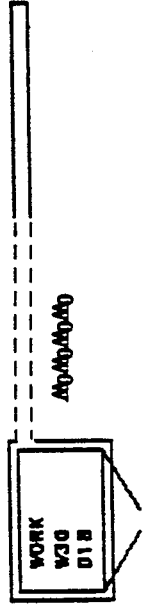

Referring to FIGS. 1B and 1C, components 13, 14, 15, 16 and 21 were added in a single user action by selecting a predefined Interior Typical, 003A in the menu shown in FIG. 26. The Interior Typicals are notable for the fact that insertion of components in these assemblies is subject to wide geometric variation which must be logically controlled. To enable this, whenever an Interior Typical is being designed, a PHframe database is created and modified (see Example 1).

Cluster assemblies differ from Interior and Tile Typicals in that they allow the insertion of assemblies. To facilitate this, a variable CIT (Cluster Interior Tile) database is used to record just the characteristics of each extant assembly which need to be examined in order to determine whether or not the insertion of any given assembly is legal at the current Active Component in a cluster. This prevents the design tool from having to generate this information from each assembly design database every time any assembly is inserted.

At this point we are ready to describe more specific operations of the design process which the user controls via the design tool under the constraints of the design tool.

3. Component Operations

After component selection, if the selected component is activatable that component is the Active Component and the menu displayed is the active menu for that component. A number of variables are maintained by the design tool which describe various aspects of the assembly in which the deign tool user is currently working. These variables represent the status of the assembly. Some of these status variables are specific to the current Active Component and are stored with the record for that component in the design database for that component.

The design process can be broken down into three separate processes: adding components, deleting components, and changing components.

a. Adding Components

The addition of a component to the Active Component is accomplished by selecting a component or type of component from the menu selection in the active menu for the Active Component. The design tool leads the user through a series of menus until the selected component is completely defined both in relation to constant characteristics and in relation to the assembly in which it now occurs. This new component record is added to the design database and to any pertinent temporary databases, and the graphic system portrays it on screen.

During the process of traversing the menu for each menu selection selected ones of the status variables are altered. The inference engine responds to each menu selection by changing information which reflects the consequence of that selection to the current assembly. A subset of this information, i.e., selected variables, is stored in memory in a record corresponding to the component once the component is added.

The added component has the component which was the Active Component at the beginning of the addition process as its destination component. The added component is linked to the destination component and is a new element in the current assembly.

Components may be added in between other components in a process called midrun addition. This process is similar to the process of midrun deletion described below. When a component is added between two or more other components the connectivity and vector information for each of the affected components must be changed as well as shifting the location information within the assembly coordinate system to reflect the changed position of the various assembly parts.

If the new component is activatable, then the new component becomes the Active Component and the user is presented with the active menu for that component. Otherwise, the new menu is the active menu for the previous Active Component.

b. Deleting Components

Deletion of components is accomplished through the user commands. Whether or not a component is deletable is determined by its logical status as defined by the deletability variable. As discussed above, the deletability variable starts at zero for a given component and is incremented by one every time an activatable component is linked to the given component or the given component is linked to another component. Thus, if the deletability variable is greater than one then that component is linked to at least two other components. A root component which does not a destination component will only be linked to other components which have the root component as a destination component.

Each record in the design database for an assembly includes the deletability variable and the component number of the corresponding component's destination component, except for the root component which has no destination component number but does have a deletability variable. The deletability variable and destination components for each component in the current assembly are saved in a temporary database called T_i-sam as discussed below in Example 1. Storage in the temporary database permits quick reference during the design process without having to determine this information from each individual record in the design database.

Deleting a component will also delete all components of lower hierarchical value which are attached to the component to be deleted. That is, when an activatable component is deleted all non-activatable components attached to it will automatically be deleted. This said, there are two distinct methods of component deletion within a design database which are selected depending on the value of the deletability variable for the component which is selected to be deleted.

Method One. (Deletability equal to 1)

Figure 6:
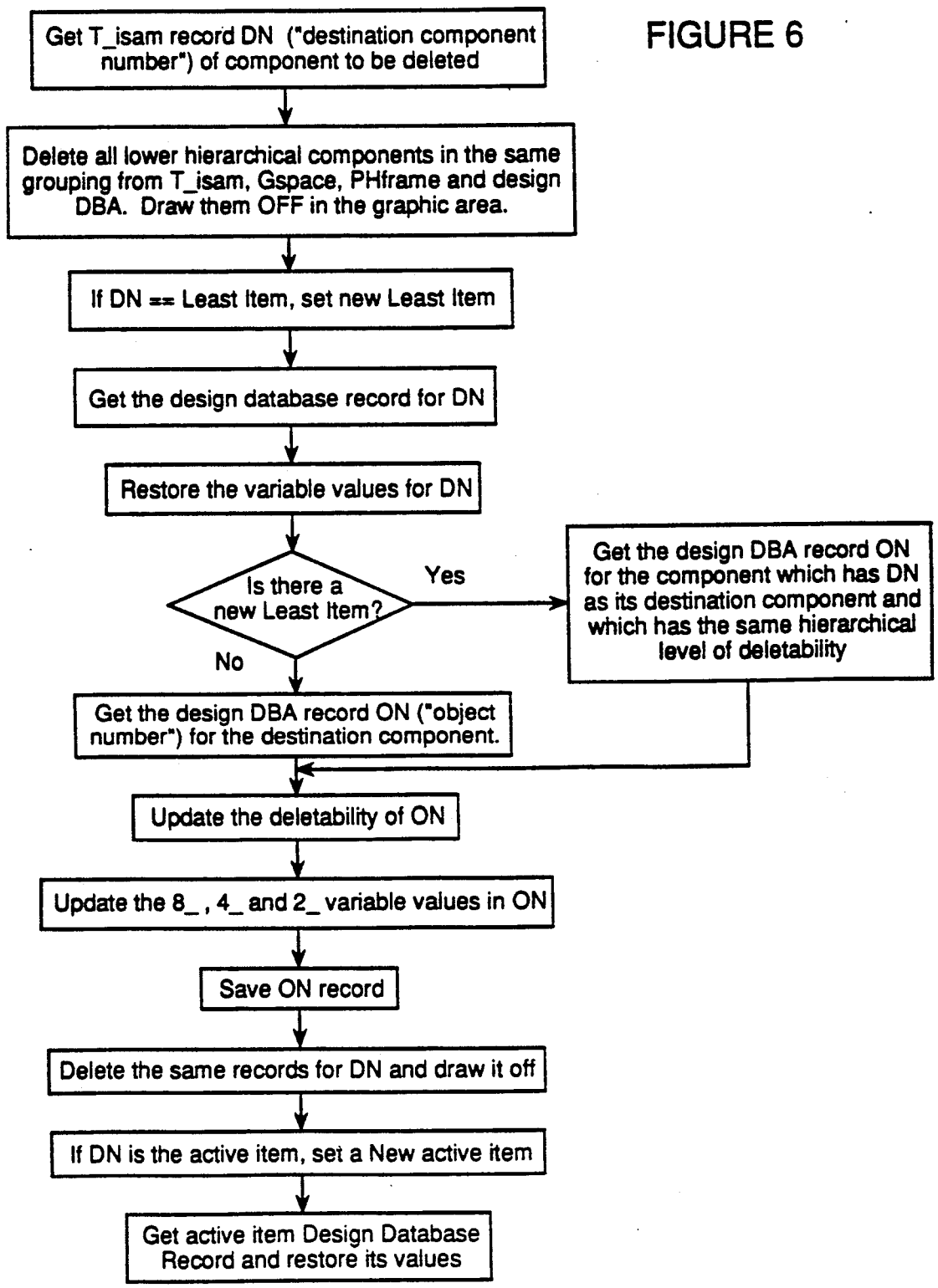
FIG. 6 illustrates a flowchart for the first method of deleting a component.

This form of deletion occurs when a component is deleted which will affect the logical status of some of the remaining components but will not affect the geometrical connections among them. By status we mean status variables such as the deletability variable and vector variables saved in the component record. By definition then, a component deleted according to this method must have no component of equal deletional hierarchical value which lists the component to be deleted as its destination component (unless it is a root component, which does not have a destination component to which the root component is linked and has exactly one component linked to it). Deletion of a component by method one may change whether or not its destination component (or in the case of a root component, the component of equal hierarchical valued connected to it) will be subject to deletion by method one or method two. Referring to FIG. 6, the record number of the component to be deleted is retrieved, the least Item variable is set, an Object Number ("ON") variable is set and the Active Component variable is reset.

Accordingly, this first method of deletion is the simplest method and is used for components which are on the end of or at the beginning of a sequence of addition in assembling an assembly. That is, method one may be used to delete all non-activatable components, activatable components which have no other components linked thereto, and a component in an assembly which has no destination component to which it is linked, i.e., a root component.

In the case of the root component, there can be only one component listing it as a destination component for it to be deletable by method one. Thus, this method is appropriate for deleting end activatable components and all non-activatable components. In this end run deletion, the consequence to the assembly by the deletion of an end run component includes change of variables, and in the case of an activable component, deletion of all non-activatable components connected to it.

Method Two. (Deletability greater than 1)

This form of deletion occurs when the component to be deleted has one or more components of equal hierarchical value linked to the component to be deleted (or two or more if the component is a root component), and these components, along with the destination component of the component to be deleted (if it is not a root component), can be connected to one another automatically in accordance with the expert logic of the system after the component is deleted. This type of deletion is termed mid-run deletion, since it occurs when two activatable components are linked to an activatable component to be deleted, such as in the case where two frames are linked on either side of a frame to be deleted.

In the preferred embodiment of the present invention, this functionality is limited to mid-run deletion of frames, spacers and midrun cabnets. For example, a frame component which has activatable components connected on either side of it can be deleted and the resulting two halves of the assembly be brought together. This process requires that a portion of the assembly separated by the deletion of the midrun component be moved in space to compensate for the component deletion and the appropriate change in the status variables for the component which listed the deleted component as a destination component and the destination component of the deleted component be made. The movement of one half of the assembly in space requires that the graphics displayed be changed as well as location designators. Status variables which may have to be changed are vector variables, and destination component numbers.

When the user elects to delete components by digitizing a window in the graphic area in which all of the elements in that window will be deleted rather than selecting an individual component, the design tool cycles through all of the components within that window repeatedly until no components can be deleted in the current cycle. Each cycle of deletion will change the "deletability" of the components remaining in the window until none are deletable.

c. Changing Components

Changing components in a design database is accomplished through the user commands. Components may be changed globally by logical type, through a digitized window, or individually through component digitization. When a component or a set of components of the same logical type is changed, the design tool cycles through the same set of menus used to describe the component(s) initially, allowing the user to make different selections. Previous selections are highlighted. There are two distinct method of change which can be made:

Method One

The first method of component change alters the variable characteristics of the component but not its logical type, i.e., location (vector variables). This is a straight forward process of altering the values of specific variables which were saved with the component record.

Method Two

The second method of component change alters both the variable characteristics of the component and its logical type. Some components cannot be changed by this method at all, while other components may be changed by this method only if its destination component and the components connected to it conform to a set of logical conditions defined in the expert system.

Through the user commands, the user may elect at any time to save, save with a new name, end, or quit from the design. Quitting from the design does not retain any changes made to the design database. Ending from the design first calls the DRC, then saves the design database in its current form.

4. Assembly Operations

When working in a cluster assembly, the user may elect to insert a tile typical or interior typical at some point. At this point, the user makes the selection for addition of an interior typical or tile typical and is presented with a list of options which include existing tile typicals or interior typicals which would fit with the indicated portion of the Active Component.

At any point in time once an assembly is inserted into another assembly, an included assembly may be digitized for modification of the included assembly during the design process for including assembly. After an assembly is digitized the graphic environment and context of the design tool is changed so the user is now operating within the coordinate system for the digitized assembly. Any changes made to an assembly, even when installed in another assembly, will affect all uses of the changed assembly, even if it is used in other assemblies as an included assembly.

An assembly used in another assembly may always be deleted by a process similar to method one for component deletion since there is no capability for it linking two subassemblies together or linking a component to an included assembly within the included assembly. Within a design database an included assembly is referenced primarily by its location and there is no capability of linking a component onto the included assembly.

EXAMPLES

Example 1

Databases

The design tool for systems furniture uses the following Constant Databases:

a. Part Database

This database contains records which each correspond to different manufacturer's part number for a systems furniture component. These records contain information such as: part number; description; options available (such as trim and finish colors); graphic to draw on screen; parametric graphic values; graphic to use in commercial CAD systems; price; weight; volume; and active menu number (the number of the menu from the menu database which should be loaded if this part is digitized by the user and made active).

b. Geometry Database

This database is referred to by the part database and contains representations of all the possible vectors on a graphic which might be used to connect a given component to another component. By the point to point alignment of connection vectors on different components, an assembly of components is produced. Variable values may modify this point to point alignment axially in either the coordinate system of the component being inserted or the coordinate system of the current design database assembly. Included assemblies are incorporated into an assembly similarly, or by recording the position and orientation of insertion of the included assembly.

c. Option Database

This database is referred to by the part database and contains information such as: option names and descriptions; option upcharge prices.

d. Menu Database

This database, a part of the rule base, contains records indexed by menu number. Each menu produces a screen display and has imbedded in it the logic governing this display and the basic responses to make upon a selection from this display. See Example 3 for a more complete description.

The design tool application for systems furniture uses the following Variable Databases:

a. Project Database b. Cluster Interior Tile (CIT) Database

This database is project specific and is used to obtain information about sub-assemblies in the project without having to open each of their design databases and develop this crucial information individually. The records in this database are saved whenever a sub-assembly is saved and occur in the following forms:

1. CITbase. These records occur for each cluster, interior or tile assembly and record: assembly number, revision, name and description; DRC success; and the number of CITpoi and CITgraph records associated to an interior.
2. CITpoi. These records record the physical locations in an interior assembly which must match with certain types of physical locations in a cluster assembly in order for the interior to be inserted into that cluster.
3. CITgraph. These records record the graphics to be drawn with each interior when it is inserted into a cluster assembly: graphic number; parametric graphic values; location and orientation in the interior coordinate system.
4. CITtile. These records store information about a single tile used in a given project: graphic number; and options. Because of this, when tiles are inserted they will be assigned the correct tile subscript by searching the CIT database for a CITtile record with matching characteristics.
5. CITtileA. These records store information about a tile assembly which is used to determine whether or not it can be inserted onto a given frame component in a cluster assembly: width; height; logical types of tiles.

c. Design Database

This type of database is the primary variable database which occurs for each assembly (or custom component) and records the complete variable characteristics of that assembly. Records occur for each component in the assembly and have slightly different structures according to the type of assembly represented (tile, interior, cluster or space plan). Each of these structures contains the complete logical description of the variable characteristics of the represented component in relation to the current assembly. These characteristics include: component number in the current assembly; name of the component (either a subassembly or a part name in the part database); options selected if the component corresponds to a record in the part database; and a set of variables stored according to logical variable type (see Example 2) which completely record the component's logical condition in relation to the current assembly. In the space plan design database, other records are stored which record the geometry of the building shell, which has been imported via DXF. DXF and IGES are industry standard file formats used for transporting or converting CAD files between CAD and other applications.

d. T_isam Database

This is a temporary database created whenever a tile, interior or cluster assembly is being designed. It records a small number of crucial pieces of information for each record in the design database. The T_isam database is used for rapid indexed searches during design for such information as: component number; destination number (the component number of the component the current component is attached to); the logical type of component; the deletability variable; which vector of the component is attached to which vector of the destination component; graphic number; parametric graphic values; location and orientation of the component in the assembly space; hot rectangles (areas in the assembly space where the component can be digitized and made active); and other information accessed frequently. Appendix B:1-2 shows details of the structure and initialization of the T-isam database.

f. PHftame Database

This is a temporary database created whenever an interior assembly is being designed. In the interior assembly most components are assembled according to the point to point alignment of their connection vectors only in so far as to determine the relative orientations of their component coordinate systems in relation to the interior component system (and therefore in relation to one another). This alignment determines the axial rotations of any component in the interior assembly; however, the actual locations of most components is subject to some variation and is determined by how accurately a user digitizes within the graphic space. In order to prevent logical errors in these user digitizations, it is helpful to limit the range of these digitizations geometrically. This prevents two components from occupying the same physical space or from being assembled out of restricted alignment.

Under these conditions, component position along from one to three axes of the assembly coordinate system is not fixed, yet must be bounded. These boundaries form segments along the coordinate axes which correspond to legal, or allowed, axial positions of insertion.

The intersection of three sets of legal axial positions forms the set of legal points of component insertion. To track the set of legal points of component insertion into an interior assembly by component logical type, the software uses the PHframe database.

The records in the PHframe database correspond to matrices which track the status of various cubic segments in space in the interior assembly coordinate system. This status includes information such as whether or not the cubic volume referenced by the PHframe record matrix is occupied by some portion of some component, and if so by which logical type of component. Each of the records in the PHframe database corresponds to a component in the interior design database know logically as a phantom frame. Every other component in an interior is attached serially (in the manner of a branching tree) to some component which is attached directly to a phantom frame (the root of the tree). The records in the interior T_isam database record the component number of this phantom frame for each component which is not a phantom frame. This phantom frame is known as the destination frame of the component.

An Interior Typical assembly is bounded by a contiguous assembly of phantom frames which are assembled to one another directly or through phantom connectors which provide angular variation at the point of assembly. These phantom frames may be thought of as rectangular segments of a plane assembled to form a fence which "corrals" the Interior Typical assembly. These phantom frames and connectors are well ordered in the sense that logically they all point in the same direction (for example, to the left). Because of this, the software can easily access the phantom frames in a group, compiling the information in their associated PHFrame database records into a single logical representation of the three dimensional space associated with that group of phantom frames. When inserting an interior component into an assembly, the group of phantom frames is formed which might possibly affect or be affected by this insertion. This assembled information constrains both which logical and physical types of components may currently be inserted and which locations and orientations are legal for these legal insertions. This information is set through the use of ACTION variables and automatically when any interior component is made active. Both of these methods are shown in the source code examples in Appendix B.

The design tool for systems furniture uses the following Default Database:

a. Default Database

This database is project specific and records user selectable properties of the design which should be automatically selected during menu traversal. The index is by menu number (i.e., on menu #5100 make selection #7 automatically). As many as ten selections can be defaulted for a given menu. If more than one selection is defaulted, the menu does not auto-select but displays only the defaulted selections.

Database Interaction

The databases reference one another through the following information:

| Part Database | Part Number |
| --- | --- |
| | Geometry Number (Graphic) |

-continued

| | Option Numbers |
| --- | --- |
| Geometry Database | Geometry Number (Graphic) |
| Option Database | Option Numbers |
| Menu Database | Menu Number |
| | Output Part Number and Sub-Assembly Number |
| CIT Database | Sub-Assembly Number |
| Design Database | Component Number |
| | Part Number or Sub-Assembly Number |
| T_isam Database | Component Number |
| Default Database | Menu Number |
| PHframe Database | Component Number |

It is important to note that the temporary databases described above (the T_isam and PHframe databases) are created and modified whenever the relevant design database is being worked on. The contents of these temporary databases is determined essentially completely by referring to the design database and the constant databases. These temporary databases are preferably deleted whenever the design process is terminated.

Example 2

Variables

Variables in the software are each of exactly one of seventeen logical classes which govern the way the variables are used:

a. Action Variable

If while traversing menus one of these variables becomes non-zero, the Inference Engine performs a specific action. These action variables include:

1. ACTCLOSE. Set all closure variables to zero.
2. ACTZERO. Set all zero-able variables to zero.
3. ACTOUT. Add a record to the design database.
4. ACTIHGH. Calculate the maximum vertical segment available on a cluster frame to hang interior components by logical class of interior component and write these values into the set of variables 1XVERT01 through 1XVERT30. Alternatively, calculate whether or not interior components can be hung at the defaulted height by logical type and write 1 or 0 (yes or no) into the set of variables 1XVERT01 through 1XVERT30.
5. ACTVERT1. Same as ACTHIGH but only for logical type one (1XVERT01).
6. ACTFLOOR. Calculate the maximum vertical segment available from the floor for a given width and write the value into the variable 1XVERT01.
7. ACTUNDF5 and ACTUNDF7. Turn off global defaults referred to by the values of these variables (in the menu number ranges 5000+variable value and 7000+variable value).

b. Closure Variable

These variables are saved with all design database records and record whether or not a specific operation has been performed to the component (they close off the possibility of performing this operation again).

c. Quadrant Closure Variables

These variables are saved with cluster design database records and record whether or not a specific operation has been performed to a geometric quadrant of the component.

d. Local Default Variables

These variables govern the automatic selection of operations on some menus according to their values and are stored in the header record of each design database. They can be changed by the user through the User Commands.

e. 0C and 1C variables

These variables are saved with design database records in cluster assemblies. The 0C variables are zero-able while the 1C are not.

f. 0I and 1I variables

These variables are saved with design database records in interior assemblies. The 0I variables are zero-able while the 1I are not.

g. 0T and 1T variables

These variables are saved with design database records in tile assemblies. The 0T variables are zero-able while the 1T are not.

h. 0A and 1A variables

These variables are saved with all design database records. The 0A variables are zero-able while the 1A are not.

i. 0X and 1X variables

These variables are not saved with any records, but are used to make expert decisions during menu traversal. The 0X variables are zero-able while the 1X are not.

j. 8__, 4__ and 2__ variables

These variables are saved with essentially all design database records. They record the values of specific variables in the records which correspond to components attached to connection vectors 1-8, or 1-4 or 1-2 on the current component.

These variables as a whole, then, are sufficient to completely determine the variable aspects of the relation of any component to its assembly, to produce the set of possible logical operations at any point in the design process and to prevent operations which are not possible.

Example 3

Menus and Menu Traversal

The records in the menu database record the expert system logic which governs the design process in terms of menu traversal and, when stored with a design database record, define the variable characteristics of a component. These are highly compressed variable length records which when loaded are decompressed into menu structures. Appendix A includes listings of representative menus. The menu structures each contain multiple, nested copies of several other structures:

a. DMvar (Change Menu Variable)

This structure records an expert system command to change a given variable. The possible change is =, +=, -=, *=, /=, and the possible modifying value is either an unsigned short integer or the value of another variable (which is an unsigned short integer).

b. IF__DMvar (If Then Change Menu Variable)

This structure records an if__then condition which if true will cause an embedded DMvar structure to be executed. The condition is in the form if__variable__condition__value-then__DMvar, where condition can be ==, !=, <=, <<, >=, >> and value can be either an unsigned short integer or the value of another variable.

c. Ifcon (If Condition then Action)

These structures contain a series of one or more (up to ten in the preferred implementation) if__variable__condition__value's which are AND'ed together. If the result is true, the return value from the evaluation of this condition is true (a positive value), otherwise the return is zero.

d. MselAct (Menu Selection Action)

These structures occur with some menu selections and are evaluated and acted upon if the given selection is taken (or, in the case of traversal of the menus which set defaults in the default database, if the selection is selected OR unselected). Each MselAct will contain some of the following information:

1. DMvar(s). Executed immediately upon selection.
2. IF__DMvar(s). Executed immediately upon selection.
3. IFcon(s). Checked when menu is loaded. If true then this selection cannot be taken and will not be displayed.
4. IFcon(s). Checked upon selection. A true IFcon condition followed by a non-zero ACTOUT variable causes a component to be added to the design database with the current variable values.
5. DMvar(s). Executed after IFpart(s).
6. IF__DMvar(s). Executed after IFpart(s).
7. IFcon(s). Checked just before loading the next menu. If true then change the next menu number to the returned value.
8. part(s). Component numbers indicated by IFpart(s) return value(s).
9. DMvar(s). Executed upon unselection.
10. IF__DMvar(s). Executed upon unselection.

The menu structure itself, then, is organized as follows:

a. Menu Number.
b. Flags. These are integers which indicate: single or multiple defaults allowed for this menu; change the menu selection text according to the orientation of the active part, or of the destination part; user can digitize new active item, quadrant, or distance; user can switch from plan to elevation in an interior.
c. Selections. Each selection also has flags (these indicate: next menu number; display help number; associated MselAct number).
d. Help Text.
e. DMvar(s). Executed upon loading the menu.
f. IF__DMvar(s). Executed upon loading the menu.
g. IFcon(s). Executed upon loading the menu. If true then automatically take the selection corresponding to the returned value.
h. MselAct(s). Execute upon menu selection (or unselection).

The menus are broken down into logical categories according to menu number as follows:
1-5000: Menus which cannot be defaulted. These menus contain the primary expert rules governing the interrelation of components in a design. These menus are traversed during the design process.

5001-7000: Menus which are used to set defaults (where each menu has selections corresponding to a set of options available for a record in the option database). These menus are traversed during the process of setting project defaults. These menu numbers correspond to option numbers in the option database.

7001-8000: Menus which are used to set defaults (where each menu corresponds to a design constraint other than the automatic selection of part options). These menus are traversed during the process of setting project defaults.

8001-9000: Menus which are used to set defaults (where each menu has selections corresponding to a set of sub-options available for a record in the option database). These menus are traversed during the process of setting project defaults.

15001-19000: Menus whose selections correspond to menus in the range 5001-9000 but whose selections will be automatically made if a default has been set in this lower range. These menus are traversed during the design process.

19001-25000: These menus function in the same manner as the menus in the range 15001-19000.

Figure 5A:
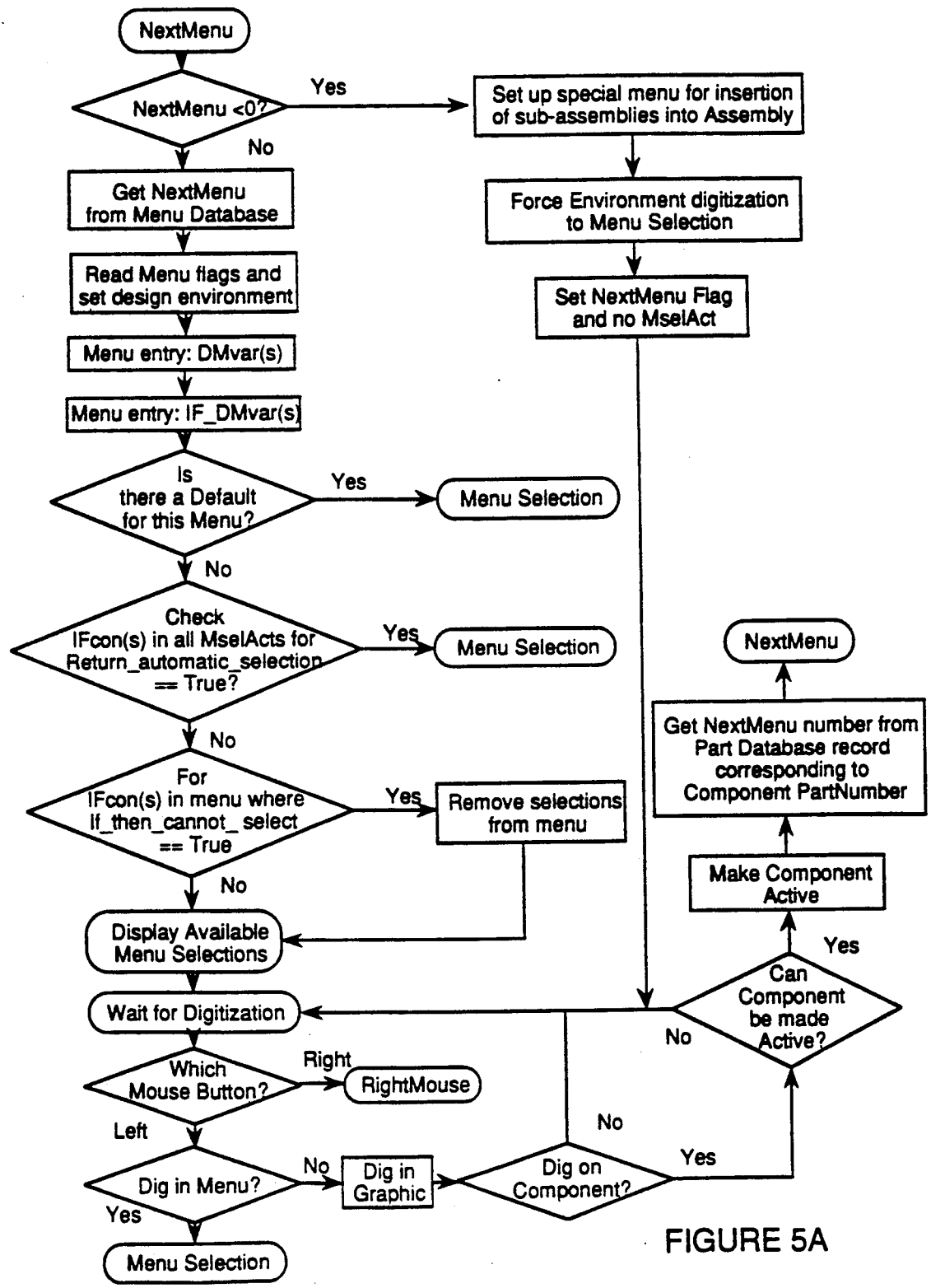
FIGS. 5A and 5B illustrate a logic flow for menu traversal.
Figure 5B:
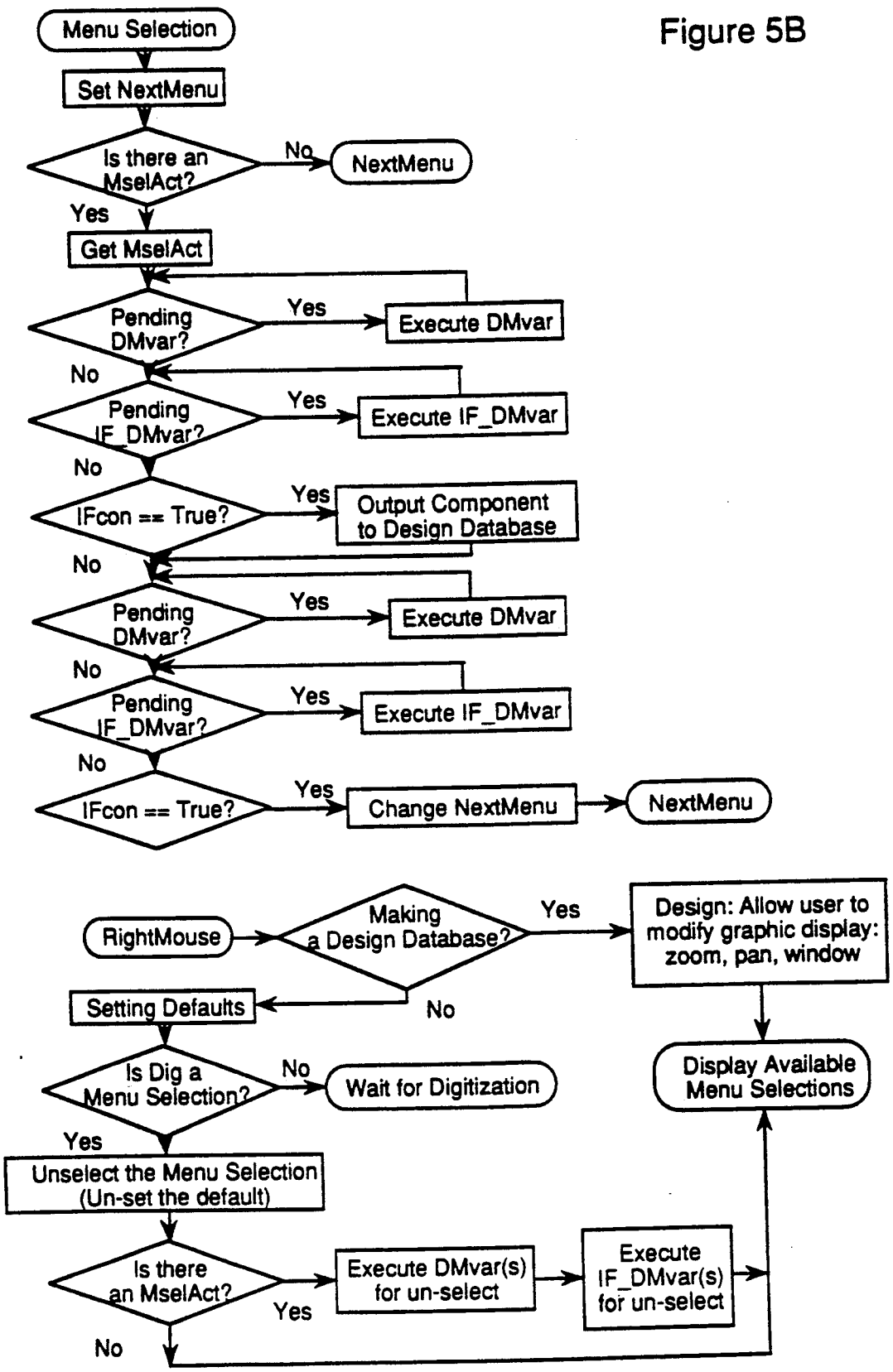

The flow chart in FIG. 5 illustrates the logic and process of menu traversal. Referring to FIG. 5, in setting the design environment, check:

1. In setting defaults, whether single or multiple defaults are allowed;
2. For correct selection of text according to the orientation of the active or destination component;
3. What kind of digitization is allowed in the menu (only select or both select and unselect?):
4. What kind of digitization is allowed in the graphic area;
5. whether a selected component is the Active Component or a new choice of Active Component (consider the quadrant of the Active Component; horizontal or vertical distance on the active component); and
6. Whether switching between interior plan and elevation views is allowed.

Appendix A includes several examples of menu structures. Compare the menu description below (from Appendix page A:5-7) with the corresponding screen shot illustrated in FIGS. 3 and 4 which illustrate the same menu for the same Active Component but with different displayed options, corresponding to the assembly configuration, illustrated in the screen display. The corresponding menu (#18) is encoded as follows:

```
1ACONDES == 2
IF (82HEIGHT>>0)
THEN CANNOT SELECT
Act #5
ACTCLOSE == 1
Act #6
ACTCLOSE == 1
1ACONDES == 8
CLOSE3 == 1
1ACONCUR == 6
IF (CLOSE3 == 1)
THEN CANNOT SELECT
Act #7
ACTCLOSE == 1
1ACONDES == 5
CLOSE4 == 1
1ACONCUR == 6
IF (CLOSE4 == 1)
THEN CANNOT SELECT
Act #8
```

-continued
```
ACTCLOSE == 1
1ACONCUR == 1
1ACONDES == 3
CLOSE5 == 1
OXEVENT1 == 0
OXEVENT2 == 0
OXEVENT3 == 0
IF (0AWIDTH == 24)    THEN OXEVENT1 ++ 1
IF (21FWIDTH == 36)   THEN OXEVENT1 ++ 2
IF (22FWIDTH == 36)   THEN OXEVENT1 ++ 4
IF (0AWIDTH == 30)    THEN OXEVENT2 ++ 1
IF (21FWIDTH == 30)   THEN OXEVENT2 ++ 2
IF (22FWIDTH == 30)   THEN OXEVENT2 ++ 4
IF (0AWIDTH == 36)    THEN OXEVENT3 ++ 1
IF (21FWIDTH == 24)   THEN OXEVENT3 ++ 2
IF (22FWIDTH == 24)   THEN OXEVENT3 ++ 4
IF (CLOSE5==1)
THEN CANNOT SELECT
IF (DEFTPCAP==1)
THEN Goto Menu #209
IF (OXEVENT1 == 3)    THEN OX60TRAN == 1
IF (OXEVENT1 == 5)    THEN OX60TRAN == 2
IF (OXEVENT1 == 7)    THEN OX60TRAN == 3
IF (OXEVENT2 == 3)    THEN OX60TRAN == 1
IF (OXEVENT2 == 5)    THEN OX60TRAN == 2
IF (OXEVENT2 == 7)    THEN OX60TRAN == 3
IF (OXEVENT3 == 3)    THEN OX60TRAN == 1
IF (OXEVENT3 == 5)    THEN OX60TRAN == 2
IF (OXEVENT3 == 7)    THEN OX60TRAN == 3
IF (OXCOMPAR == 0)    THEN OX60TRAN == 0
Act #9
ACTCLOSE == 1
IF (CLOSE7==1)
THEN CANNOT SELECT
Act #10
ACTCLOSE == 1
IF (CLOSE8==1)
THEN CANNOT SELECT
Act #11
IF (1XSPACE>>0)
THEN Goto Menu #93
Menu #18
Uflag 1:   1    NSEW: sub type B
Uflag 2:   1    UNDEFINED
OXCOMPAR == 0
IF (81HEIGHT == 8_HEIGHT)   THEN OXCOMPAR ++ 1
IF (82HEIGHT == 8_HEIGHT)   THEN OXCOMPAR ++ 2
Q Select Next Item To Be Attached To This Frame
  1 Carpet Grippers              IO= 18 →Menu U1= 1 Act#
  2 Electrical Items              IO= 23 →Menu U1= 2 Act#
  3 Structural Item On West       IO= 22 →Menu U1= 3 Act#
  4 Structural Item On East       IO= 22 →Menu U1= 4 Act#
  5 Telephone/Data Symbol         IO= 56 →Menu U1= 5 Act#
  6 Tile Face Assembly On North   U1= 6 Act#
  7 Tile Face Assembly On South   U1= 7 Act#
  8 Transaction Surface           IO= 58 →Menu U1= 8 Act#
  9 Typical Interior On North     U1= 9 Act#
 10 Typical Interior On South     U1= 10 Act#
 11 User Commmands                IO= 20 →Menu U1= 11 Act#
Act #1
1ACONDES == 25
1ACONCUR == 1
ACTCLOSE == 1
CLOSE0 == 1
IF (0AWIDTH == 30)    THEN OALTGEO == 1
IF (0AWIDTH == 36)    THEN OALTGEO == 2
IF (0AWIDTH == 42)    THEN OALTGEO == 3
IF (0AWIDTH == 48)    THEN OALTGEO == 4
IF (CLOSE0==1)
THEN CANNOT SELECT
IF (1XSPACE>>0)
THEN CANNOT SELECT
IF (1AWILDCD==0)
THEN Part #1 G1190.
Part 1: G1190.
ACTOUT == 1
Act #2
OXMEMORY == QCLOSEBA
ACTCLOSE == 1
QCLOSEBA == OXMEMORY
IF (86HEIGHT>>0)
THEN CANNOT SELECT
```

-continued

```
IF (87HEIGHT>>0)
THEN CANNOT SELECT
IF (QCLOSEBA==15)
THEN CANNOT SELECT
IF (1CPOWER==1)
THEN Goto Menu #202
Act #3
ACTZERO == 1
ACTCLOSE == 1
1ACONDES == 1
IF (81HEIGHT>>0)
THEN CANNOT SELECT
Act #4
ACTZERO == 1
ACTCLOSE == 1
```

Example 4

User Digitization of a New Active Component

In the course of menu traversal the user may digitize (select) a new active component from the graphic screen by pressing a mouse button while the mouse is within a hot rectangle (areas in the assembly space where the component can be digitized and made active). For tile, interior and cluster assemblies the location of each hot rectangle is stored in the temporary T_isam database.

Upon digitization, the software retrieves the design database record corresponding to the temporary record which contains the digitized hot rectangle. The part database record corresponding to the design database record is retrieved and used to determine the next menu to be displayed. Zero-able variables are zeroed, and the variable values stored with the design database record are restored. If the assembly being designed is an interior, the PHframe database is referenced to set some variable values which will constrain the design process. The next menu is loaded and displayed.

Example 5

Adding a Component to the Design Database

The addition of a component to the design database requires two conditions. The first of these is a TRUE return value from the evaluation of an IFcon structure in an MselAct structure which indicates that a new component has been determined geometrically, that is, the variables which define its geometric connection to the active item have been set. The second condition is a non-zero ACTOUT variable value. This condition indicates that a new component also has been determined logically, which is to say that all other variables which define the component's variable characteristics have been set.

Figure 8A:
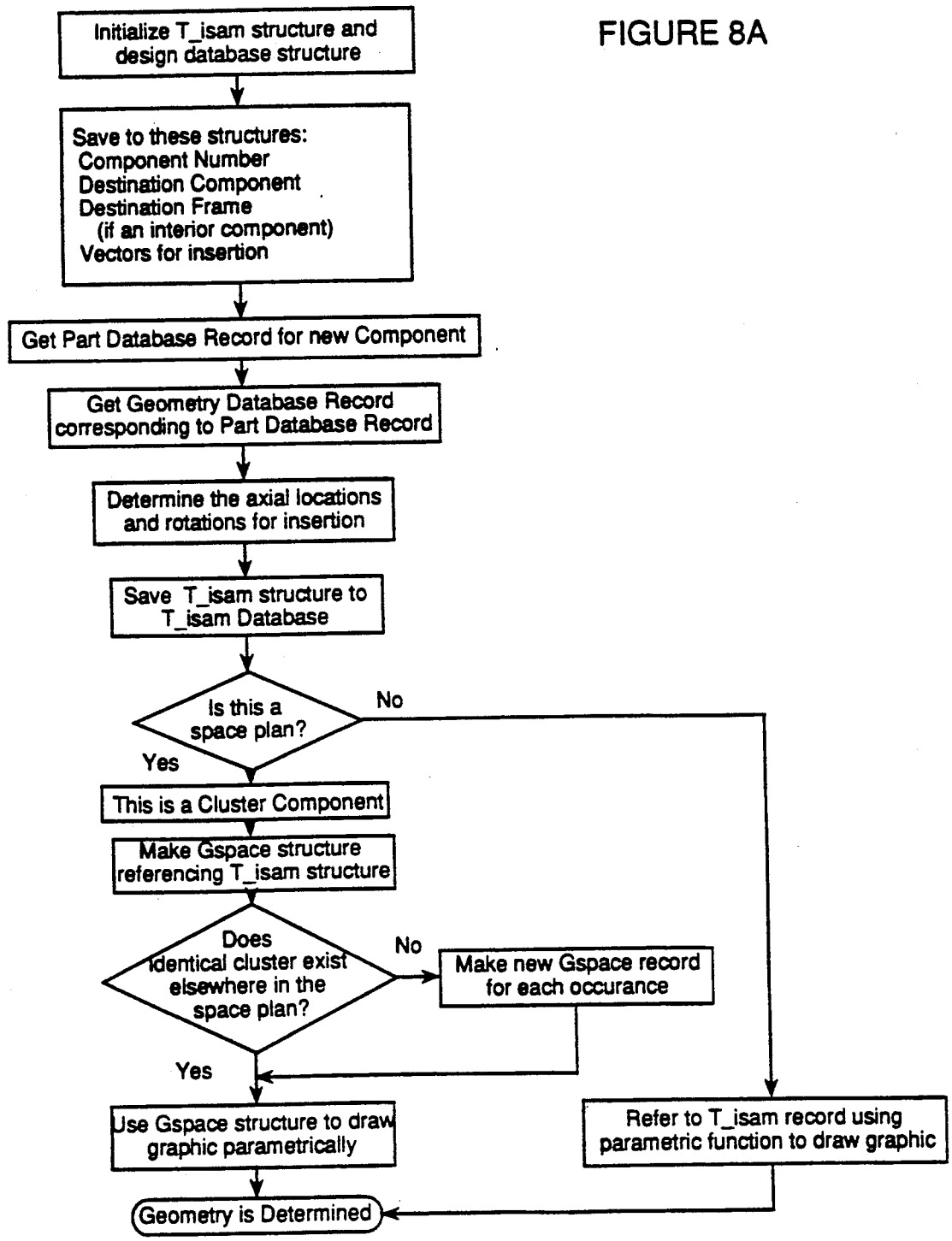
FIGS. 8A and 8B illustrates two flowcharts for adding a component to the design database.
Figure 8B:
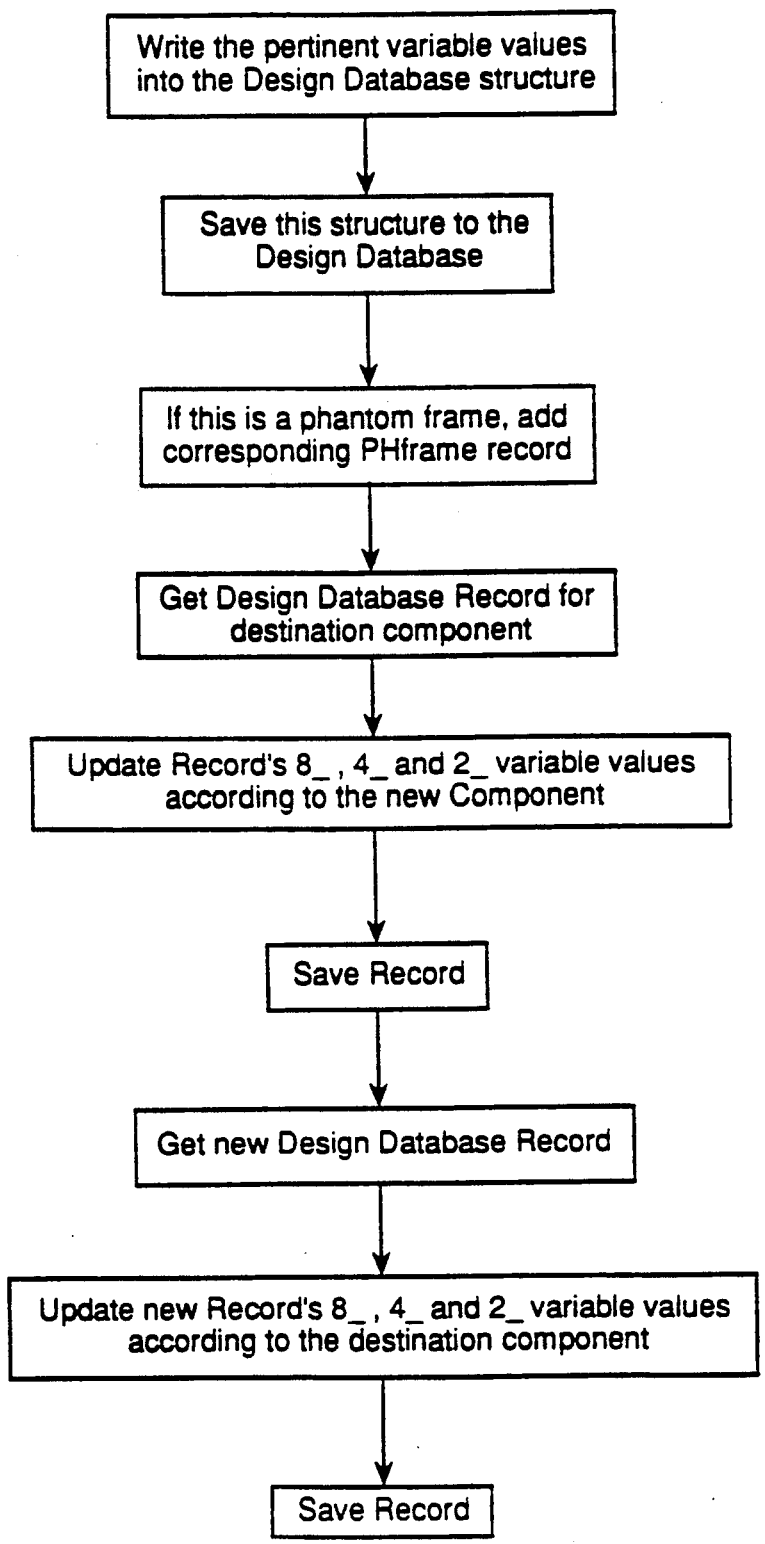

Referring to FIG. 8, the logic flow can be understood. As illustrated in the flow of FIG. 8A the temporary database structure and the current design database structure are initialized. In selecting a component for addition to a current assembly certain information must be stored in the temporary T_isam. As the user makes selections within the menus information is accessed from the knowledge base, i.e., part database record, and geometry database record, in order to fully determine the component. The axial locations and rotations for insertion are also determined using the information from the knowledge base. Once the component is fully determined the temporary information which has been compiled is saved from the T_isam structure to the T_isam database.

The design tool then refers to the T_isam record in order to draw a graphic so that the geometry of the added component is fully determined and displayed. Once the geometry is fully determined selected or pertinent variable values are written into the design database structure which is then saved to the design database. If the component which is being added to is a phantom frame, e.g., interior components in an Interior Typical, the PHframe record is modified. The design database record for the destination component is then modified in order to reflect the addition. That is, information is exchanged between linked components. The vector values for the destination component are updated to reflect the connection of a new component. This record is then saved back to the design database. The new design database record for the added component is also modified to reflect the connections, i.e., changes to the vector variables. And this record is also saved.

If an activatable component is the added component the graphic will be updated so that the added component is the Active Component. Otherwise, the original component which was added to will remain the Active Component. This process of addition is generally true for any type of addition of components. However, in the case of a midrun insertion where one component is added between linked components a special routine must be run which updates the database records for all three affected components as well as shifting the assembly over in space to reflect the addition of the midrun component.

Example 6

Design Rule Check

The design rule check (DRC) involves a check of the assembly design for compliance with local design rules and global design rules. The local design rule check inspects the individual records for each component in the assembly to make sure that each component is configured properly and that the components comply with the local rules defining correct design. Most parameters of individual components are constrained by the design tool to be configured properly during selection and connection so the local design rule check should find few, if any rule violations.

An example of local rule compliance made by the DRC is completeness of an assembly. In order to verify the completeness of an assembly, the DRC checks that all connections in the assembly which must have been used to connect or be connected to another component have been used.

The global rules analyze the assembly in its entirety since these rules look for proper interaction of the components as an assembly and not just the characteristics of individual components. The design rule check (DRC) looks at an assembly globally to check a number of properties and conditions which must exist for an operational, i.e., correct, design. The DRC cycles through the T_isam database and develops information about the design on a global level. Global design rules checked include physically unstable assemblies (designs which will collapse under gravity, for example) and logically unstable assemblies (a electrical circuit design which draws too much power or is discontinuous, for example).

Accordingly, global design rules check properties (DRC) power characteristics such as the loading of a power circuit within an assembly, the continuity of power lines within a powered circuit, the structural correctness of a design, and the support for transaction surfaces, described below. Power characteristics require the testing of all power circuits for continuity and loading at floor level and belt line of an assembly. Also, checked is the relative heights of connectors and frames to ensure they correspond correctly.

Although most components can be linked both logically and physically with a single other component, this is not always the case, i.e., a component may have to be physically linked to more than one component. For example, a transaction surface may extend across and be secured to more than one frame or other component. A transaction surface is a surface such as a desktop which is attached to and extends out from a frame or frames. If the transaction surface is longer than the width of one frame it must be supported and attached to each of the underlying frames. When adding a transaction surface to an assembly, the design tool allows for one destination component for the transaction surface, or, in other words, the transaction surface is logically entered as linked to one other component even if there is an incomplete match in physical reality and the transaction surface actually needs to be connected physically to an additional component. There is no check during the design process of the structural correctness of the assembly for a transaction surface which is longer than one frame since information regarding linkages between components is only exchanged between source and destination components during addition of components.

After performing the design rule check, the design tool can make selected changes and additions to the design database, a process which can be fully automated or performed manually, with or without computer assistance. Such automatic changes include adding end or top caps, height change packages or wiring harnesses where the design defaults for the assembly allow only a single choice for a missing component. The transaction surface check process will detect all frames which do not support the transaction surface and if possible will change appropriate end caps to end caps with transaction surface support.

There are three results of the DRC, i.e., a clean pass, a warning, or a failure. If the assembly checked satisfies all design rules both local and global then the DRC passes on the design and the design has a clean pass. If there is a design flaw which allows the assembly to be constructable a warning may be given. A warning is treated by the system as a clean pass but notifies the user that there is a design fault. The third result of the design rule check (DRC) is a failure. If an assembly fails the DRC returns an appropriate message as to the failure and probable cause of the failure and will not permit some forms of automated outputs from the checked assembly. If missing components cannot be determined automatically, the design tool will register a DRC failure, which will cause the documentation control portion of the design tool to tag the design as incomplete and prevent production of some forms of automated output. Referring to FIG. 2, the bill of materials ends with a "WARNING: CLUSTER(S) in set failed DRC". Referring to FIG. 7, a graphic result of the DRC check highlights incomplete frame 11, which is lacking tile surfaces (see FIG. 1D) and has one end unterminated.

Example 7

Data Structure, Midrun Insertion and Deletion

Each individual record in the design database corresponding to a respective component within an assembly includes sufficient information to identify the relationship of the corresponding component to other components in the assembly. In a present preferred embodiment of the invention the interconnection of components is defined by the linkages between the components.

Each record of the design database contains information completely and independently defining the state of the corresponding component. This information controls the rule based design and consequent graphical and menu display for an activatable component. For a non-activatable component the state information relates to the rule based design of the activatable component to which it is connected. The variables which contribute to the definition of the logical state of the component are closure variables, quadrant closure variables, and identity information for that component.

The physical state of a component relates to the geometric relationships of that component to all other components connected to it. The variables which help define this state include the 8_, 4_, and 2_vector variables and destination component number. The vector variables for a particular record indicate the vector linkages of the corresponding component and of those components linked to the corresponding component.

Each record in the design database for a component includes three types of information: information relating to the linked list of geometric connectivity, information shared by adjacent components, and other state information. The examples above disclose additional information regarding variables and design database structure. The information relating to the linked list of geometric connectivity is that information which identifies the component number of the corresponding component and the component number of the destination component.

The information shared by adjacent components includes the vector variable information and closure variables. The linkage of one component to another results in the newly added component being designated the source component and the component which it is linked to designated as the destination component, as referred to above. The record corresponding to a component contains the value of the vectors at which it is linked on the corresponding component or components and the vector values on itself to which other components are linked.

The linkage of one component to another causes closure variables on both the source and destination component to change. A component has a set of closure variables for possible linkage of certain types of component. For example, when an outlet is added to a frame, a closure variable indicating the closure of that position on the frame for outlets is changed to reflect that condition. A similar variable on the outlet component is modified to reflect closure of the position on the outlet.

Quadrant closure variables are variables indicating the overall closure status of a frame based on the addition of components. The quadrant closure variable is incremented every time a quadrant of a frame, for example, is "closed" in the sense that no further components may be added. The value of the quadrant closure variable is redundant to other closure variables which are individually specific to particular types of components to be added to a component.

Additional information stored in each record for a component in the design database is information pertaining to the logical state or status for the corresponding component. This information includes identity information such as, the size and part number of the component. Information relating to the possible deletion of a component is stored as the deletability variable.

Addition of a component involves exchange of information between the source and destination component and modification of the deletability variable to reflect the new logical state of each component. The design database for each component can be accessed and operated on in a random access fashion. That is, components may be added to, deleted from or modified in the database without regard to the order which these operations are performed to the assembly. The deletability of a component controls the response of the system to a command to delete that component. The process of deletion is referred to above in the section on the design process under the subsection "b. Deleting Components".

Every time an active component is linked to another active component the deletability of the two components linked is incremented by one. An active component with no links has a deletability of zero. Therefore, only those active components which are linked to two other active components will have a deletability greater than one.

The components having a deletability of greater than one are linked to two or more components of equal hierarchical value, i.e., two active components, and are deleted according to method two. In a preferred embodiment of the invention, method two allows for deletion of those components of deletability of two or greater by employing a separate routine which can modify the assembly so the components connected to the deleted component are linked after deletion. Presently, the design tool used for this form of deletion employs a midrun deletion routine.

The midrun deletion routine allows frames, spacers and midrun cabnets linked to two other activatable components on either side to be deleted and the resultant gap be eliminated by connecting the resultant assembly portions. This involves a three step process. First, the midrun routine refers to the record of component linkages and selects the two which must be linked to compensate for the deleted component. Appropriate information, as described above, is then exchanged between the corresponding records for the two components. The graphical information for the components attached to one of the frames to be linked, as well as the graphic information for that frame, is modified so that the position of the associated portion of the assembly is shifted an amount sufficient to compensate for the deleted frame.

In all other cases of deletion of a target activatable component having a deletability variable value of greater than one the activatable components linked to the target component must be deleted before the target component is deleted. Once the linked component or components are deleted the target component will have a deletability variable value of one and can be deleted by method one.

A midrun insertion routine is used by the expert system to take advantage of the modular, random access capacity of the records for the components in an assembly. That is, using a process similar to the one described above for the midrun deletion routine certain components (e.g., frame connectors, frames, and midrun cabnets) can be added between two existing frame components. The insertion is made to the records in the design data base with the appropriate exchange of information and the graphic position of portions of the assembly are modified to reflect the addition.

Example 8

Cluster Assembly Formation

FIGS. 3, 4 and 9-29 show a sequence of displays, i.e., a series of screen dumps, which show the progress of a simple design session. The session will be summarized in the following paragraph and then discussed in detail below. The session begins by reviewing default values, then a series of menus presents available actions and choices. Starting with a 48" frame, a second 48" frame is added, then a 30" work cabinet. The center frame is built up with one of several preselected tile face assemblies, Tile Typicals, on the south and a predesigned Interior Typical on the north. FIGS. 1 and 2 illustrate some of the automated output generated from this simple design (two and three dimensional CAD drawings and a bill of materials). Appendix A includes several representative menus, including those displaying screens in FIGS. 3, 4, and 9-29. Compare FIG. 29 with A-4 or FIGS. 13, 3, 23, 25, 4, and 28 with A-5-7.

Figure 9:
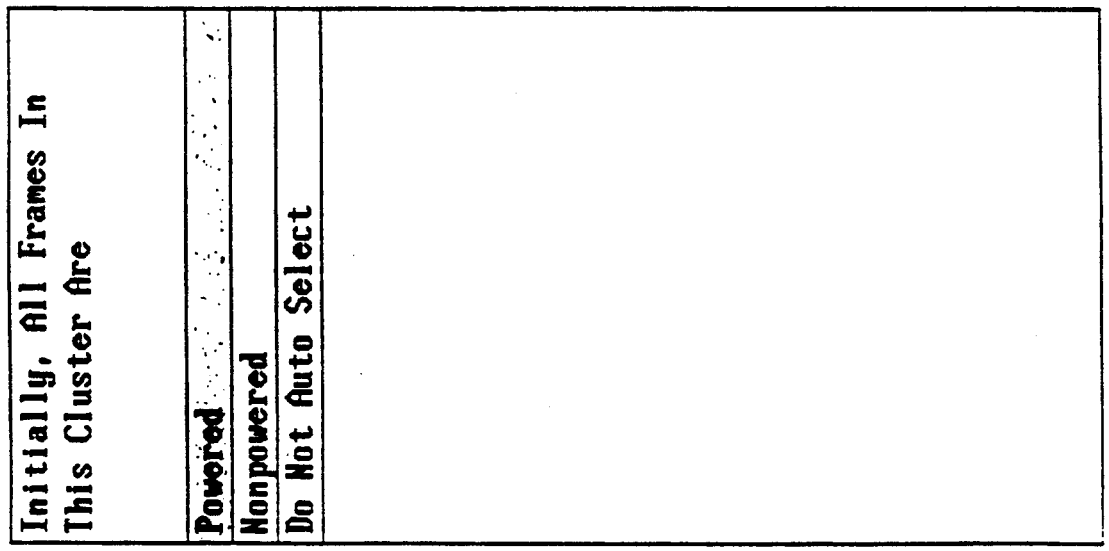

FIGS. 9 and 10 show two default selection menus. In FIG. 9 the user is given the option of selecting whether or not the frames are powered or nonpowered. In accordance with this type of default selection if the user selects the powered or nonpowered option the inference engine will make the selection at the appropriate time without any user input. Otherwise during selection of each frame a menu will appear asking whether or not the frame should be powered or nonpowered. In FIG. 9 the user has selected powered. Likewise, in FIG. 10 the user has selected that all frames in the cluster assembly have a height of 70".

Figure 11:
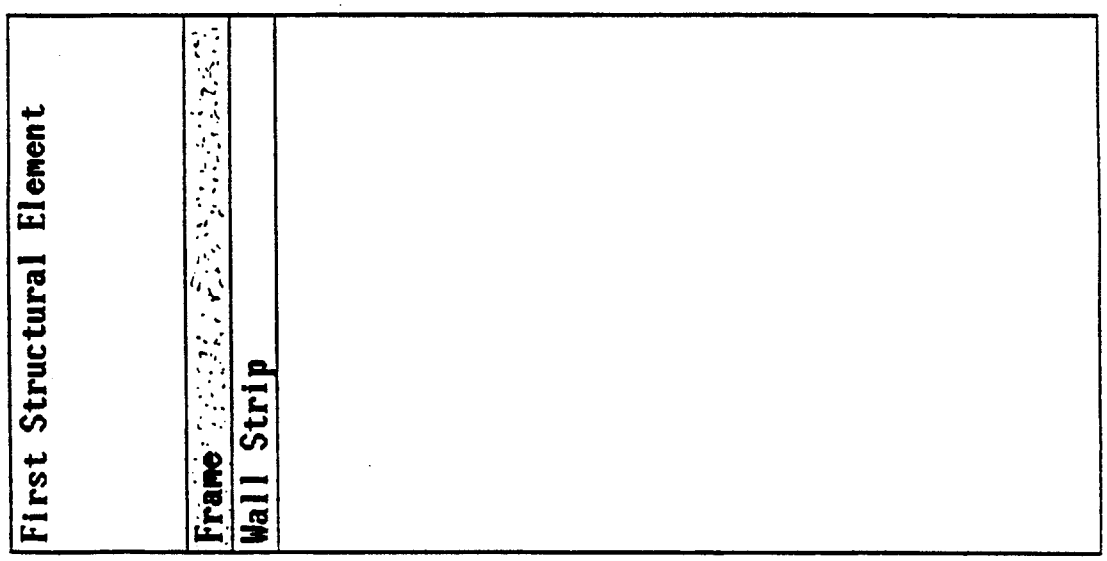

After selecting default values the user is given a choice of structural elements to add. As shown in FIG. 11 the user is given the choice of adding a frame or a wall strip. In FIG. 11 the user selects a frame.

Figure 12:
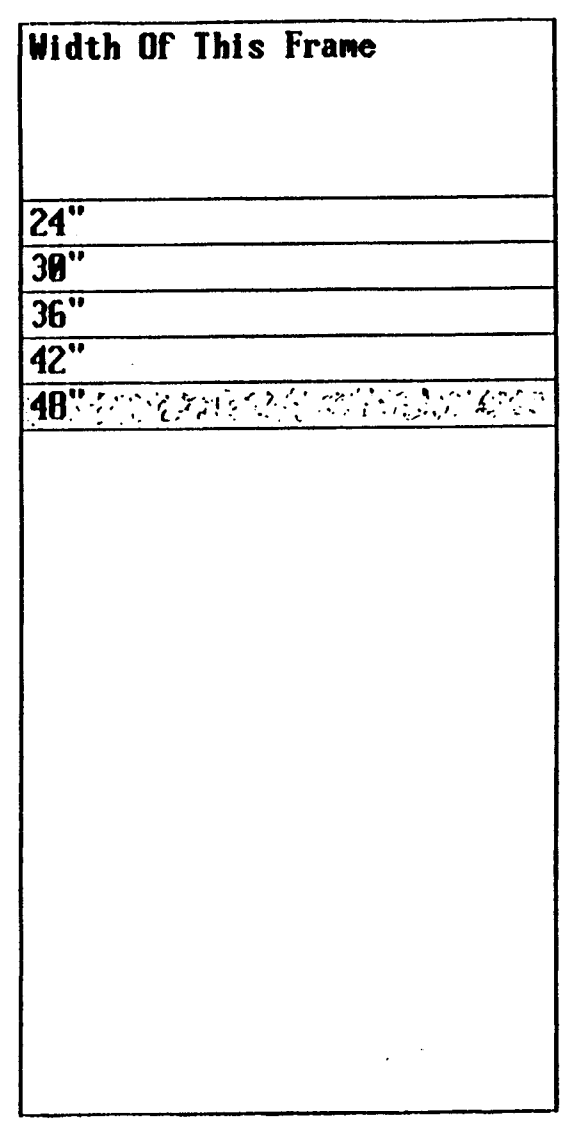

Once the class of component is selected, e.g., a frame, the user is presented with menus of selectable constant characteristics for this classification of element so that a final component is determined. In FIG. 12 the user selects that the width of the frame should be 48". The menu for the height of the frame was auto selected so the height of the frame is 70" without any user input.

Figure 13:
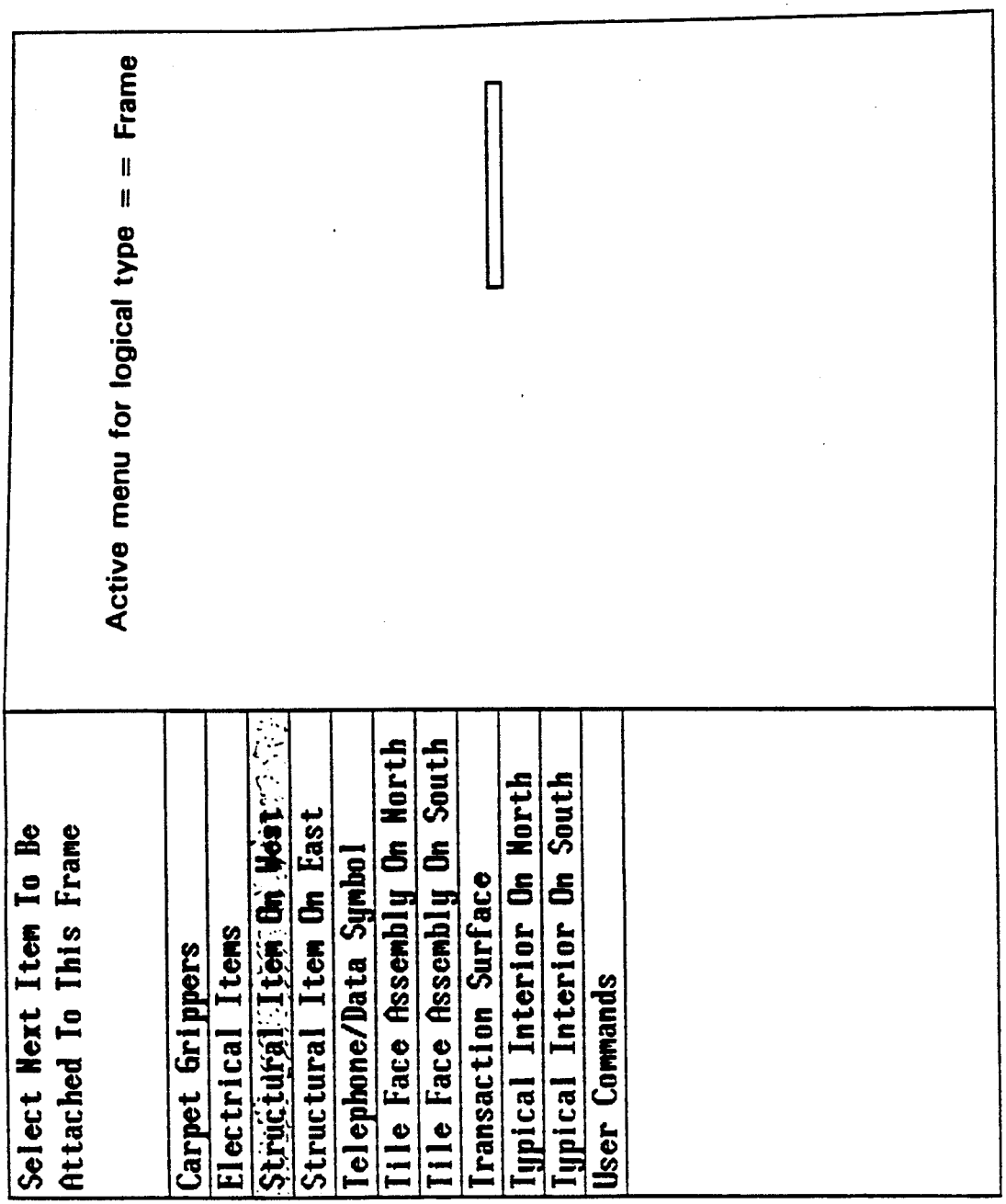

As shown in FIG. 13 after the component is fully determined a graphical representation of the component is displayed in the graphic window. If the component added is an activatable component, after it is added that added component will be the currently Active Component. The menu displayed will be the active menu for that Active Component. FIG. 13 illustrates the user making selection of adding a structural item on the west side of the Active Component.

Figure 15:
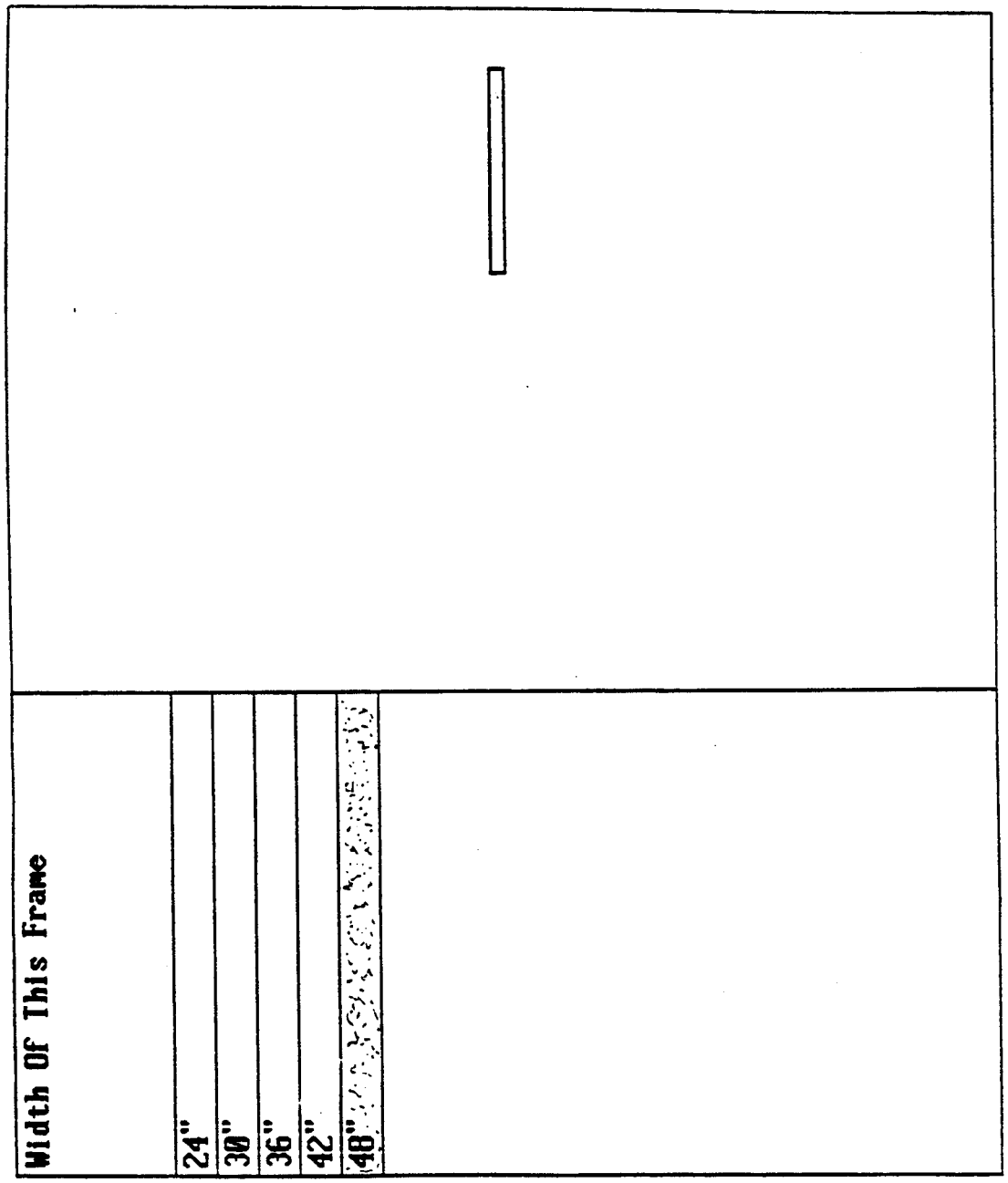

After selecting the option of adding a component onto the west side a menu displaying the possible components to be added onto the west side is displayed as illustrated in FIG. 14. The user makes the selection of adding a frame. After the user selects the type of component menus are again displayed which allow the user to select the characteristics of the component to be added. As shown in FIG. 15, the user selects that the width of the frame to be added on the west side of the first frame is 48".

Now that this second frame is fully defined it appears in the graphical window as the Active Component. Further, the menu displays a series of possible options in connection with this currently Active Component. These selections are either User Commands or additions to be made to the Active Component as shown in FIG. 3.

Figure 16:
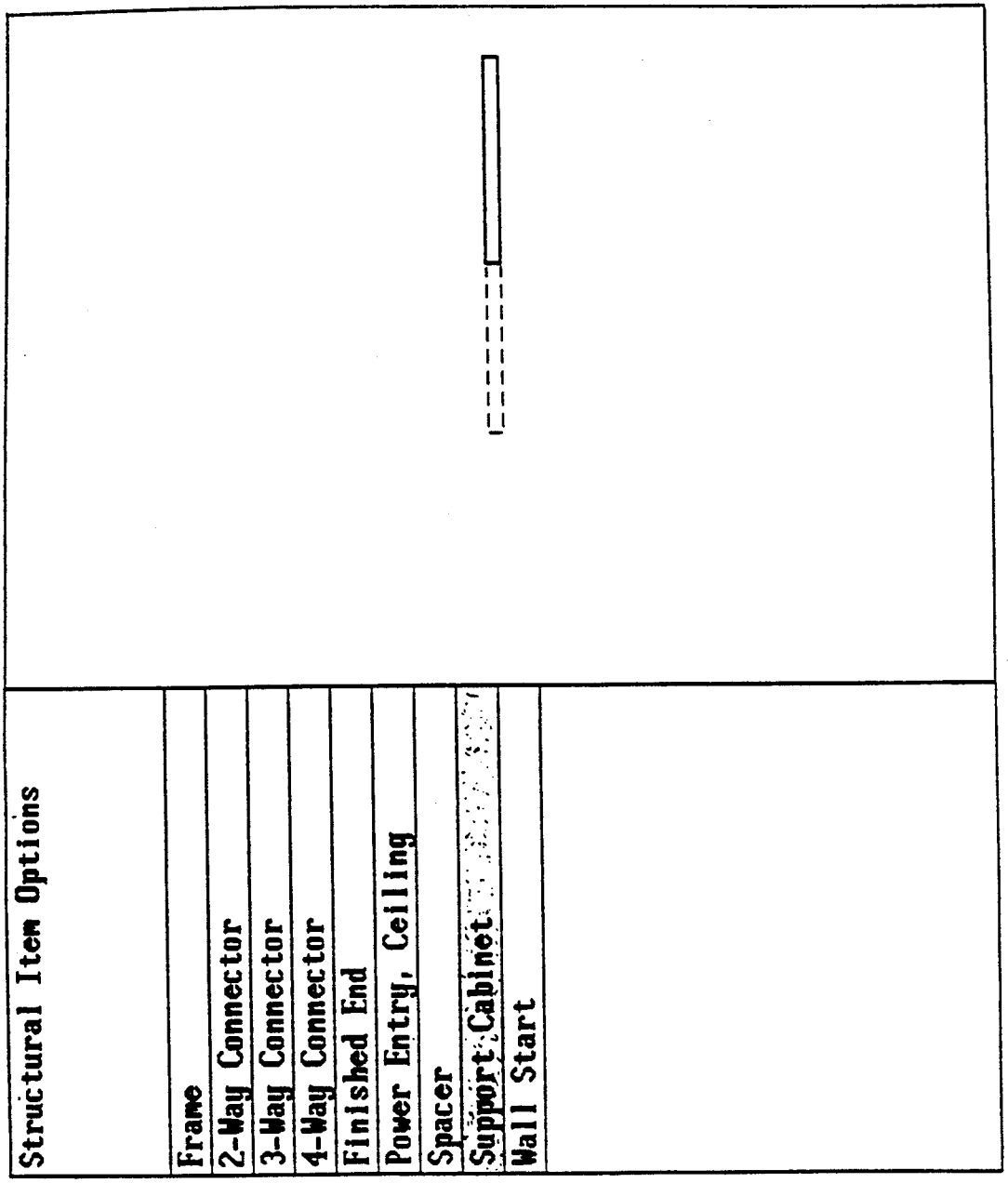
Figure 17:
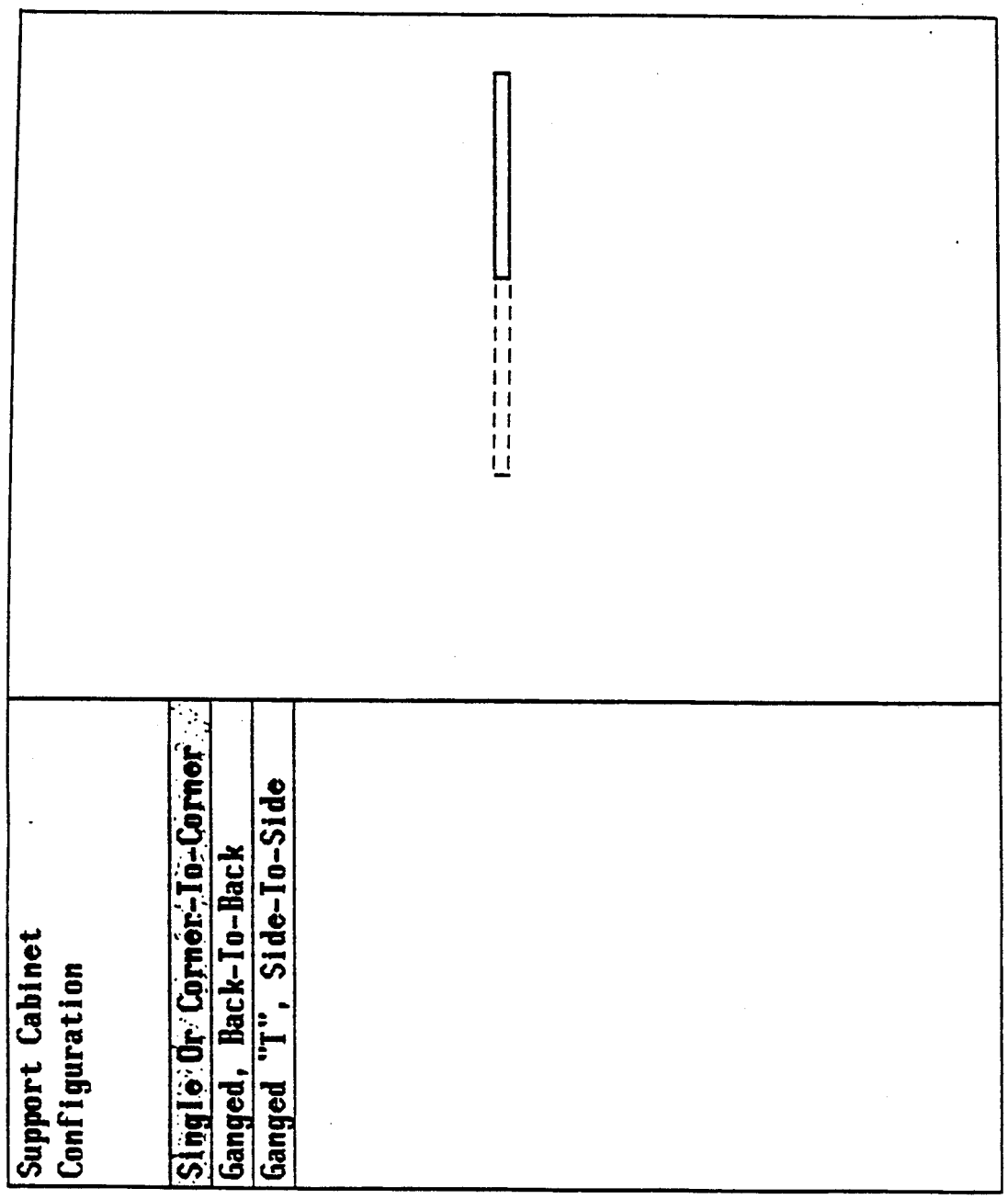
Figure 18:
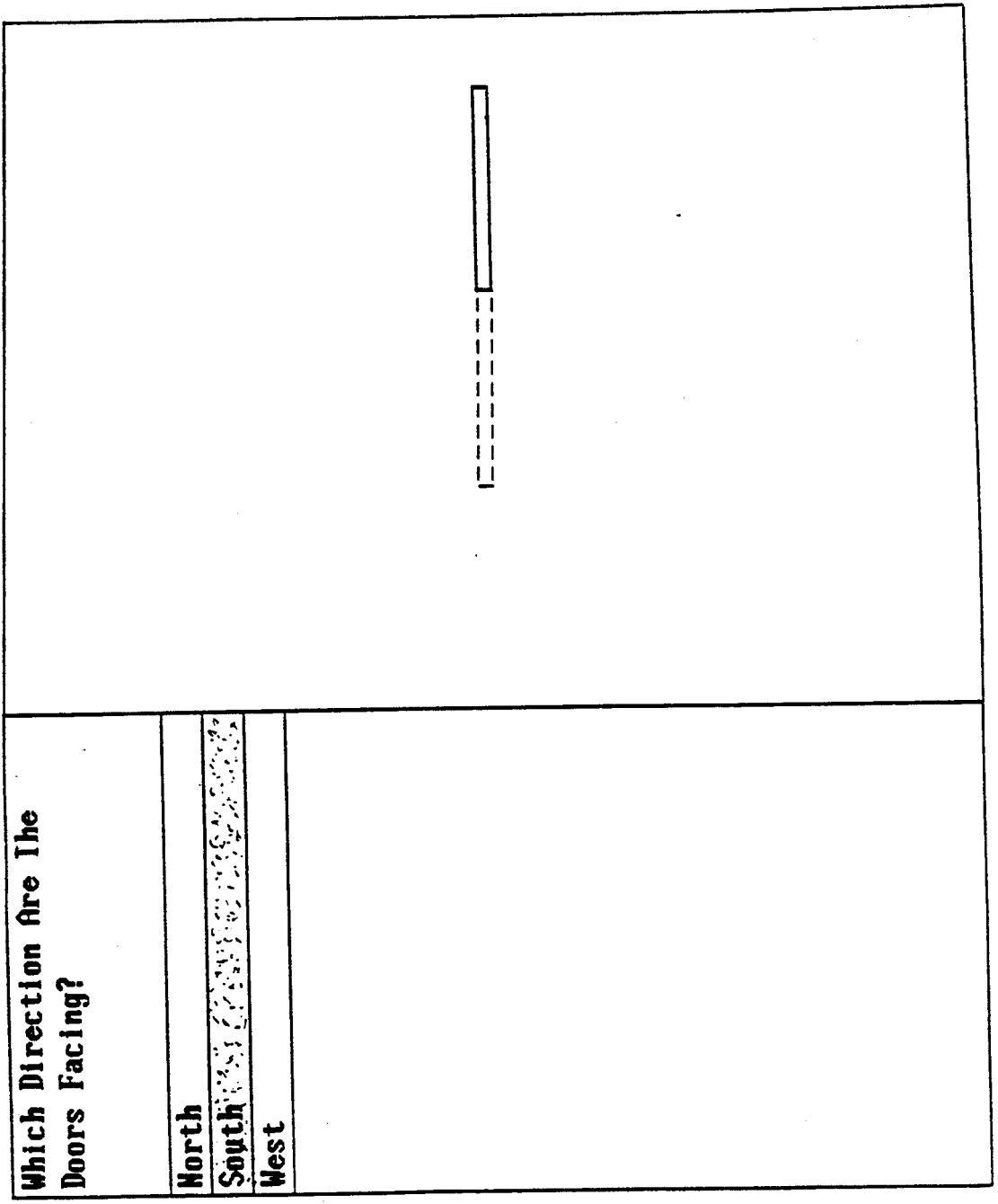
Figure 19:
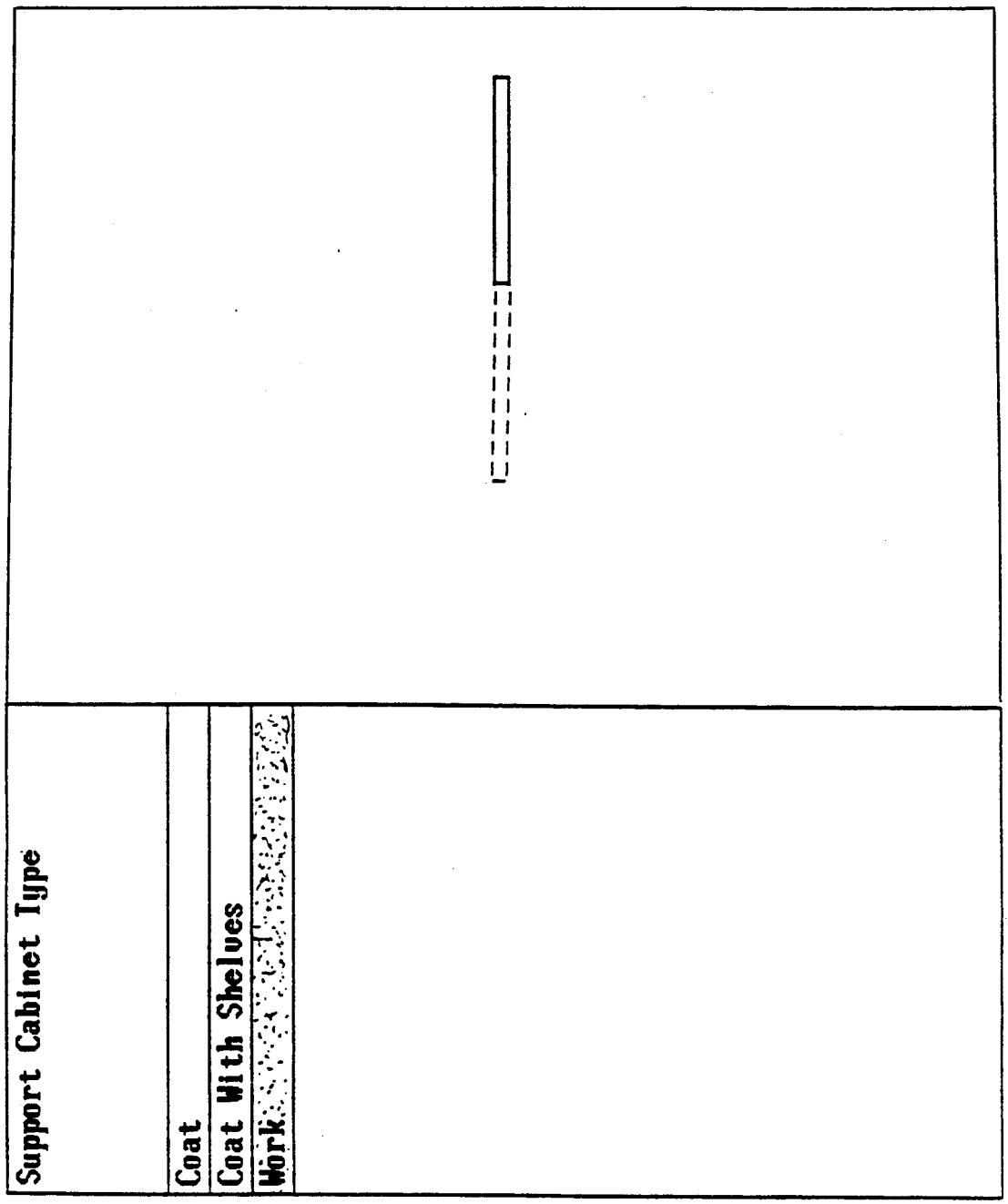
Figure 20:
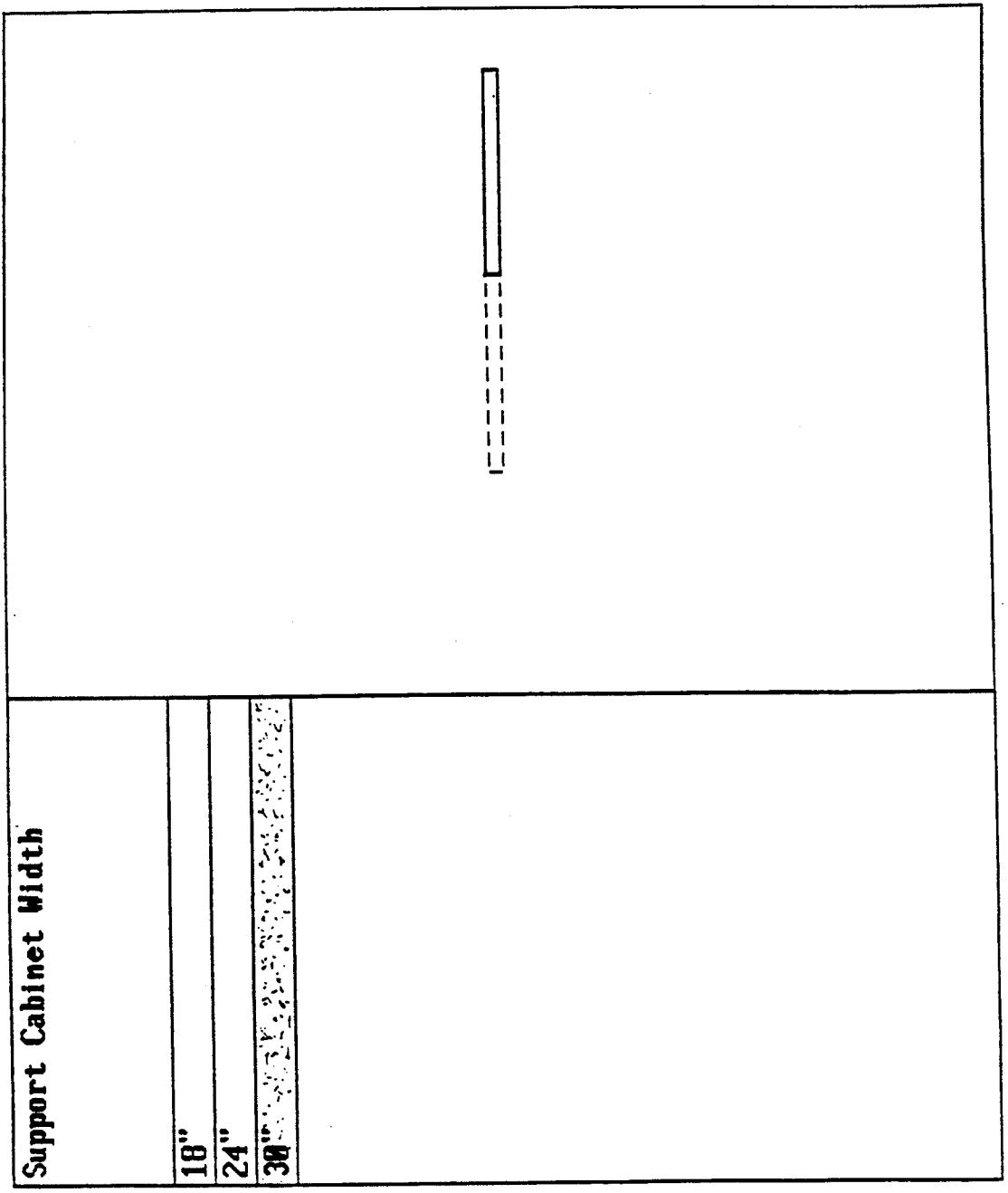
Figure 21:
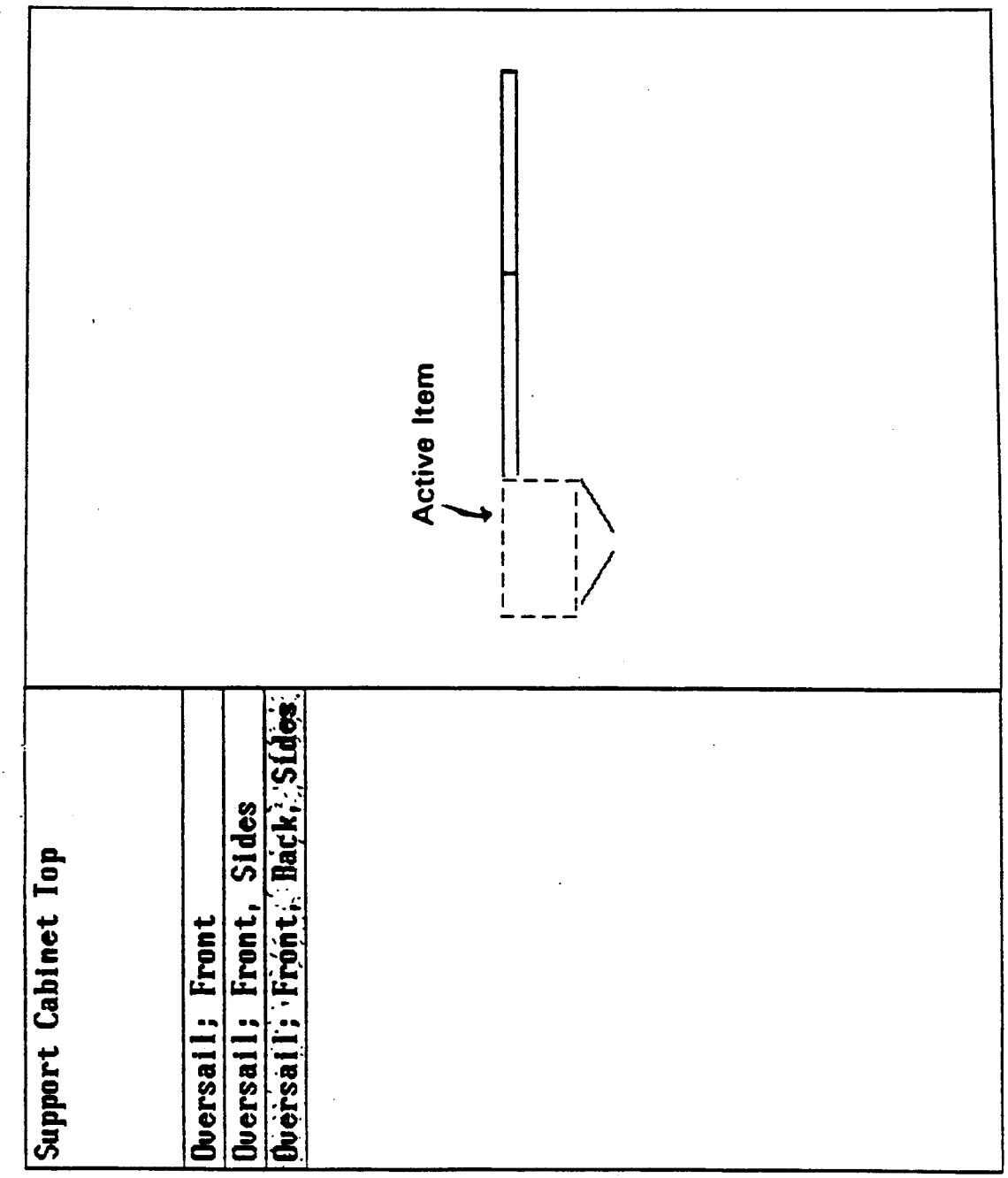

Since the user selects to add a structural component from the menu illustrated in FIG. 16 the next menu displays the options for this classification of component. From these structural item options the user selects a support cabinet.

Figure 22:
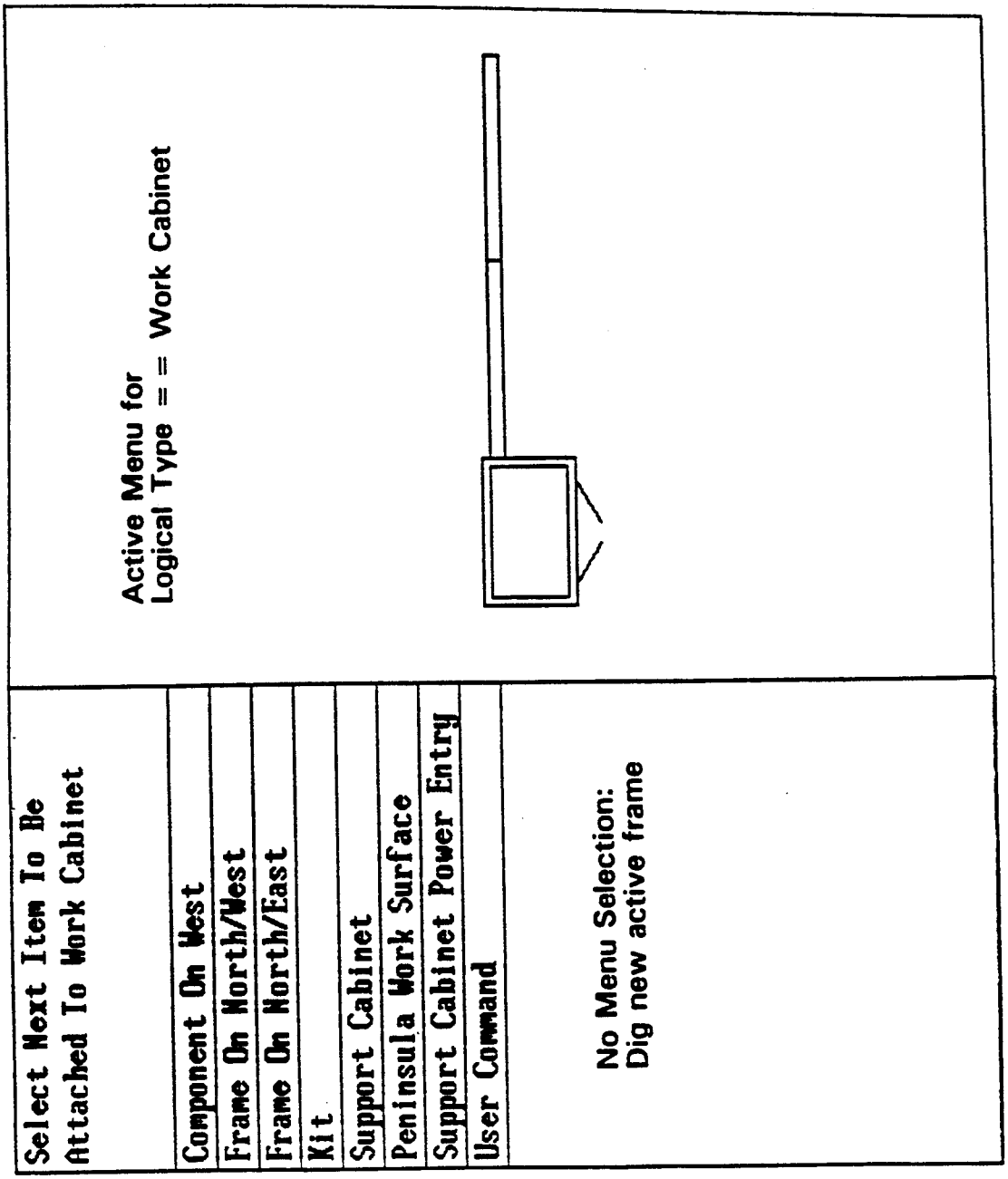
Figure 23:
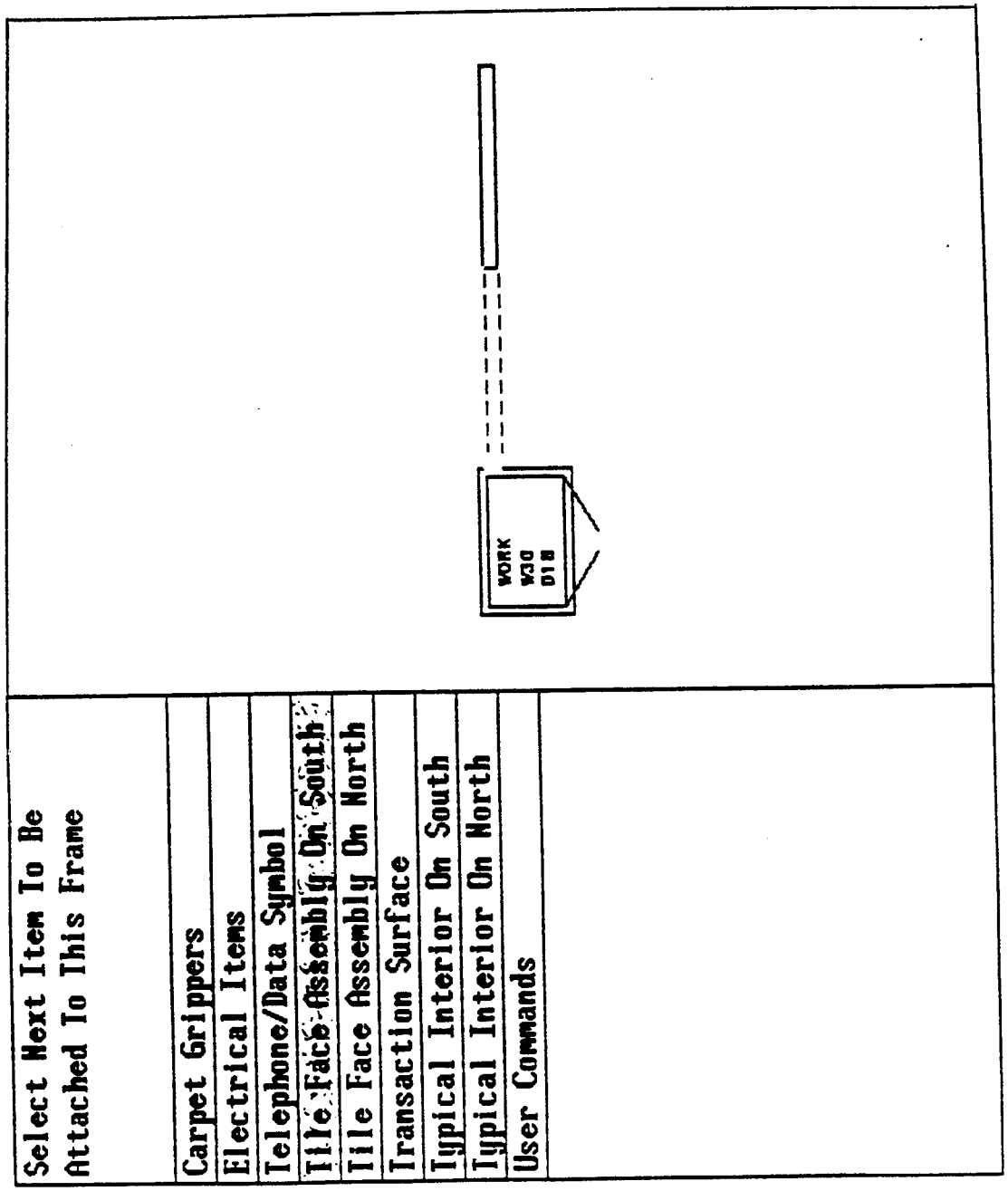

Once the user selects a support cabinet the design tool presents menus from which the user makes selections which fully define the support cabinet until the support cabinet is displayed in the graphic environment and made the Active Component as illustrated in FIGS. 17-22. In FIG. 22 the user digitizes a frame which becomes the Active Component as illustrated in FIG. 23. In FIG. 23 the option menu for this Active Component is illustrated. The user selects to add a Tile Face assembly on the south side of the active frame. A user response to this selection is illustrated in FIG. 24. The user is given the option of selecting from existing Tile Typicals or to make a new Tile Typical or Tile Assembly. The user selects A0A0A0A0 as the Tile Typical to be added.

Figure 25:
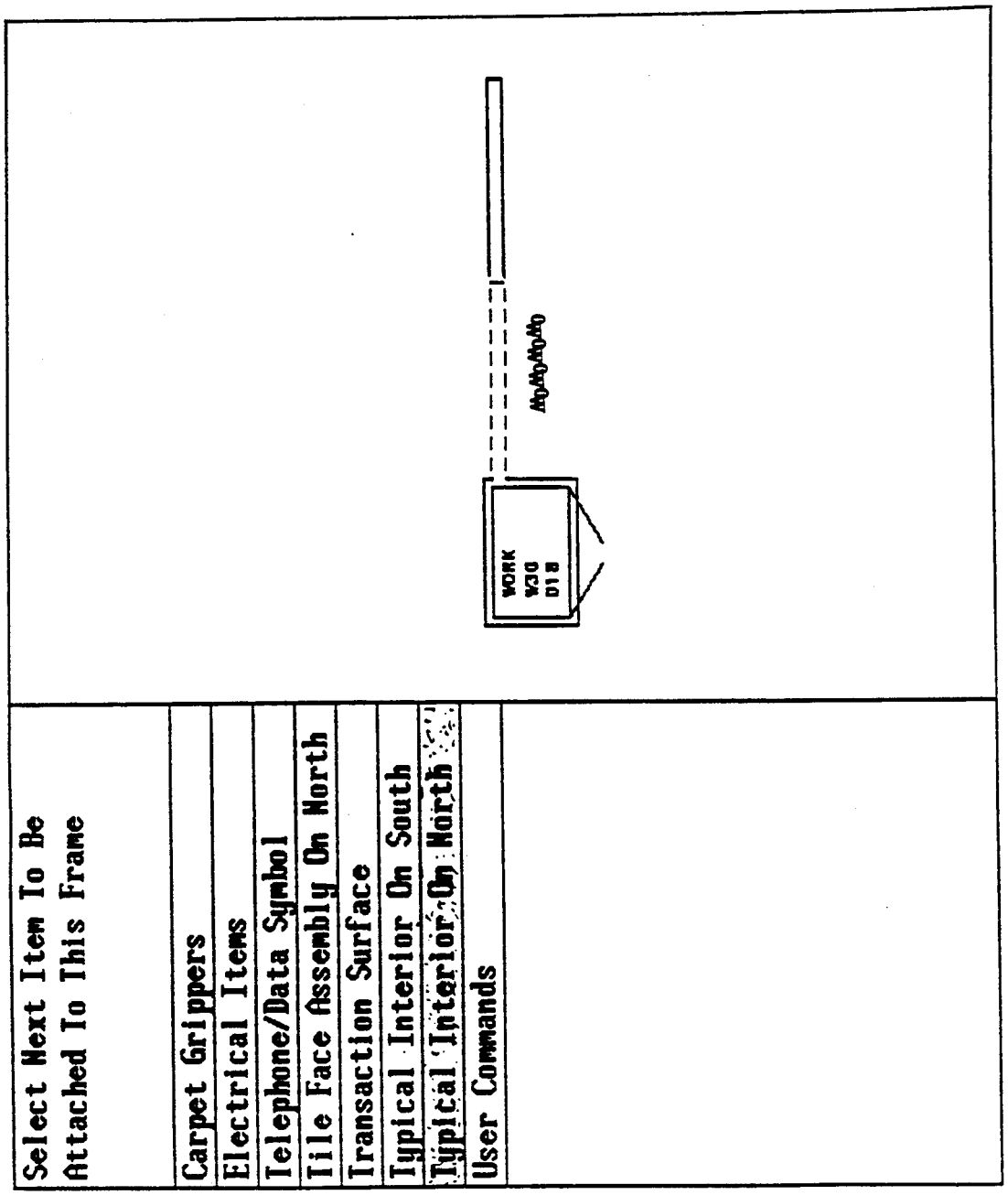

After addition of the Tile Typical the user is returned to the active menu for that frame. As illustrated in FIG. 25 the option of adding a Tile Face Assembly on the south has been eliminated by the inference engine. Accordingly, the user selects to add a Interior Typical on the north.

Figure 27:
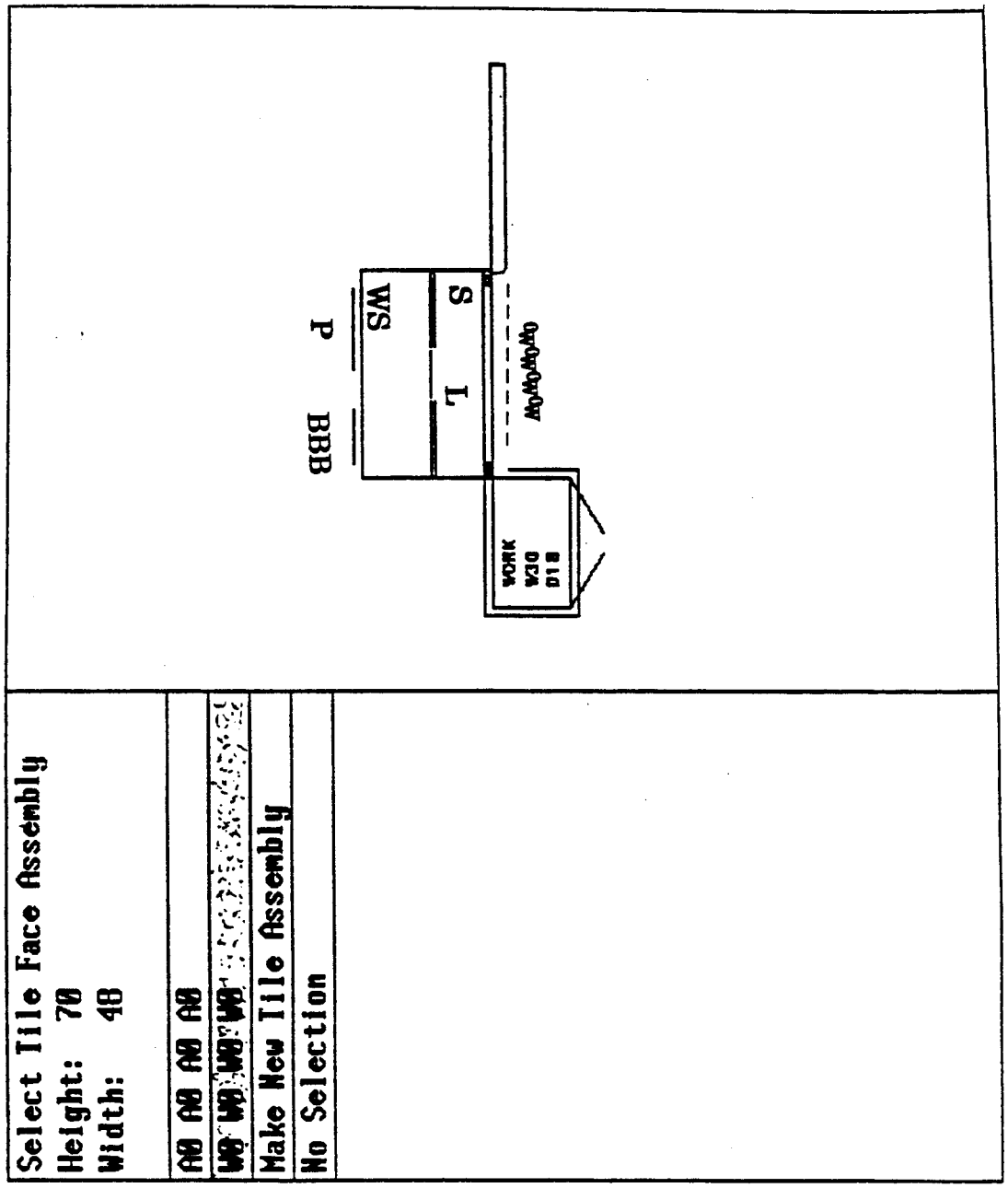
Figure 28:
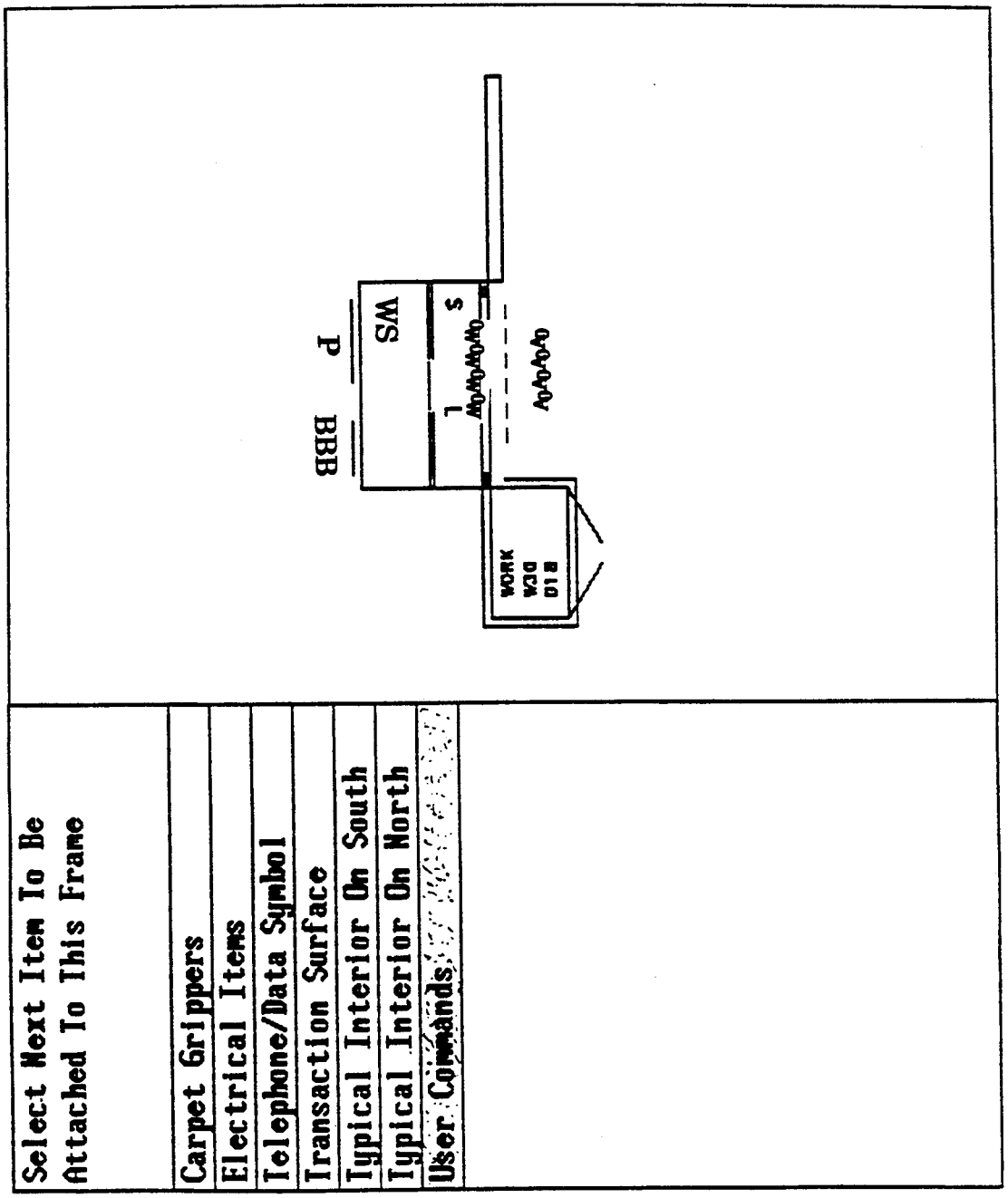

Again, the user may select an existing Typical as shown in FIG. 26. The user selects an Interior Typical and it is added to the assembly as shown in the graphical window in FIG. 4. The menu for the frame as an Active Component is illustrated in FIG. 4 from which the user elects to add a Tile Face Assembly, i.e., Tile Typical on the north. FIGS. 27 and 28 illustrate the addition of a Tile Typical. In FIG. 28 the user selects user commands and initiates DRC upon exit from the assembly design.

Figure 29:
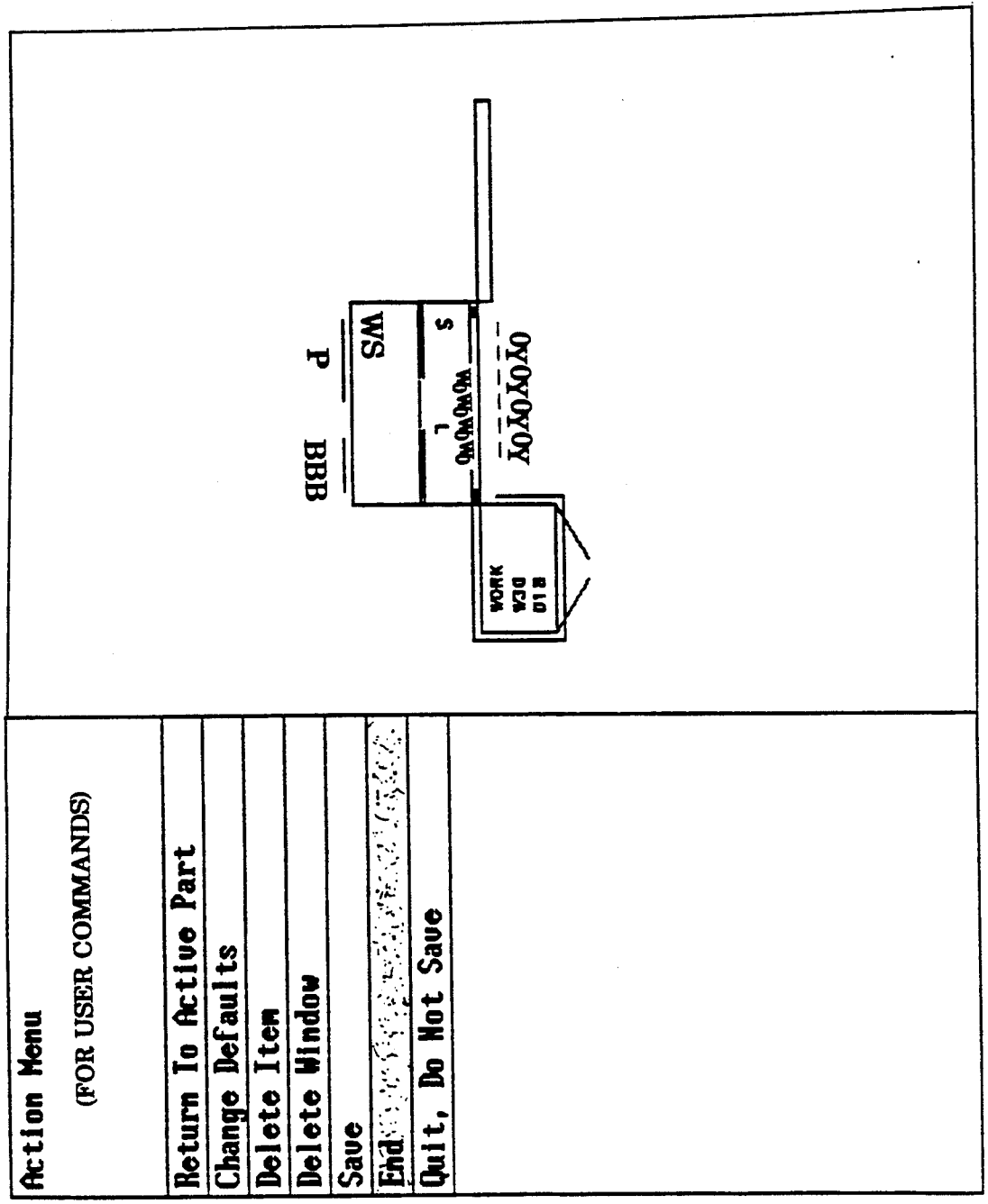

The DRC is initiated automatically by the user selecting end from the action menu for user commands as shown in FIG. 29. As discussed above the FIG. 7 illustrates a DRC failure with a highlighted item showing a completeness failure.

As will be understood by those skilled in the art, many changes in many aspects of the process described above may be made by the skilled practitioner without departing from the spirit and scope of the invention, which should be limited only as set forth in the claims which follow.

```
Menu #213

IF (1CIRCUIT==1)
THEN SELECT #1    4 Circuit
IF (1CIRCUIT==2)
THEN SELECT #2    4 Circuit, Shielded Q Power Circuit Options, Frame 1 4 Circuit                          IO=15078 ->Menu  U1=  1 Act#
  2 4 Circuit, Shielded                IO=15078 ->Menu  U1=  2 Act#

Act #1
0ADEPTH == 24
IF (8_HEIGHT==38&&0AWIDTH==24)
THEN Part #1 E1110.3824E
IF (8_HEIGHT==38&&0AWIDTH==30)
THEN Part #2 E1110.3830E
IF (8_HEIGHT==38&&0AWIDTH==36)
THEN Part #3 E1110.3836E
IF (8_HEIGHT==38&&0AWIDTH==42)
THEN Part #4 E1110.3842E
IF (8_HEIGHT==38&&0AWIDTH==48)
THEN Part #5 E1110.3848E
IF (8_HEIGHT==54&&0AWIDTH==24)
THEN Part #6 E1110.5424E
IF (8_HEIGHT==54&&0AWIDTH==30)
THEN Part #7 E1110.5430E
IF (8_HEIGHT==54&&0AWIDTH==36)
THEN Part #8 E1110.5436E
IF (8_HEIGHT==54&&0AWIDTH==42)
THEN Part #9 E1110.5442E
IF (8_HEIGHT==54&&0AWIDTH==48)
THEN Part #10 E1110.5448E
IF (8_HEIGHT==70&&0AWIDTH==24)
THEN Part #11 E1110.7024E
IF (8_HEIGHT==70&&0AWIDTH==30)
THEN Part #12 E1110.7030E
IF (8_HEIGHT==70&&0AWIDTH==36)
THEN Part #13 E1110.7036E
IF (8_HEIGHT==70&&0AWIDTH==42)
```

```
THEN Part #14 E1110.7042E
IF (8_HEIGHT==70&&0AWIDTH==48)
THEN Part #15 E1110.7048E
IF (8_HEIGHT==86&&0AWIDTH==24)
THEN Part #16 E1110.8624E
IF (8_HEIGHT==86&&0AWIDTH==30)
THEN Part #17 E1110.8630E
IF (8_HEIGHT==86&&0AWIDTH==36)
THEN Part #18 E1110.8636E
IF (8_HEIGHT==86&&0AWIDTH==42)
THEN Part #19 E1110.8642E
IF (8_HEIGHT==86&&0AWIDTH==48)
THEN Part #20 E1110.8648E
IF (OXCHANGE==1)
THEN Goto Menu #187
Part  1:  E1110.3824E
Part  2:  E1110.3830E
Part  3:  E1110.3836E
Part  4:  E1110.3842E
Part  5:  E1110.3848E
Part  6:  E1110.5424E
Part  7:  E1110.5430E
Part  8:  E1110.5436E
Part  9:  E1110.5442E
Part 10:  E1110.5448E
Part 11:  E1110.7024E
Part 12:  E1110.7030E
Part 13:  E1110.7036E
Part 14:  E1110.7042E
Part 15:  E1110.7048E
Part 16:  E1110.8624E
Part 17:  E1110.8630E
Part 18:  E1110.8636E
Part 19:  E1110.8642E
Part 20:  E1110.8648E Act #2
OADEPTH == 30
IF (8_HEIGHT==38&&0AWIDTH==24)
THEN Part #1 E1110.3824L
IF (8_HEIGHT==38&&0AWIDTH==30)
THEN Part #2 E1110.3830L
IF (8_HEIGHT==38&&0AWIDTH==36)
THEN Part #3 E1110.3836L
IF (8_HEIGHT==38&&0AWIDTH==42)
THEN Part #4 E1110.3842L
IF (8_HEIGHT==38&&0AWIDTH==48)
THEN Part #5 E1110.3848L
IF (8_HEIGHT==54&&0AWIDTH==24)
THEN Part #6 E1110.5424L
IF (8_HEIGHT==54&&0AWIDTH==30)
THEN Part #7 E1110.5430L
IF (8_HEIGHT==54&&0AWIDTH==36)
THEN Part #8 E1110.5436L
IF (8_HEIGHT==54&&0AWIDTH==42)
THEN Part #9 E1110.5442L
IF (8_HEIGHT==54&&0AWIDTH==48)
THEN Part #10 E1110.5448L
IF (8_HEIGHT==70&&0AWIDTH==24)
THEN Part #11 E1110.7024L
IF (8_HEIGHT==70&&0AWIDTH==30)
THEN Part #12 E1110.7030L
IF (8_HEIGHT==70&&0AWIDTH==36)
THEN Part #13 E1110.7036L
IF (8_HEIGHT==70&&0AWIDTH==42)
THEN Part #14 E1110.7042L
IF (8_HEIGHT==70&&0AWIDTH==48)
THEN Part #15 E1110.7048L
IF (8_HEIGHT==86&&0AWIDTH==24)
THEN Part #16 E1110.8624L
IF (8_HEIGHT==86&&0AWIDTH==30)
THEN Part #17 E1110.8630L
IF (8_HEIGHT==86&&0AWIDTH==36)
THEN Part #18 E1110.8636L
```

Appendix Page A-1

```
IF (8_HEIGHT==86&&0AWIDTH==42)
THEN Part #19 E1110.8642L
IF (8_HEIGHT==86&&0AWIDTH==48)
THEN Part #20 E1110.8648L
IF (0XCHANGE==1)
THEN Goto Menu #187
Part  1:  E1110.3824L
Part  2:  E1110.3830L
Part  3:  E1110.3836L
Part  4:  E1110.3842L
Part  5:  E1110.3848L
Part  6:  E1110.5424L
Part  7:  E1110.5430L
Part  8:  E1110.5436L
Part  9:  E1110.5442L
Part 10:  E1110.5448L
Part 11:  E1110.7024L
Part 12:  E1110.7030L
Part 13:  E1110.7036L
Part 14:  E1110.7042L
Part 15:  E1110.7048L
Part 16:  E1110.8624L
Part 17:  E1110.8630L
Part 18:  E1110.8636L
Part 19:  E1110.8642L
Part 20:  E1110.8648L
```

Appendix Page A-2

Appendix Page A-3

```
Menu #20

0XSAVEME == 0

Q Action Menu

1  Return To Active Part           IO= 20 ->Menu
  2  Change Defaults                 IO= 19 ->Menu
  3  Change Item                     IO= 20 ->Menu    U1= 4 Act#
  4  Delete Item                     IO= 20 ->Menu    U0= 1 Help#
  5  Delete Window                   IO= 20 ->Menu    U0= 1 Help#
  6  Display Cluster Parts List      IO= 20 ->Menu    U1= 4 Act#
  7  Mirror Cluster                  IO= 20 ->Menu    U1= 4 Act#
  8  Save                            IO=148 ->Menu    U1= 5 Act#
  9  Rename Cluster, Then End        IO=148 ->Menu    U1= 1 Act#
 10  End                             IO=148 ->Menu    U1= 2 Act#
 11  Quit, Do Not Save               IO=148 ->Menu    U1= 3 Act#

Help #1
If this option is selected in error, press the
ESC key to return to this menu.

Act #1
0XACTION == 1
IF (1XNEWNAM==1)
THEN CANNOT SELECT

Act #2
0XACTION == 11

Act #3
0XACTION == 21

Act #4
IF (0X000000==0)
THEN CANNOT SELECT

Act #5
0XSAVEME == 1
1XNEWNAM == 0
```

Appendix Page A-4

```
Menu #18

Uflag 1:    1     NSEW:  sub type B
Uflag 2:    1     UNDEFINED

OXCOMPAR == 0

IF (81HEIGHT == 8_HEIGHT)   THEN OXCOMPAR ++ 1
IF (82HEIGHT == 8_HEIGHT)   THEN OXCOMPAR ++ 2

Q Select Next Item To Be Attached To This Frame

1 Carpet Grippers                    IO= 18 ->Menu   U1=  1 Act#
  2 Electrical Items                   IO= 23 ->Menu   U1=  2 Act#
  3 Structural Item On West            IO= 22 ->Menu   U1=  3 Act#
  4 Structural Item On East            IO= 22 ->Menu   U1=  4 Act#
  5 Telephone/Data Symbol              IO= 56 ->Menu   U1=  5 Act#
  6 Tile Face Assembly On North                        U1=  6 Act#
  7 Tile Face Assembly On South                        U1=  7 Act#
  8 Transaction Surface                IO= 58 ->Menu   U1=  8 Act#
  9 Typical Interior On North                          U1=  9 Act#
 10 Typical Interior On South                          U1= 10 Act#
 11 User Commands                      IO= 20 ->Menu   U1= 11 Act#

Act #1
1ACONDES == 25
1ACONCUR == 1
ACTCLOSE == 1
CLOSE0 == 1
IF (0AWIDTH == 30)       THEN 0ALTGEO == 1
IF (0AWIDTH == 36)       THEN 0ALTGEO == 2
IF (0AWIDTH == 42)       THEN 0ALTGEO == 3
IF (0AWIDTH == 48)       THEN 0ALTGEO == 4
IF (CLOSE0==1)
THEN CANNOT SELECT
IF (1XSPACE>>0)
THEN CANNOT SELECT
IF (1AWILDCD==0)
THEN Part #1 G1190.
Part  1: G1190.
ACTOUT == 1

Act #2
OXMEMORY == QCLOSEBA
ACTCLOSE == 1
QCLOSEBA == OXMEMORY
IF (86HEIGHT>>0)
THEN CANNOT SELECT
IF (87HEIGHT>>0)
THEN CANNOT SELECT
IF (QCLOSEBA==15)
THEN CANNOT SELECT
IF (1CPOWER==1)
THEN Goto Menu #202

Act #3
ACTZERO == 1
ACTCLOSE == 1
1ACONDES == 1
IF (81HEIGHT>>0)
THEN CANNOT SELECT

Act #4
ACTZERO == 1
ACTCLOSE == 1
```

Appendix Page A-5

```
1ACONDES == 2
IF (82HEIGHT>>0)
THEN CANNOT SELECT

Act #5
ACTCLOSE == 1

Act #6
ACTCLOSE == 1
1ACONDES == 8
CLOSE3 == 1
1ACONCUR == 6
IF (CLOSE3==1)
THEN CANNOT SELECT

Act #7
ACTCLOSE == 1
1ACONDES == 5
CLOSE4 == 1
1ACONCUR == 6
IF (CLOSE4==1)
THEN CANNOT SELECT

Act #8
ACTCLOSE == 1
1ACONCUR == 1
1ACONDES == 3
CLOSE5 == 1
0XEVENT1 == 0
0XEVENT2 == 0
0XEVENT3 == 0
IF (0AWIDTH  == 24)       THEN 0XEVENT1 ++ 1
IF (21FWIDTH == 36)       THEN 0XEVENT1 ++ 2
IF (22FWIDTH == 36)       THEN 0XEVENT1 ++ 4
IF (0AWIDTH  == 30)       THEN 0XEVENT2 ++ 1
IF (21FWIDTH == 30)       THEN 0XEVENT2 ++ 2
IF (22FWIDTH == 30)       THEN 0XEVENT2 ++ 4
IF (0AWIDTH  == 36)       THEN 0XEVENT3 ++ 1
IF (21FWIDTH == 24)       THEN 0XEVENT3 ++ 2
IF (22FWIDTH == 24)       THEN 0XEVENT3 ++ 4
IF (CLOSE5==1)
THEN CANNOT SELECT
IF (DEFTPCAP==1)
THEN Goto Menu #209
IF (0XEVENT1 == 3)        THEN 0X60TRAN == 1
IF (0XEVENT1 == 5)        THEN 0X60TRAN == 2
IF (0XEVENT1 == 7)        THEN 0X60TRAN == 3
IF (0XEVENT2 == 3)        THEN 0X60TRAN == 1
IF (0XEVENT2 == 5)        THEN 0X60TRAN == 2
IF (0XEVENT2 == 7)        THEN 0X60TRAN == 3
IF (0XEVENT3 == 3)        THEN 0X60TRAN == 1
IF (0XEVENT3 == 5)        THEN 0X60TRAN == 2
IF (0XEVENT3 == 7)        THEN 0X60TRAN == 3
IF (0XCOMPAR == 0)        THEN 0X60TRAN == 0

Act #9
ACTCLOSE == 1
IF (CLOSE7==1)
THEN CANNOT SELECT

Act #10
ACTCLOSE == 1
IF (CLOSE8==1)
THEN CANNOT SELECT

Act #11
```

Appendix Page A-6

```
IF (1XSPACE>>0)
THEN Goto Menu #93
```

Appendix Page A-7

Menu #75

Uflag 2:    1    UNDEFINED

Q Select Next Component To Be Attached To This Phantom Frame

| | | |
|---|---|---|
| 1 Chair Next To Frame | U1= 1 Act# | |
| 2 Coat Bar And Shelf | IO= 76 ->Menu | U1= 2 Act# |
| 3 Lateral File, Freestanding | IO= 77 ->Menu | U1= 3 Act# |
| 4 Lateral File, Suspended | IO= 80 ->Menu | U1= 4 Act# |
| 5 Pedestal, Freestanding | IO=17009 ->Menu | U1= 5 Act# |
| 6 Shelf | IO= 85 ->Menu | U1= 6 Act# |
| 7 Storage Cabinet | IO=17018 ->Menu | U1= 7 Act# |
| 8 Table, Freestanding | U1= 8 Act# | |
| 9 Work Surface | IO=17030 ->Menu | U1= 9 Act# |
| 10 User Commands | IO= 70 ->Menu | |

Act #1
IF (0X000000==0)
THEN CANNOT SELECT

Act #2
0XGOTO == 75
IF (1IWIDTH==36)
THEN CANNOT SELECT
IF (1IWIDTH==42)
THEN CANNOT SELECT
IF (0XCOAT03==0&&0XCOAT06==0&&0XCOAT07==0)
THEN CANNOT SELECT

Act #3
ACTCLOSE == 1
IF (1XFREE27<<30&&1XFREE42<<30&&1XFREE54<<30)
THEN CANNOT SELECT

Act #4
1XDITEM == 16
ACTHIGH == 1
1XHITEM == 14
0XINTIOR == 1
IF (1IWIDTH==36)
THEN CANNOT SELECT
IF (1IWIDTH==42)
THEN CANNOT SELECT
IF (0XSLATOK==0)
THEN CANNOT SELECT

Act #5
IF (1XFREE24<<15&&1XFREE27<<15)
THEN CANNOT SELECT

Act #6
1XDITEM == 14
ACTHIGH == 1
1XHITEM == 8
IF (0XSHLFOK==0)
THEN CANNOT SELECT

Act #7
0XINTIOR == 2
1XDITEM == 14
0ISTRCAB == 1
IF (1XSTORAG == 1)    THEN ACTHIGH == 1
IF (1XSTORAG == 1)    THEN 1XHITEM == 16
IF (1XSTORAG == 0)    THEN 1XHITEM == 16

Appendix Page A-8

```
IF (1XSTORAG == 0)            THEN ACTHIGH == 8_HEIGHT
IF (0XSTOROK==0)
THEN CANNOT SELECT

Act #8
IF (0X000000==0)
THEN CANNOT SELECT

Act #9
0XMEMORY == 4
1XDITEM == 60
ACTFLOOR == 1
0XPENSOK == 1XVERT01
ACTCLOSE == 1
IF (0XWORKOK==0)
THEN CANNOT SELECT
```

Appendix Page A-9

```
Menu #93

Uflag 2:    1    UNDEFINED

0XSAVEME == 0

Q Digitize Working Item Or Make Menu Selection

1 Start New Block Footprint        IO=136 ->Menu   U1=  5 Act#
 2 Start New Cluster                 IO=144 ->Menu   U1=  6 Act#
 3 Work On Block Plan                IO= 93 ->Menu   U1=  7 Act#
 4 Work On Cluster Plan              IO= 93 ->Menu   U1=  8 Act#
 5 -------------------------------   IO= 93 ->Menu   U1=  4 Act#
 6 Change Defaults                   IO= 19 ->Menu   U1= 10 Act#
 7 Delete                            IO=145 ->Menu   U0=  1 Help#
 8 Move                              IO= 93 ->Menu
 9 Rotate                            IO=216 ->Menu
10 -------------------------------   IO= 93 ->Menu   U1=  4 Act#
11 Change Cluster Name/ Desc.        IO= 93 ->Menu   U1=  6 Act#
12 Export To AutoCad                 IO=146 ->Menu
13 Insert Cluster From Project       IO= 93 ->Menu   U1=  6 Act#
14 Make Cluster Set                  IO= 93 ->Menu   U1=  6 Act#
15 Import Building Shell             IO= 93 ->Menu
16 -------------------------------   IO= 93 ->Menu   U1=  4 Act#
17 Save                              IO=148 ->Menu   U1=  9 Act#
18 Save Under New Name, End          IO=148 ->Menu   U1=  1 Act#
19 End                               IO=148 ->Menu   U1=  2 Act#
20 Quit, Do Not Save                 IO=148 ->Menu   U1=  3 Act#

Help #1
If this option is selected in error, press the
ESC key to return to this menu.

Act #1
0XACTION == 3
IF (1XNEWNAM==1)
THEN CANNOT SELECT
IF (0X000000==0)
THEN CANNOT SELECT

Act #2
0XACTION == 13

Act #3
0XACTION == 23

Act #4

Act #5
IF (1XSPACE==1)
THEN CANNOT SELECT
IF (1XSPACE==3)
THEN CANNOT SELECT
```

```
Act #6
IF (1XSPACE==2)
THEN CANNOT SELECT
IF (1XSPACE==4)
THEN CANNOT SELECT

Act #7
1XSPACE = 4
IF (1XSPACE==2)
THEN CANNOT SELECT
IF (1XSPACE==4)
THEN CANNOT SELECT

Act #8
1XSPACE = 3
IF (1XSPACE==1)
THEN CANNOT SELECT
IF (1XSPACE==3)
THEN CANNOT SELECT

Act #9
0XSAVEME = 3
1XNEWNAM = 0
IF (0X000000==0)
THEN CANNOT SELECT

Act #10
IF (1XSCLACT!=1)
THEN CANNOT SELECT
```

Appendix Page A-10

Appendix Page A-11

```
Menu #92

IF (0CPENCAB>>0)
THEN SELECT #4    Peninsula

Q Work Surface Options

1 Corner                    IO=17013 ->Menu  U1=  1 Act#
  2 Corner VDT                IO=17013 ->Menu  U1=  2 Act#
  3 Mitered                   IO=17013 ->Menu  U1=  3 Act#
  4 Peninsula                 IO=149   ->Menu  U1=  4 Act#
  5 Rectangular               IO=17013 ->Menu  U1=  5 Act#

Act #1
0AWORKSF ++ 1
1ACONCUR = 1
1ACONDES = 3
IF (1XVERT13 >> 0)          THEN 1ACONCUR = 3
IF (1XVERT13 >> 0)          THEN 1ACONDES = 4
IF (1XVERT15 >> 0)          THEN 1ACONCUR = 3
IF (1XVERT15 >> 0)          THEN 1ACONDES = 4
IF (1XVERT17 >> 0)          THEN 1ACONCUR = 3
IF (1XVERT17 >> 0)          THEN 1ACONDES = 4
IF (1XVERT19 >> 0)          THEN 1ACONCUR = 3
IF (1XVERT19 >> 0)          THEN 1ACONDES = 4
IF (1IWIDTH==30&&0ADEPTH==30)
THEN CANNOT SELECT
IF (1XVERT12==0&&1XVERT13==0&&1XVERT14==0&&1XVERT15==0&&1XVERT16==0&&1X
THEN CANNOT SELECT
IF (DEFTOPTP=2)
THEN Goto Menu #95

Act #2
0AWORKSF ++ 2
1ACONCUR = 1
1ACONDES = 3
IF (1XVERT19 >> 0)          THEN 1ACONCUR = 3
IF (1XVERT19 >> 0)          THEN 1ACONDES = 4
IF (1XVERT21 >> 0)          THEN 1ACONCUR = 3
IF (1XVERT21 >> 0)          THEN 1ACONDES = 4
IF (0ADEPTH==24&&DEFTOPTP==2)
THEN CANNOT SELECT
```

```
IF (OADEPTH==24&&1XVERT18==0&&1XVERT19==0)
THEN CANNOT SELECT
IF (OADEPTH==30&&1XVERT18==0&&1XVERT19==0&&1XVERT20==0&&1XVERT21==0)
THEN CANNOT SELECT
IF (1IWIDTH==36)
THEN CANNOT SELECT
IF (1IWIDTH==48)
THEN CANNOT SELECT
IF (DEFTOPTP==2)
THEN Goto Menu #96

Act #3
OAWORKSF ++ 3
IF (1XVERT22==0&&1XVERT23==0&&1XVERT24==0&&1XVERT25==0&&1XVERT26==0&&1X
THEN CANNOT SELECT
IF (1XVERT24>>0&&1XVERT25>>0&&1XVERT24==1XVERT25&&1IWIDTH==24)
THEN CANNOT SELECT
IF (1XVERT26>>0&&1XVERT27>>0&&1XVERT26==1XVERT27)
THEN CANNOT SELECT
IF (1XVERT28>>0&&1XVERT29>>0&&1XVERT28==1XVERT29)
THEN CANNOT SELECT
IF (DEFTOPTP==2)
THEN Goto Menu #97
```

Appendix Page A-12

```
Act #4
OAWORKSF ++ 4
1ACONCUR == 1
1ACONDES == 3
IF (OCPENCAB == 1)    THEN 1ACONCUR == 4
IF (OCPENCAB == 1)    THEN 1ACONDES == 4
IF (OCPENCAB == 2)    THEN 1ACONCUR == 5
IF (OCPENCAB == 2)    THEN 1ACONDES == 1
IF (OXPENSOK<<26)
THEN CANNOT SELECT
IF (1IWIDTH==24)
THEN CANNOT SELECT
IF (DEFTOPTP==1)
THEN Goto Menu #107

Act #5
OAWORKSF ++ 5
IF (1XVERT01==0&&1XVERT06==0&&1XVERT07==0&&1XVERT08==0&&1XVERT09==0&&1X
THEN CANNOT SELECT
IF (DEFTOPTP==2)
THEN Goto Menu #98
```

Appendix Page A-13

```
/*      bt_isam.H                                                     */
/*                                                                    */
/*      T_isam ISAM structure initializations                         */

ISEG T_isam_seg[] = (
                ( 2, 2, 8 ),        /* SEGMENT 1   INDEX 1   number */
                ( 4, 2, 8 ),
                ( 2, 2, 8 ),
                ( 6, 2, 8 ),
                ( 2, 2, 8 ),
                ( 8, 1, 1 ),
                ( 2, 2, 8 ),
                ( 9, 1, 1 ),
                ( 2, 2, 8 ),
                ( 10, 2, 8 ),
                ( 2, 2, 8 ),
                ( 12, 2, 8 ),
                ( 2, 2, 8 )
                );

IIDX T_isam_idx[] = (
                ( 2,                /* KEY length   index 1           */
                  0,                /* KEY type     index 1           */
                  0,                /* DUPLICATE flag off             */
                  0,                /* NULL key flag off              */
                  32,               /* EMPTY character                */
                  1,                /* NUMBER of key segments         */
                  &T_isam_seg[0]    /* POINTER to segment array       */
                ),                  /* NULL r-tree index name         */

( 4,                /* KEY length   index 1           */
                  0,                /* KEY type     index 1           */
                  0,                /* DUPLICATE flag off             */
                  0,                /* NULL key flag off              */
                  32,               /* EMPTY character                */
                  2,                /* NUMBER of key segments         */
                  &T_isam_seg[1]    /* POINTER to segment array       */
                ),                  /* NULL r-tree index name         */

( 4,                /* KEY length   index 1           */
                  0,                /* KEY type     index 1           */
                  0,                /* DUPLICATE flag off             */
                  0,                /* NULL key flag off              */
                  32,               /* EMPTY character                */
                  2,                /* NUMBER of key segments         */
                  &T_isam_seg[3]    /* POINTER to segment array       */
                ),                  /* NULL r-tree index name         */

( 3,                /* KEY length   index 1           */
                  0,                /* KEY type     index 1           */
                  0,                /* DUPLICATE flag off             */
                  0,                /* NULL key flag off              */
                  32,               /* EMPTY character                */
                  2,                /* NUMBER of key segments         */
                  &T_isam_seg[5]    /* POINTER to segment array       */
                ),                  /* NULL r-tree index name         */

( 3,                /* KEY length   index 1           */
                  0,                /* KEY type     index 1           */
                  0,                /* DUPLICATE flag off             */
                  0,                /* NULL key flag off              */
                  32,               /* EMPTY character                */
                  2,                /* NUMBER of key segments         */
                  &T_isam_seg[7]    /* POINTER to segment array       */
                ),                  /* NULL r-tree index name         */
```

Appendix Page B-1

```
            ( 4,                 /* KEY length  index 1       */
              0,                 /* KEY type    index 1       */
              0,                 /* DUPLICATE flag off        */
              0,                 /* NULL key flag off         */
             32,                 /* EMPTY character           */
              2,                 /* NUMBER of key segments    */
             &T_isam_seg[9]      /* POINTER to segment array  */
            ),                   /* NULL r-tree index name    */

( 4,                 /* KEY length  index 1       */
              0,                 /* KEY type    index 1       */
              0,                 /* DUPLICATE flag off        */
              0,                 /* NULL key flag off         */
             32,                 /* EMPTY character           */
              2,                 /* NUMBER of key segments    */
             &T_isam_seg[11]     /* POINTER to segment array  */
            )                    /* NULL r-tree index name    */
          };                     /* END of iidx definition    */

IFIL T_isam_dat =   (
            "T_isam", /* root file name               */
               -1,    /* data file number             */
               72,    /* record length                */
              288,    /* file extension size          */
                0,    /* data file mode               */
                7,    /* number of indices            */
              256,    /* index file extension size    */
                0,    /* index file mode              */
        T_isam_idx    /* pointer to index array       */
              );      /* NULL fields                  */
```

Appendix Page B-2

```
/*      BSTRUCT.H                                              */
/*                                                             */
/*      Structures used in the software                        */ struct geo_qs           /* Record in geometry database         */
  (
  COUNT                 delete_flag;
  TEXT                  part[3];
  unsigned char         numvec;
  float                 Fflag[4];
  unsigned char         Uflag[10];
  struct                Fvector_qs vector[MAXCON];    /* vectors */
  );

struct part_qs          /* Records in the part database        */
  (
  COUNT                 delete_flag;
  COUNT                 class[10];
  TEXT                  part[PARTL+1];
  TEXT                  desc[DESCL+1];
  TEXT                  dwg2[3];
  TEXT                  dwg3[3];
  unsigned char         delivery;
  unsigned char         lockplug;
  unsigned char         obsolete;
  unsigned char         gW;
  unsigned char         gH;
  unsigned char         gD;
  unsigned char         numHistory;
  unsigned char         Itype;
  unsigned char         Uflag[4];
  float                 weight;
  float                 volume;
  float                 asytim;
  float                 comyds;
  float                 Fflag[2];
  COUNT                 graphic;
  COUNT                 fixpart;
  COUNT                 actmenu;
  COUNT                 Iflag[4];
  TEXT                  var[30+(10*PART_HISTORYLEN)];
  );
```

```
struct def_qs              /* records in the default database            */
{
  COUNT              delete_flag;
  COUNT              number;
  unsigned char      opt[10][10];
  unsigned char      subopt[10][10];
  unsigned char      CDIused[10];
  unsigned char      Uflag[4];
  TEXT               desc[72];
};

struct DMvar_qs
{
  unsigned char      change;      /* 0=  1+=  2-=  3*=  4/=                      */
  unsigned char      type;        /* which type of var changes                   */
  unsigned char      num;         /* which var number changes                    */
  unsigned char      to_type;     /* type of modifier (0==integer)               */
  unsigned char      to_num;      /* modifier var num or integer value           */
  unsigned char      Uflag;
```

Appendix Page B-3

```
};

struct IF_DMvar_qs
{
  unsigned char      compare;     /* type of comparison                          */
  unsigned char      change;      /* type of change in mod_var                   */
  unsigned char      type;        /* 1st var type                                */
  unsigned char      num;         /* 1st var number                              */
  unsigned char      comp_type;   /* type of comparator (0==integer)             */
  unsigned char      comp_num;    /* comparator var num or integer value         */
  unsigned char      mod_type;    /* type of var to be changed                   */
  unsigned char      mod_num;     /* number of var to be changed                 */
  unsigned char      to_type;     /* type of to_ value (0==integer)              */
  unsigned char      to_num;      /* to_ modifier var num or integer val         */
};

struct IFcon_qs
{
  COUNT              result;      /* if TRUE then return this value              */
  COUNT              useNote;
  unsigned char      numcheck;    /* number of conditions to check               */
  unsigned char      howcheck;    /* how to put together the conditions          */
                                  /*  0 -> && them all together                  */ unsigned char      type[8];
  unsigned char      num[8];
  unsigned char      to_type[8];
  unsigned char      to_num[8];
  unsigned char      compare[8];  /* how to compare them                         */
                                  /*  0   ==   value                             */
  /* NOTE: these last five */    /*  1   !=   value                             */
  /* values are read into  */    /*  2   <<   value                             */
  /* this structure using  */    /*  3   >>   value                             */
  /* the structure IFcon_in */   /*  4   <=   value                             */
  /* which is also used to */    /*  5   >=   value                             */
  /* write out this info   */    /*  6   ==   variable's value                  */
  /* (it has a pad byte to */    /*  7   !=   variable's value                  */
  /* to make an even size) */    /*  8   <<   variable's value                  */
                                  /*  9   >>   variable's value                  */
                                  /* 10   <=   variable's value                  */
                                  /* 11   >=   variable's value                  */
};

struct IFcon_in_qs
{
  unsigned char      compare;
  unsigned char      type;
  unsigned char      num;
  unsigned char      to_type;
  unsigned char      to_num;
  unsigned char      Uflag;
};
```

```
struct MselAct_qs
{
    unsigned char       numDMvar;
    unsigned char       numIF_DMvar;
    unsigned char       numIFnot;
    unsigned char       numIFpart;
    unsigned char       numIFgoto;
    unsigned char       numDMvar2;
    unsigned char       numIF_DMvar2;
    unsigned char       numPart;

unsigned char       numDMvar3;
    unsigned char       Uflag[3];

struct DMvar_qs     A_DMvar         [MAXA_DMvar];
    struct IF_DMvar_qs  A_IF_DMvar      [MAXA_IF_DMvar];
    struct IFcon_qs     A_IFnot         [MAXA_IFnot];
    struct IFcon_qs     A_IFpart        [MAXA_IFpart];
    struct IFcon_qs     A_IFgoto        [MAXA_IFgoto];
    struct DMvar_qs     A_DMvar2        [MAXA_DMvar2];
    struct IF_DMvar_qs  A_IF_DMvar2     [MAXA_IF_DMvar2];
    TEXT                A_part          [MAXA_IFpart][PARTL+1];
    struct DMvar_qs     A_DMvar3        [MAXA_DMvar3];
};

struct menu_qs
{
    COUNT               delete_flag;
    COUNT               number;
    COUNT               useNote;
    COUNT               Iflag[5];
    unsigned char       Uflag[10];
    unsigned char       numSel;
    unsigned char       numHelp;
    unsigned char       numDMvar;
    unsigned char       numIF_DMvar;
    unsigned char       numIFsel;
    unsigned char       numAct;
    unsigned char       Unum[4];

COUNT               SelByte;
    COUNT               HelpByte;
    COUNT               DMvarByte;
    COUNT               IF_DMvarByte;
    COUNT               IFselByte;
    COUNT               ActByte;
    COUNT               Inum[4];
    TEXT                var[MENUVAR];
};

struct CIpoi_qs
{
    COUNT               delete_flag;
    COUNT               Inum;
    COUNT               pnum;
    char                rev;
    unsigned char       z;
    float               x1;
    float               y1;
    COUNT               intdir;
};

struct CIgraph_qs
{
    COUNT               delete_flag;
    COUNT               Inum;
    COUNT               gnum;
    char                rev;
    unsigned char       gW;
    unsigned char       gH;
    unsigned char       gD;
    unsigned char       altgeo;
    unsigned char       Uflag;
    COUNT               graphic;
```

```c
    COUNT           rotZ;
    float           locX;
    float           locY;
    };

struct CIbase_qs
    {
    COUNT           delete_flag;
    COUNT           CInum;
    COUNT           zero;
    char            rev;
    unsigned char   Uflag[3];
    COUNT           DRC_Fail;
    COUNT           numCIpoi;
    COUNT           numCIgraph;
    TEXT            name[10];
    TEXT            desc[38];
    };

struct CItile_qs
    {
    COUNT           delete_flag;
    COUNT           TileSuper;
    COUNT           TileSub;
    char            rev;
    char            lastch;
    unsigned char   opt[10];
    unsigned char   subopt[10];
    };

struct CItileA_qs
    {
    COUNT           delete_flag;
    COUNT           Tnum;
    COUNT           zero;
    char            rev;
    unsigned char   width;
    unsigned char   height;
    unsigned char   frame_ws;
    unsigned char   numtile;
    unsigned char   Gtile[5];
    unsigned char   sup[5];
    unsigned char   sub[5];
    COUNT           graphic[2];
    };

struct Gspace_qs
    {
    COUNT           delete_flag;
    COUNT           number;
    COUNT           Snum;
    COUNT           Citemnum;
    unsigned char   deletable;
    unsigned char   gW;
    unsigned char   gH;
    unsigned char   gD;
    unsigned char   altgeo;
    unsigned char   DrawLay;
    unsigned char   height[4];
    unsigned char   Uflag;
    char            DBAinrev;
    COUNT           DBAin;
```

Appendix Page B-6

```
        COUNT               graphic;
        COUNT               rotZ;
        float               locX;
        float               locY;
        float               locZ;
        rect                gR;
        rect                ggR;
        };

struct Citem_qs             /* cluster design database record          */
        {
        COUNT               delete_flag;
        COUNT               number;
        TEXT                Manu_Line[2];
        TEXT                part[PARTL+1];
        unsigned char       opt[10];
        unsigned char       subopt[10];
        unsigned char       deletable;
        COUNT               orddes;
        COUNT               useKey;
        COUNT               dirconl;
        COUNT               Iflag[5];
        unsigned char       Uflag[10];
        unsigned char       GtileN[5];
        unsigned char       GtileS[5];
        unsigned char       Uvar[MAX_X1A+MAX_X0A+MAX_X1C+MAX_X0C+MAX_XCLOSE+
                                 MAX_XQCLOSE+(MAX_X8_*9)+(MAX_X4_*5)+(MAX_X2_*3)];
        };

struct Iitem_qs             /* Interior design database record         */
        {
        COUNT               delete_flag;
        COUNT               number;
        TEXT                Manu_Line[2];
        TEXT                part[PARTL+1];
        unsigned char       opt[10];
        unsigned char       subopt[10];
        unsigned char       deletable;
        COUNT               orddes;
        COUNT               useKey;
        COUNT               dirconl;
        COUNT               Iflag[5];
        unsigned char       Uflag[10];
        unsigned char       Uvar[MAX_X1A+MAX_X0A+MAX_X1I+MAX_X0I+MAX_XCLOSE+
                                 (MAX_X8_*9)+(MAX_X4_*5)+(MAX_X2_*3)];
        };

struct Titem_qs             /* Tile design database record             */
        {
        COUNT               delete_flag;
        COUNT               number;
        TEXT                Manu_Line[2];
        TEXT                part[PARTL+1];
        unsigned char       opt[10];
        unsigned char       subopt[10];
        unsigned char       Uflag[11];
        COUNT               orddes;
        COUNT               Iflag[5];
        unsigned char       Uvar[MAX_X1A+MAX_X0A+MAX_X1T+MAX_X0T];
        };

struct T_isam_qs
```

Appendix Page B-7

```
    {
    COUNT           delete_flag;
    COUNT           number;
    COUNT           orddes;
    COUNT           destEframe;
    unsigned char   type;
    unsigned char   deletable;
    COUNT           Dframe1;
    COUNT           Dframe2;
    unsigned char   height[4];
    unsigned char   concur;
    unsigned char   condes;
    unsigned char   DrawLay;
    unsigned char   gW;
    unsigned char   gH;
    unsigned char   gD;
    unsigned char   Uflag2;
    unsigned char   nodraw;
    unsigned char   altgeo;
    unsigned char   Uflag;
    char            DBAinrev;
    TEXT            useGeo[3];
    COUNT           Iflag;
    COUNT           DBAin;
    COUNT           graphic;
    COUNT           fixpart;
    COUNT           actmenu;
    COUNT           rotZ;
    float           locX;
    float           locY;
    float           locZ;
    rect            gR;
    rect            ggR;
    };

struct PHframe_qs
    {
    COUNT           delete_flag;
    COUNT           number;
    unsigned char   width;
    unsigned char   height;
    char            used[48][86];
    };

struct PHadj_qs
    {
    COUNT           number;
    COUNT           dist_left;
    COUNT           dist_orthog;
    unsigned char   left;
    unsigned char   orthog;
    unsigned char   width;
    };
```

Appendix Page B-8

```
/*      XINT.C
/*
/*      The functions in this file acts as the Design Manager for the
/*      creation of Interior Typicals.

void DoInterior()
    {
    OpenProjDef();
    upCAD= 0;
    newActive= 0;
    curEframe= 0;
    InFl= 0;
    CADstatus= 0;
    OpenProjCI();
    OpenPHframe();
    ordItem= 0;
    curItem= 1;
    numIframe= 0;
    LeastItem= 1;
    OpenItem();
```

```c
NextMenu= EI_M_INT;
DoNotExitInterior= 1;
AutoIntLoop();

while (DoNotExitInterior)
   {
   QueryCursor((&curP.X),(&curP.Y),&curL,&curB);
   if (KeyEvent(False,&evnt))
      {
      if (evnt.ASCII==0&&evnt.ScanCode==0&&evnt.State>0xff)
         {
         if (evnt.State>0xff&&evnt.State<0x2ff) Mbutton= RIGHTB;
         else Mbutton= LEFTB;
         if (Mbutton==LEFTB)
            {
            if (upCAD==0)
               {
               if (curMsel>-2)
                  {
                  if (curMsel==-1) DisMenu();
                  else
                     {
                     InteriorMenuAction(menu.number,SM[curMsel]);
                     if (DoNotExitInterior) AutoIntLoop();
                     }
                  oldcurP.X-= 1;
                  curMsel= -2;
                  }
               }
            else
               {
               switch(CADstatus)
                  {
                  case 1:
                     if (newActive>0&&newActive!=curActive)
                        {
                        if (0!=GetT_isam(curActive)) err(ERR_XINT,50);
                        DrawT_isam(ON);
                        SetDownCluCAD();
                        upCAD= 0;
                        if (0!=GetT_isam(newActive)) err(ERR_XINT,51);
                        if (0!=GetItem(newActive)) err(ERR_XINT,52);
                        curEframe= T_isam.destEframe;
                        NextMenu= T_isam.actmenu;
                        ZeroZeroVar();
                        RestoreIvar();

SetBelowVar();
                        SetSuspVar(1);
                        SetFreeVar();
                        initIitem();
                        AutoIntLoop();
                        }
                     break;
                  case 2:
                  case 3:
                     if (newActive>0)
                        {
                        SetDownCluCAD();
                        upCAD= 0;
                        InteriorMenuAction(menu.number,-1*CADstatus);
                        if (DoNotExitInterior) AutoIntLoop();
                        }
                     break;
                  }
               }
            }
         }
      }
   if (EqualPt(&curP,&oldcurP)==False)
      {
      DupPt(&curP,&oldcurP);
      UpdateUpCAD(curc);
      if (upCAD) MoveInUpCAD();
      else curc= MoveInMenu();
      }
```

Appendix Page B-9

```
    )
    ClearCadPort();
    KillPHframe();
    CloseProjDef();
    CloseProjCI();
    } void AutoIntLoop()
    {
    COUNT   didF5;
    LoadMenu(NextMenu);
    while (DoNotExitInterior&&AutoSelect>-1)
       {
       InteriorMenuAction(menu.number,AutoSelect);
       if (DoNotExitInterior) LoadMenu(NextMenu);
       }
    if (DoNotExitInterior) DisMenu();
    while(DoNotExitInterior&&CADstatus>3)
       {
       if (X1var[x1XELEVAT]==0)
          {
          DoF5();
          didF5= 1;
          }
       else didF5= 0;
       A0var[x0AINTGER]= GetInteriorDig();
       InteriorMenuAction(menu.number,-1);
       if (DoNotExitInterior) LoadMenu(NextMenu);
       while (DoNotExitInterior&&AutoSelect>-1)
          {
          InteriorMenuAction(menu.number,AutoSelect);
          if (DoNotExitInterior) LoadMenu(NextMenu);
          }
       if (DoNotExitInterior) DisMenu();
       if (didF5) doF5();
```

Appendix Page B-10

```
void InteriorMenuAction(COUNT Mnum, COUNT Msel)
    {
    NoCheck= 1;
    if (Msel==-2)
       {
       NextMenu= SI(-1,0);
       A0var[x0ADGQUAD]= newActive;
       }
    else if (Msel==-3)
       {
       NextMenu= SI(-1,0);
       A0var[x0ADGQUAD]= newActive;
       if (0!=GetT_isam(ordItem)) err(ERR_XINT,849);
       if ((T_isam.gR.Xmax-T_isam.gR.Xmin)>(T_isam.gR.Ymax-T_isam.gR.Ymin))
          {
          if (curP.X<T_isam.gR.Xmin) Ca= 0;
          else if (curP.X>T_isam.gR.Xmax) Ca= T_isam.gW;
          else Ca= (curP.X-T_isam.gR.Xmin)/CperI;
          if (T_isam.rotZ==1800) Ca= T_isam.gW-Ca;
          }
       else
          {
          if (curP.Y<T_isam.gR.Ymin) Ca= 0;
          else if (curP.Y>T_isam.gR.Ymax) Ca= T_isam.gW;
          else Ca= (curP.Y-T_isam.gR.Ymin)/CperI;
          if (T_isam.rotZ==2700) Ca= T_isam.gW-Ca;
          }
       A0var[x0AINTGER]= Ca;
       }
    else
       {
       NextMenu= SI(Msel,0);
       switch(Mnum)
          {
```

```
case EI_M_INT_COM:
  switch(Msel)
    {
    case 0:
      if (0!=GetT_isam(ordItem)) err(ERR_XINT,77);
      if (0!=GetItem(ordItem)) err(ERR_XINT,78);
      curEframe= T_isam.destEframe;
      NextMenu= T_isam.actmenu;
      RestoreIvar();
      SetBelowVar();
      SetSuspVar(1);
      SetFreeVar();
      initIitem();
      break;
    case 3:
      DeleteIntItem();
      break;
    case 4:
      DeleteIntWindow();
      break;
    }
  break;
default:
  if ((Mnum>18000&&Mnum<19001)||(Mnum>28000&&Mnum<29001))
    {
    Iitem.subopt[curOpt]= Msel;
    }
  else if ((Mnum>15000&&Mnum<17001)||(Mnum>25000&&Mnum<27001))
```

```
        {
        curOpt++;
        LastOptSel= Msel;
        Iitem.opt[curOpt]= Msel;
        if (Debug==2) OutOptNeed();
        }
      break;
    }
  if (NoCheck&&DoNotExitInterior) CheckSelectAct(Msel);

void InteriorMenuEntryAct()
  {
  CADstatus= menu.Uflag[2];
  switch(CADstatus)
    {
    case 1:
      newActive= 0;
      curActive= ordItem;
      break;
    case 2:
    case 3:
      SetUpCADQuadrants();
      break;
    }
  if (menu.Uflag[3]==1) curEframe= 0;
  }
```

```c
/*          XMENU.C                                                        */
/*                                                                         */
/*          Funtion for loading a new menu                                 */ void LoadMenu(COUNT Lnum)
  {
  COUNT         La;
  unsigned char cdioff;

if (Lnum==EI_M_TILE)
    {
    cdioff= Xlvar[xlXCDIOFF];
    if (Onfly==0) initVar();
    Xlvar[xlXCDIOFF]= cdioff;
    if (HaveOpened)
      {
      if (Onfly==0) CloseItem();
      else if (Onfly==1) CloseO_Item();
      }
    } switch(Lnum)
    {
    case 0:   err(ERR_XMENU,6666); break;
    case -1:  LoadCluMenu_Tile(_8var[x8_HEIGHT],A0var[x0AWIDTH],0); break;
    case -2:  LoadCluMenu_Interior(NORTH); break;
    case -3:  LoadCluMenu_Interior(SOUTH); break;
    case -4:  LoadCluMenu_Tile(X0var[x0XVARIES],A0var[x0AWIDTH],1); break;
    case -5:  LoadCluMenu_Interior(WALLSTRIP); break;
    case -10: LoadSpaceMenu(); break;
    case -11: LoadDXFMenu(); break;
    default:
      initmenu();
      cpybuf(targ,&Lnum,2);
      if (0!=GTEREC(MENUNUM,TFRMKEY(MENUNUM,targ),&menu)) err(ERR_XMENU,7);
      if (menu.number!=Lnum) err(ERR_XMENU,8);
      if (0!=REDVREC(MENUDAT,&menu,MENUVAR+MENUBASELEN)) err(ERR_XMENU,9);
      curMpage= 0;
      strcpy(s,&menu.var[20]);
      ToQtxt(s);
      for (La=0; La<MAXSEL; La++) SelByte[La]= 0;
      cpybuf(SelByte,&menu.var[menu.SelByte],2*menu.numSel);

if (WhereAmI!=IS_LOOK)
        {
        for (La=0; La<menu.numSel; La++) Mco[La]= -1;
        if (DoDeltaMco)
          for (La=0; La<curDeltaMco; La++)
            if (deltaMco[La][0]==Lnum)
              Mco[(deltaMco[La][1])]= CoMusedF;
        switch(WhereAmI)
          {
          case IS_TILE:      TileMenuEntryAct();     break;
          case IS_DEFAULT:   DefMenuEntryAct();      break;
          case IS_CLUSTER:   ClusterMenuEntryAct();  break;
          case IS_INTERIOR:  InteriorMenuEntryAct(); break;
          case IS_SPACEPLAN: SpaceMenuEntryAct();    break;
          }
        DoMenuDMvar();
        DoMenuIF_DMvar();
        AutoSelect= DoMenuCDI();
        if (AutoSelect==-1) AutoSelect= DoMenuIFsel();
        if (AutoSelect==-1||Debug==1)
          {
          DoMenuIFnot();
          }
        numMpage= numPhysSel/19;
        if (numPhysSel-(19*numMpage)>0) numMpage++;
        if (numMpage==0) numMpage= 1;
        }
      break;
    }
  }
```

```
/*      XMENUACT.C
 *
 *      Funtions for menu entry actions
 */
void DoDMvar()
  {
  COUNT DMa;
  for (DMa=0; DMa<menu.numDMvar; DMa++)
    {
    cpybuf(&DMvar,&menu.var[menu.DMvarByte+(6*DMa)],6);
    DoDMvar();
    CheckActionVar();
    }
  } void DoMenuIF_DMvar()
  {
  COUNT DMa;
  for (DMa=0; DMa<menu.numIF_DMvar; DMa++)
    {
    cpybuf(&IF_DMvar,&menu.var[menu.IF_DMvarByte+(10*DMa)],10);
    DoIF_DMvar();
    CheckActionVar();
    }
  }

COUNT DoMenuIFsel()
  {
  COUNT  DMa, DMb,
         DMreturn,
         curByte;

DMreturn= -1;
  curByte= menu.IFselByte;
  for (DMa=0; DMa<menu.numIFsel; DMa++)
    {
    cpybuf(&IFcon,&menu.var[curByte],6);   curByte+= 6;
    for (DMb=0; DMb<IFcon.numcheck; DMb++)
       {
       initIFcon_in();
       cpybuf(&IFcon_in,&menu.var[curByte],6);  curByte+= 6;
       IFcon.type[DMb]=     IFcon_in.type;
       IFcon.num[DMb]=      IFcon_in.num;
       IFcon.to_type[DMb]=  IFcon_in.to_type;
       IFcon.to_num[DMb]=   IFcon_in.to_num;
       IFcon.compare[DMb]=  IFcon_in.compare;
       }
    if (DoIFcon())
       {
       DMreturn= IFcon.result;
       DMb= 30000;
       DMa= 30000;
       }
    }
  return(DMreturn);
  } void DoMenuIFnot()
  {
  COUNT  DMa, DMb, DMc;

if (Debug!=1)
     {
```

```
    for (DMa=0; DMa<menu.numSel; DMa++)
      {
      if (SU(DMa,1)>0)
        {
        SetMselAct(SU(DMa,1)-1);
        for (DMb=0; DMb<MselAct.numIFnot; DMb++)
          {
          IFcon= MselAct.A_IFnot[DMb];
          if (DoIFcon()) SM[DMa]= 0;
          }
        }
      }
  DMb= 0;
  DMc= 0;
  numPhysSel= 0;
  for (DMa=0; DMa<menu.numSel; DMa++)
    {
    if (SM[DMa])
      {
      SM[DMc]= DMb;
      DMc++;
      DMb++;
      numPhysSel++;
      }
    else  DMb++;
    }
  } void DoDMvar()
  {
  unsigned char to_val;

switch(DMvar.to_type)
    {
    case 0:     to_val= DMvar.to_num;              break;
    case 1:     to_val= ACTvar[DMvar.to_num];      break;
    case 2:     to_val= CLOSEvar[DMvar.to_num];    break;
    case 3:     to_val= QCLOSEvar[DMvar.to_num];   break;
    case 4:     to_val= DEFvar[DMvar.to_num];      break;
    case 5:     to_val= C0var[DMvar.to_num];       break;
    case 6:     to_val= C1var[DMvar.to_num];       break;
    case 7:     to_val= I0var[DMvar.to_num];       break;
    case 8:     to_val= I1var[DMvar.to_num];       break;
    case 9:     to_val= T0var[DMvar.to_num];       break;
    case 10:    to_val= T1var[DMvar.to_num];       break;
    case 11:    to_val= A0var[DMvar.to_num];       break;
    case 12:    to_val= A1var[DMvar.to_num];       break;
    case 13:    to_val= X0var[DMvar.to_num];       break;
    case 14:    to_val= X1var[DMvar.to_num];       break;
    case 15:    to_val= _8var[DMvar.to_num];       break;
    case 16:    to_val= _4var[DMvar.to_num];       break;
    case 17:    to_val= _2var[DMvar.to_num];       break;
    default:    err(ERR_XMENUACT,206);             break;
    } switch(DMvar.change)
    {
    case 0:
      switch(DMvar.type)
        {
        case 1:    ACTvar[DMvar.num]=     to_val; break;
        case 2:    CLOSEvar[DMvar.num]=   to_val; break;
        case 3:    QCLOSEvar[DMvar.num]=  to_val; break;
        case 4:    DEFvar[DMvar.num]=     to_val; break;
```

Appendix Page B-16

```
            case 5:    C0var[DMvar.num]=         to_val;  break;
            case 6:    C1var[DMvar.num]=         to_val;  break;
            case 7:    I0var[DMvar.num]=         to_val;  break;
            case 8:    I1var[DMvar.num]=         to_val;  break;
            case 9:    T0var[DMvar.num]=         to_val;  break;
            case 10:   T1var[DMvar.num]=         to_val;  break;
            case 11:   A0var[DMvar.num]=         to_val;  break;
            case 12:   A1var[DMvar.num]=         to_val;  break;
            case 13:   X0var[DMvar.num]=         to_val;  break;
            case 14:   X1var[DMvar.num]=         to_val;  break;
            case 15:   _8var[DMvar.num]=         to_val;  break;
            case 16:   _4var[DMvar.num]=         to_val;  break;
            case 17:   _2var[DMvar.num]=         to_val;  break;
            default:   err(ERR_XMENUACT,205);             break;
            )
      break;
   case 1:
      switch(DMvar.type)
         (
            case 1:    ACTvar[DMvar.num]+=       to_val;  break;
            case 2:    CLOSEvar[DMvar.num]+=     to_val;  break;
            case 3:    QCLOSEvar[DMvar.num]+=    to_val;  break;
            case 4:    DEFvar[DMvar.num]+=       to_val;  break;
            case 5:    C0var[DMvar.num]+=        to_val;  break;
            case 6:    C1var[DMvar.num]+=        to_val;  break;
            case 7:    I0var[DMvar.num]+=        to_val;  break;
            case 8:    I1var[DMvar.num]+=        to_val;  break;
            case 9:    T0var[DMvar.num]+=        to_val;  break;
            case 10:   T1var[DMvar.num]+=        to_val;  break;
            case 11:   A0var[DMvar.num]+=        to_val;  break;
            case 12:   A1var[DMvar.num]+=        to_val;  break;
            case 13:   X0var[DMvar.num]+=        to_val;  break;
            case 14:   X1var[DMvar.num]+=        to_val;  break;
            case 15:   _8var[DMvar.num]+=        to_val;  break;
            case 16:   _4var[DMvar.num]+=        to_val;  break;
            case 17:   _2var[DMvar.num]+=        to_val;  break;
            default:   err(ERR_XMENUACT,204);             break;
            )
      break;
   case 2:
      switch(DMvar.type)
         (
            case 1:    ACTvar[DMvar.num]-=       to_val;  break;
            case 2:    CLOSEvar[DMvar.num]-=     to_val;  break;
            case 3:    QCLOSEvar[DMvar.num]-=    to_val;  break;
            case 4:    DEFvar[DMvar.num]-=       to_val;  break;
            case 5:    C0var[DMvar.num]-=        to_val;  break;
            case 6:    C1var[DMvar.num]-=        to_val;  break;
            case 7:    I0var[DMvar.num]-=        to_val;  break;
            case 8:    I1var[DMvar.num]-=        to_val;  break;
            case 9:    T0var[DMvar.num]-=        to_val;  break;
            case 10:   T1var[DMvar.num]-=        to_val;  break;
            case 11:   A0var[DMvar.num]-=        to_val;  break;
            case 12:   A1var[DMvar.num]-=        to_val;  break;
            case 13:   X0var[DMvar.num]-=        to_val;  break;
            case 14:   X1var[DMvar.num]-=        to_val;  break;
            case 15:   _8var[DMvar.num]-=        to_val;  break;
            case 16:   _4var[DMvar.num]-=        to_val;  break;
            case 17:   _2var[DMvar.num]-=        to_val;  break;
            default:   err(ERR_XMENUACT,203);             break;
            )
      break;
   case 3:
      switch(DMvar.type)
         (
            case 1:    ACTvar[DMvar.num]*=       to_val;  break;
```

```c
      case  2:  CLOSEvar[DMvar.num]*=                    to_val;  break;
      case  3:  QCLOSEvar[DMvar.num]*=                   to_val;  break;
      case  4:  DEFvar[DMvar.num]*=                      to_val;  break;
      case  5:  C0var[DMvar.num]*=                       to_val;  break;
      case  6:  C1var[DMvar.num]*=                       to_val;  break;
      case  7:  I0var[DMvar.num]*=                       to_val;  break;
      case  8:  I1var[DMvar.num]*=                       to_val;  break;
      case  9:  T0var[DMvar.num]*=                       to_val;  break;
      case 10:  T1var[DMvar.num]*=                       to_val;  break;
      case 11:   A0var[DMvar.num]*=                      to_val;  break;
      case 12:   A1var[DMvar.num]*=                      to_val;  break;
      case 13:   X0var[DMvar.num]*=                      to_val;  break;
      case 14:   X1var[DMvar.num]*=                      to_val;  break;
      case 15:   _8var[DMvar.num]*=                      to_val;  break;
      case 16:   _4var[DMvar.num]*=                      to_val;  break;
      case 17:   _2var[DMvar.num]*=                      to_val;  break;
      default:  err(ERR_XMENUACT,202);
                                                                  break;
      }
    break;
  case 4:
    switch(DMvar.type)
      {
      case  1:  ACTvar[DMvar.num]/=                      to_val;  break;
      case  2:  CLOSEvar[DMvar.num]/=                    to_val;  break;
      case  3:  QCLOSEvar[DMvar.num]/=                   to_val;  break;
      case  4:  DEFvar[DMvar.num]/=                      to_val;  break;
      case  5:  C0var[DMvar.num]/=                       to_val;  break;
      case  6:  C1var[DMvar.num]/=                       to_val;  break;
      case  7:  I0var[DMvar.num]/=                       to_val;  break;
      case  8:  I1var[DMvar.num]/=                       to_val;  break;
      case  9:  T0var[DMvar.num]/=                       to_val;  break;
      case 10:  T1var[DMvar.num]/=                       to_val;  break;
      case 11:   A0var[DMvar.num]/=                      to_val;  break;
      case 12:   A1var[DMvar.num]/=                      to_val;  break;
      case 13:   X0var[DMvar.num]/=                      to_val;  break;
      case 14:   X1var[DMvar.num]/=                      to_val;  break;
      case 15:   _8var[DMvar.num]/=                      to_val;  break;
      case 16:   _4var[DMvar.num]/=                      to_val;  break;
      case 17:   _2var[DMvar.num]/=                      to_val;  break;
      default:  err(ERR_XMENUACT,201);
                                                                  break;
      }
    break;
  default:
    err(ERR_XMENUACT,208);
    break;
  }
} void DoIF_DMvar()
  {
  COUNT           Da;
  unsigned char   comp_val,
                  val;

Da= 0;
  switch(IF_DMvar.comp_type)
    {
    case 0:  comp_val= IF_DMvar.comp_num;                         break;
    case 1:  comp_val= ACTvar[IF_DMvar.comp_num];                 break;
    case 2:  comp_val= CLOSEvar[IF_DMvar.comp_num];               break;
    case 3:  comp_val= QCLOSEvar[IF_DMvar.comp_num];              break;
    case 4:  comp_val= DEFvar[IF_DMvar.comp_num];                 break;
    case 5:  comp_val= C0var[IF_DMvar.comp_num];                  break;
    case 6:  comp_val= C1var[IF_DMvar.comp_num];                  break;
    case 7:  comp_val= I0var[IF_DMvar.comp_num];                  break;
```

Appendix Page B-18

```
        case 8:    comp_val= I1var[IF_DMvar.comp_num];        break;
        case 9:    comp_val= T0var[IF_DMvar.comp_num];        break;
        case 10:   comp_val= T1var[IF_DMvar.comp_num];        break;
        case 11:   comp_val= A0var[IF_DMvar.comp_num];        break;
        case 12:   comp_val= A1var[IF_DMvar.comp_num];        break;
        case 13:   comp_val= X0var[IF_DMvar.comp_num];        break;
        case 14:   comp_val= X1var[IF_DMvar.comp_num];        break;
        case 15:   comp_val= _8var[IF_DMvar.comp_num];        break;
        case 16:   comp_val= _4var[IF_DMvar.comp_num];        break;
        case 17:   comp_val= _2var[IF_DMvar.comp_num];        break;
        default:   err(ERR_XMENUACT,200);                     break;
        }
    switch(IF_DMvar.type)
        {
        case 1:    val= ACTvar[IF_DMvar.num];                 break;
        case 2:    val= CLOSEvar[IF_DMvar.num];               break;
        case 3:    val= QCLOSEvar[IF_DMvar.num];              break;
        case 4:    val= DEFvar[IF_DMvar.num];                 break;
        case 5:    val= C0var[IF_DMvar.num];                  break;
        case 6:    val= C1var[IF_DMvar.num];                  break;
        case 7:    val= I0var[IF_DMvar.num];                  break;
        case 8:    val= I1var[IF_DMvar.num];                  break;
        case 9:    val= T0var[IF_DMvar.num];                  break;
        case 10:   val= T1var[IF_DMvar.num];                  break;
        case 11:   val= A0var[IF_DMvar.num];                  break;
        case 12:   val= A1var[IF_DMvar.num];                  break;
        case 13:   val= X0var[IF_DMvar.num];                  break;
        case 14:   val= X1var[IF_DMvar.num];                  break;
        case 15:   val= _8var[IF_DMvar.num];                  break;
        case 16:   val= _4var[IF_DMvar.num];                  break;
        case 17:   val= _2var[IF_DMvar.num];                  break;
        default:   err(ERR_XMENUACT,212);                     break;
        }
    switch(IF_DMvar.compare)
        {
        case 0:    if (val==comp_val) Da= 1;    break;
        case 1:    if (val!=comp_val) Da= 1;    break;
        case 2:    if (val<  comp_val) Da= 1;   break;
        case 3:    if (val>  comp_val) Da= 1;   break;
        case 4:    if (val<=comp_val) Da= 1;    break;
        case 5:    if (val>=comp_val) Da= 1;    break;
        default:   err(ERR_XMENUACT,215);       break;
        }
    if (Da)
        {
        DMvar.change=    IF_DMvar.change;
        DMvar.type=      IF_DMvar.mod_type;
        DMvar.num=       IF_DMvar.mod_num;
        DMvar.to_type=   IF_DMvar.to_type;
        DMvar.to_num=    IF_DMvar.to_num;
        DoDMvar();
        }
    }

COUNT DoIFcon()
    {
    COUNT           DIa,
                    DIreturn;
    unsigned char   to_val,
                    val;

DIa= 0;
    DIreturn= 1;
    switch(IFcon.howcheck)
        {
```

Appendix Page B-19

```
case 0:
  while (DIreturn&&DIa<IFcon.numcheck)
  {
    switch(IFcon.to_type[DIa])
    {
      case 0:    to_val= IFcon.to_num[DIa];                      break;
      case 1:    to_val= ACTvar[IFcon.to_num[DIa]];               break;
      case 2:    to_val= CLOSEvar[IFcon.to_num[DIa]];             break;
      case 3:    to_val= QCLOSEvar[IFcon.to_num[DIa]];            break;
      case 4:    to_val= DEFvar[IFcon.to_num[DIa]];               break;
      case 5:    to_val= C0var[IFcon.to_num[DIa]];                break;
      case 6:    to_val= C1var[IFcon.to_num[DIa]];                break;
      case 7:    to_val= I0var[IFcon.to_num[DIa]];                break;
      case 8:    to_val= I1var[IFcon.to_num[DIa]];                break;
      case 9:    to_val= T0var[IFcon.to_num[DIa]];                break;
      case 10:   to_val= T1var[IFcon.to_num[DIa]];                break;
      case 11:   to_val= A0var[IFcon.to_num[DIa]];                break;
      case 12:   to_val= A1var[IFcon.to_num[DIa]];                break;
      case 13:   to_val= X0var[IFcon.to_num[DIa]];                break;
      case 14:   to_val= X1var[IFcon.to_num[DIa]];                break;
      case 15:   to_val= _8var[IFcon.to_num[DIa]];                break;
      case 16:   to_val= _4var[IFcon.to_num[DIa]];                break;
      case 17:   to_val= _2var[IFcon.to_num[DIa]];                break;
      default:   err(ERR_XMENUACT,217);                           break;
    }
    switch(IFcon.type[DIa])
    {
      case 1:    val= ACTvar[IFcon.num[DIa]];                     break;
      case 2:    val= CLOSEvar[IFcon.num[DIa]];                   break;
      case 3:    val= QCLOSEvar[IFcon.num[DIa]];                  break;
      case 4:    val= DEFvar[IFcon.num[DIa]];                     break;
      case 5:    val= C0var[IFcon.num[DIa]];                      break;
      case 6:    val= C1var[IFcon.num[DIa]];                      break;
      case 7:    val= I0var[IFcon.num[DIa]];                      break;
      case 8:    val= I1var[IFcon.num[DIa]];                      break;
      case 9:    val= T0var[IFcon.num[DIa]];                      break;
      case 10:   val= T1var[IFcon.num[DIa]];                      break;
      case 11:   val= A0var[IFcon.num[DIa]];                      break;
      case 12:   val= A1var[IFcon.num[DIa]];                      break;
      case 13:   val= X0var[IFcon.num[DIa]];                      break;
      case 14:   val= X1var[IFcon.num[DIa]];                      break;
      case 15:   val= _8var[IFcon.num[DIa]];                      break;
      case 16:   val= _4var[IFcon.num[DIa]];                      break;
      case 17:   val= _2var[IFcon.num[DIa]];                      break;
      default:   err(ERR_XMENUACT,218);                           break;
    }
    switch(IFcon.compare[DIa])
    {
      case 0:   if (val!=to_val) DIreturn= 0;    break;
      case 1:   if (val==to_val) DIreturn= 0;    break;
      case 2:   if (val>=to_val) DIreturn= 0;    break;
      case 3:   if (val<=to_val) DIreturn= 0;    break;
      case 4:   if (val> to_val) DIreturn= 0;    break;
      case 5:   if (val< to_val) DIreturn= 0;    break;
      default:  err(ERR_XMENUACT,220);           break;
    }
    DIa++;
  }
  break;
  default:
    err(ERR_XMENUACT,216);
    break;
  }
  return(DIreturn);
}
```

Appendix Page B-20

```
/*      XMSELACT.C                                          */
/*                                                          */
/*      Funtions for menu selection actions                 */ void DoActDMvar()
   {
   COUNT  DMa;
   for (DMa=0; DMa<MselAct.numDMvar; DMa++)
      {
      DMvar= MselAct.A_DMvar[DMa];
      DoDMvar();
      CheckActionVar();
      }
   } void DoActIF_DMvar()
   {
   COUNT  DMa;
   for (DMa=0; DMa<MselAct.numIF_DMvar; DMa++)
      {
      IF_DMvar= MselAct.A_IF_DMvar[DMa];
      DoIF_DMvar();
      CheckActionVar();
      }
   } void DoActDMvar2()
   {
   COUNT  DMa;
   for (DMa=0; DMa<MselAct.numDMvar2; DMa++)
      {
      DMvar= MselAct.A_DMvar2[DMa];
      DoDMvar();
      CheckActionVar();
      }
   } void DoActIF_DMvar2()
   {
   COUNT  DMa;
   for (DMa=0; DMa<MselAct.numIF_DMvar2; DMa++)
      {
      IF_DMvar= MselAct.A_IF_DMvar2[DMa];
      DoIF_DMvar();
      CheckActionVar();
      }
   } void DoActIFpart()
   {
   COUNT  DMa, DMb;
   for (DMa=0; DMa<MselAct.numIFpart; DMa++)
      {
      IFcon= MselAct.A_IFpart[DMa];
      if (DoIFcon())
         {
         if (IFpartNoACTout==1) err(ERR_XMSELACT,1111);
         IFpartNoACTout= 1;
         T_added= 0;
         initT_isam();
         switch(WhereAmI)
```

Appendix Page B-21

```
        {
        case IS_INTERIOR:    DoIFpartInterior();    break;
        }
      curOpt= -1;
      DMa= 30000;
      } void DoIFpartInterior()
  {
  Iitem.number=   curItem;
  Iitem.orddes=   ordItem;
  Iitem.Uvar[I_1Ass+x1ACONCUR]= A1var[x1ACONCUR];
  Iitem.Uvar[I_1Ass+x1ACONDES]= A1var[x1ACONDES];
  Iitem.Uvar[I_0Ass+x0ATRANSX]= A0var[x0ATRANSX];
  Iitem.Uvar[I_0Ass+x0ATRANSY]= A0var[x0ATRANSY];
  Iitem.Uvar[I_0Ass+x0ATRANSZ]= A0var[x0ATRANSZ];
  Iitem.Uvar[I_0Ass+x0ANODRAW]= A0var[x0ANODRAW];
  Iitem.Uvar[I_0Ass+x0ALTGEO]=  A0var[x0ALTGEO];
  if (Iitem.number>1)
    {
    Iitem.deletable= 1;
    T_isam.deletable= 1;
    }
  Iitem.Manu_Line[0]= Manu_Line[0];
  Iitem.Manu_Line[1]= Manu_Line[1];
  strcpy(Iitem.part,&MselAct.A_part[IFcon.result][0]);
  T_isam.number=    curItem;
  T_isam.orddes=    ordItem;
  T_isam.concur=    A1var[x1ACONCUR];
  T_isam.condes=    A1var[x1ACONDES];
  T_isam.nodraw=    A0var[x0ANODRAW];
  T_isam.altgeo=    A0var[x0ALTGEO];
  T_isam.height[3]= A0var[x0ATRANSY];
  IntPhysicalIn(NEW);
  curItem++;
  } void DoActIFgoto()
  {
  COUNT  DMa;

for (DMa=0; DMa<MselAct.numIFgoto; DMa++)
    {
    IFcon= MselAct.A_IFgoto[DMa];
    if (DoIFcon())
      {
      NextMenu= IFcon.result;
      DMa= 3000;
      }
    }
  } void CheckSelectAct(COUNT Msel)
  {
  if (SU(Msel,1)>0)
    {
    SetMselAct(SU(Msel,1)-1);
    DoActDMvar();
    DoActIF_DMvar();
    DoActIFpart();
    DoActDMvar2();

DoActIF_DMvar2();
    DoActIFgoto();
    }
  }
```

```
/*      XITEM.C                                                              */
/*                                                                           */
/*      Funtions pertaining to items                                         */ void AddItem(COUNT WhatIn)
  {
  if (IFpartNoACTout==0) err(ERR_XITEM,7777);
  IFpartNoACTout= 0;
  switch(WhereAmI)
    {
    case IS_INTERIOR:
      Ab= 0;
      for (Aa=0; Aa<EI_sX1A; Aa++)    (Iitem.Uvar[Ab]= A1var[Aa];      Ab++;)
      for (Aa=0; Aa<EI_sX0A; Aa++)    (Iitem.Uvar[Ab]= A0var[Aa];      Ab++;)
      for (Aa=0; Aa<EI_sX1I; Aa++)    (Iitem.Uvar[Ab]= I1var[Aa];      Ab++;)
      for (Aa=0; Aa<EI_sX0I; Aa++)    (Iitem.Uvar[Ab]= I0var[Aa];      Ab++;)
      for (Aa=0; Aa<EI_sXCLOSE; Aa++) (Iitem.Uvar[Ab]= CLOSEvar[Aa];   Ab++;)
      for (Aa=0; Aa<EI_sX8I*9; Aa++)  (Iitem.Uvar[Ab]= _8var[Aa];      Ab++;)
      for (Aa=0; Aa<EI_sX4I*5; Aa++)  (Iitem.Uvar[Ab]= _4var[Aa];      Ab++;)
      for (Aa=0; Aa<EI_sX2I*3; Aa++)  (Iitem.Uvar[Ab]= _2var[Aa];      Ab++;)
      if (0!=ADDVREC(ITEMDAT,&Iitem,I_len)) err(ERR_XITEM,140);
      if (0!=GetT_isam(Iitem.number)) err(ERR_XITEM,141);
      T_isam.height[0]= Iitem.Uvar[I_8ss+x81HEIGHT];
      T_isam.height[1]= Iitem.Uvar[I_8ss+x82HEIGHT];
      if (0!=SaveT_isam(OLD)) err(ERR_XITEM,142);
      if (T_isam.graphic==120)
        {
        initPHframe();
        PHframe.number= T_isam.number;
        PHframe.width= T_isam.gW;
        PHframe.height= T_isam.gH;
        if (0!=ADDREC(PHFRAMEDAT,&PHframe)) err(ERR_XITEM,143);
        SetFreeVar();
        }
      if (Iitem.number>LeastItem)
        {
        curorddes= Iitem.orddes;
        curnumber= Iitem.number;
        curconcur= Iitem.Uvar[I_1Ass+x1ACONCUR];
        curcondes= Iitem.Uvar[I_1Ass+x1ACONDES];
        for (Aa=0; Aa<EI_sX8I; Aa++) cur8[Aa]= Iitem.Uvar[I_8ss+(9*Aa)];
        for (Aa=0; Aa<EI_sX4I; Aa++) cur4[Aa]= Iitem.Uvar[I_4ss+(5*Aa)];
        for (Aa=0; Aa<EI_sX2I; Aa++) cur2[Aa]= Iitem.Uvar[I_2ss+(3*Aa)];
        curtype= T_isam.type;
        curgraphic= T_isam.graphic;
        if (T_isam.nodraw==0&&T_isam.height[2]>0)
          {
          UpdatePHframeFromT_isam(NEW,ALL);
          SetBelowVar();
          SetSuspVar(0);
          }
        else if (T_isam.graphic==120)
          {
          NewPHframeInserted();
          }
        if (0!=GetItem(curorddes)) err(ERR_XITEM,144);
        if (0!=GetT_isam(curorddes)) err(ERR_XITEM,145);
        if (curtype!=ACTIVE)
          {
          UpdateIitemCloseVar();
          }
        else
          {
          Iitem.deletable+= 1;
          T_isam.deletable+= 1;
```

```
        )
     for (Aa=0; Aa<EI_sX8I; Aa++) dest8[Aa]= Iitem.Uvar[I_8ss+(9*Aa)];
     for (Aa=0; Aa<EI_sX4I; Aa++) dest4[Aa]= Iitem.Uvar[I_4ss+(5*Aa)];
     for (Aa=0; Aa<EI_sX2I; Aa++) dest2[Aa]= Iitem.Uvar[I_2ss+(3*Aa)];
     if (curcondes<9)
       {
       for (Aa=0; Aa<EI_sX8I; Aa++)
         Iitem.Uvar[I_8ss+(9*Aa)+curcondes]= cur8[Aa];
       }
     if (curcondes<5)
       {
       for (Aa=0; Aa<EI_sX4I; Aa++)
         Iitem.Uvar[I_4ss+(5*Aa)+curcondes]= cur4[Aa];
       }
     if (curcondes<3)
       {
       for (Aa=0; Aa<EI_sX2I; Aa++)
         Iitem.Uvar[I_2ss+(3*Aa)+curcondes]= cur2[Aa];
       T_isam.height[curcondes-1]= cur8[0];
       }
     if (0!=SaveT_isam(OLD)) err(ERR_XITEM,146);
     if (0!=RWTVREC(ITEMDAT,&Iitem,I_len)) err(ERR_XITEM,147);
     if (curtype==ACTIVE)
       {
       if (0!=GetItem(curnumber)) err(ERR_XITEM,148);
       if (0!=GetT_isam(curnumber)) err(ERR_XITEM,149);
       if (curconcur<9)
         {
         for (Aa=0; Aa<EI_sX8I; Aa++)
           {
           Iitem.Uvar[I_8ss+(9*Aa)+curconcur]= dest8[Aa];
           _8var[(9*Aa)+curconcur]= dest8[Aa];
           }
         }
       if (curconcur<5)
         {
         for (Aa=0; Aa<EI_sX4I; Aa++)
           {
           Iitem.Uvar[I_4ss+(5*Aa)+curconcur]= dest4[Aa];
           _4var[(5*Aa)+curconcur]= dest4[Aa];
           }
         }
       if (curconcur<3)
         {
         for (Aa=0; Aa<EI_sX2I; Aa++)
           {
           Iitem.Uvar[I_2ss+(3*Aa)+curconcur]= dest2[Aa];
           _2var[(3*Aa)+curconcur]= dest2[Aa];
           }
         T_isam.height[curconcur-1]= dest8[0];
         }
       if (0!=SaveT_isam(OLD)) err(ERR_XITEM,150);
       if (0!=RWTVREC(ITEMDAT,&Iitem,I_len)) err(ERR_XITEM,151);
       }
     else
       {
       if (0!=GetItem(curorddes)) err(ERR_XITEM,152);
       RestoreIvar();
       if (0!=GetT_isam(curorddes)) err(ERR_XITEM,801);
       SetBelowVar();
       SetSuspVar(1);
       SetFreeVar();
       }
     }
   initIitem();
   break;
```

Appendix Page B-25

```
        )
    } void IntPhysicalIn(COUNT NewOld)
{
/* Physical insertion of an interior item: called from IFpart true in   */
/* XMSELACT.C and when loading an old interior database.                */ invertOld= 0;
invertNew= 0;
BaseDirCon1= 0;
if (0!=GetPart(Iitem.part)) err(ERR_XITEM,80);
if (Debug==2) NewOptNeed();
if (part.dwg2[0]!='\0'&&strncmp("ZZZ",part.dwg2,3)!=0)
    strncpy(T_isam.useGeo,part.dwg2,3);
else strncpy(T_isam.useGeo,part.dwg3,3);
T_isam.graphic= part.graphic;
T_isam.fixpart= part.fixpart;
T_isam.actmenu= part.actmenu;
T_isam.height[2]= part.Itype;
T_isam.gW= part.gW;
T_isam.gH= part.gH;
T_isam.gD= part.gD;
if (T_isam.graphic>100&&T_isam.graphic<=10000) T_isam.type= ACTIVE;
else T_isam.type= NON_ACTIVE;
if (T_isam.graphic==120)
    {
    T_isam.destEframe= T_isam.number;
    numIframe++;
    }
if (T_isam.graphic>119&&T_isam.graphic<123) T_isam.gH= _8var[x8_HEIGHT];

if (NewOld==NEW)
    {
    if (T_isam.type==ACTIVE)
        {
        invertOld= ordItem;
        invertNew= Iitem.number;
        ordItem= Iitem.number;
        }
    } if (T_isam.nodraw==0&&T_isam.useGeo[0]!='\0'&&
    strncmp("ZZZ",T_isam.useGeo,3)!=0)
    {
    if (0!=GetGeo(T_isam.useGeo)) err(ERR_XITEM,81);
    if (fabs(geo.vector[0].X1-geo.vector[0].X2)<.005)
        {
        if (geo.vector[0].Y1>geo.vector[0].Y2) BaseDirCon1= 2700;
        else BaseDirCon1= 900;
        }
    else
        {
        if (geo.vector[0].X1>geo.vector[0].X2) BaseDirCon1= 1800;
        else BaseDirCon1= 0;
        }
    nsx= geo.vector[Iitem.Uvar[I_1Ass+x1ACONCUR]-1].X1-Iitem.Uvar[I_0Ass+x0ATRAN
    nsy= geo.vector[Iitem.Uvar[I_1Ass+x1ACONCUR]-1].Y1-Iitem.Uvar[I_0Ass+x0ATRAN
    nfx= geo.vector[Iitem.Uvar[I_1Ass+x1ACONCUR]-1].X2-Iitem.Uvar[I_0Ass+x0ATRAN
    nfy= geo.vector[Iitem.Uvar[I_1Ass+x1ACONCUR]-1].Y2-Iitem.Uvar[I_0Ass+x0ATRAN
    nz=  geo.vector[Iitem.Uvar[I_1Ass+x1ACONCUR]-1].Z- Iitem.Uvar[I_0Ass+x0ATRAN
    if (Iitem.number>LeastItem)
        {
        if (0!=SaveT_isam(NEW)) err(ERR_XITEM,82);
        if (0!=GetT_isam(Iitem.orddes)) err(ERR_XITEM,83);
```

Appendix Page B-26

```
      ordEframe= T_isam.destEframe;
      if (0!=GetGeo(T_isam.useGeo)) err(ERR_XITEM,84);
      floatpoi.X= geo.vector[Iitem.Uvar[I_1Ass+x1ACONDES]-1].X1;
      floatpoi.Y= geo.vector[Iitem.Uvar[I_1Ass+x1ACONDES]-1].Y1;
      rotfloatpoi(T_isam.rotZ);
      asx= floatpoi.X+T_isam.locX;
      asy= floatpoi.Y+T_isam.locY;
      floatpoi.X= geo.vector[Iitem.Uvar[I_1Ass+x1ACONDES]-1].X2;
      floatpoi.Y= geo.vector[Iitem.Uvar[I_1Ass+x1ACONDES]-1].Y2;
      rotfloatpoi(T_isam.rotZ);
      afx= floatpoi.X+T_isam.locX;
      afy= floatpoi.Y+T_isam.locY;
      az= geo.vector[Iitem.Uvar[I_1Ass+x1ACONDES]-1].Z+T_isam.locZ;
      if (0!=GetT_isam(Iitem.number)) err(ERR_XITEM,85);
      if (T_isam.destEframe==0) T_isam.destEframe= ordEframe;
      }
    else
      {
      asx= -10;
      asy= 0;
      afx= 0;
      afy= 0;
      az= 0;
      }
    rot();
    if (T_isam.number!=LeastItem||NewOld==NEW)
      {
      T_isam.locX= locX;
      T_isam.locY= locY;
      T_isam.locZ= locZ;
      T_isam.rotZ= rotZ;
      }
    else rotZ= T_isam.rotZ;
    if (T_isam.graphic!=0)
      {
      DrawT_isam(UDADD_ON);
      if (XIvar[x1XELEVAT]==1) DupRect(&ggR,&T_isam.ggR);
      else DupRect(&gR,&T_isam.gR);
      T_isam.DrawLay= DrawLay;
      }
    BaseDirCon1+= rotZ;
    if (BaseDirCon1>2700) BaseDirCon1-= 3600;
    if (BaseDirCon1<0) BaseDirCon1+= 3600;
    }
  if (Iitem.number==1) BaseDirCon1= 1800;
  Iitem.dircon1= BaseDirCon1;
  DirConOne= Iitem.dircon1;
  if (0!=SaveT_isam(NEW)) err(ERR_XITEM,86);
  if (T_isam.destEframe==0)
    {
    if (0!=GetT_isam(Iitem.orddes)) err(ERR_XITEM,87);
    ordEframe= T_isam.destEframe;
    if (0!=GetT_isam(Iitem.number)) err(ERR_XITEM,88);
    T_isam.destEframe= ordEframe;
    if (0!=SaveT_isam(OLD)) err(ERR_XITEM,89);
    }
  curEframe= T_isam.destEframe;

if (NewOld==NEW)
    {
    if (invertOld>0)
      {
      if (0!=GetT_isam(invertOld)) err(ERR_XITEM,90);
      DrawT_isam(UD_ON);
      if (0!=GetT_isam(invertNew)) err(ERR_XITEM,91);
      }
```

```
      if (invertNew>1) DrawT_isam(UD_HIGHL);
```

```
/*      XCLU_T.C
/*
/*      Funtions for handling the insertion of an Interior sub-assembly
/*      into a cluster assembly design database.

void LoadCluMenu_Interior(COUNT NorS)
{
  for (La=3001; La<4000; La++)
    {
    if (0==GetCI(La,'A',0))
      {
      curByte= CheckAddToInterMenu(curByte,NorS,0);
      }
    else La= 30000;
    if (numPhysSel==MAXSEL-2) La= 30000;
    }
}

COUNT CheckAddToInterMenu(COUNT curByte, COUNT NorS, COUNT doall)
{
  if (0!=GetT_isam(ordItem)) err(ERR_XCLU_T,200);
  fx1= T_isam.locX;
  fy1= T_isam.locY;
  frotZ= T_isam.rotZ;
  fh= T_isam.gH;
  if (NorS==WALLSTRIP)
    {
    frotZ+= 900;
    if (frotZ>2700) frotZ-= 3600;
    switch(frotZ)
      {
      case 0:     fx1-= 48;  fy1+= 0.25;  break;
      case 900:   fy1-= 48;  fx1-= 0.25;  break;
      case 1800:  fx1+= 48;  fy1-= 0.25;  break;
      case 2700:  fy1+= 48;  fx1+= 0.25;  break;
      default:    err(ERR_XCLU_T,241);
      }
    }
  else
    {
    switch(frotZ)
      {
      case 0:     fx2= fx1+T_isam.gW;  fy2= fy1;             break;
      case 900:   fx2= fx1;            fy2= fy1+T_isam.gW;   break;
      case 1800:  fx2= fx1-T_isam.gW;  fy2= fy1;             break;
      case 2700:  fx2= fx1;            fy2= fy1-T_isam.gW;   break;
      default:    err(ERR_XCLU_T,201);
      }
    }
  for (Ca=0; Ca<5; Ca++)        T_Iarr[Ca]= 0;
  for (Ca=0; Ca<10; Ca++)       T_Uarr[Ca]= 0;
  ret= curByte;
  islegal= 0;
  for (Ca=1; Ca<=CIbase.numCIpoi; Ca++)
    {
    if (0!=GetCI(CIbase.CInum,CIbase.rev,Ca)) err(ERR_XCLU_T,223);
    cpybuf(&PHframe.used[(Ca-1)/7][11*( Ca-1-(7*((Ca-1)/7)) )],&CIpoi.z,11);
    } for (Ca=1; Ca<=CIbase.numCIpoi; Ca++)
    {
    cpybuf(&CIpoi.z,&PHframe.used[(Ca-1)/7][11*( Ca-1-(7*((Ca-1)/7)) )],11);
    if (CIpoi.z<=fh)
      {
```

Appendix Page B-29

```
CIx= CIpoi.x1;
CIy= CIpoi.y1;
if (NorS==SOUTH||NorS==WALLSTRIP) crotZ= CIpoi.intdir-frotZ+900;
else crotZ= CIpoi.intdir-frotZ-900;
if (crotZ<0) crotZ+= 3600;
else if (crotZ>=3600) crotZ-= 3600;
floatpoi.X= fx1;
floatpoi.Y= fy1;
rotfloatpoi(crotZ);
cmoveX= CIx-floatpoi.X;
cmoveY= CIy-floatpoi.Y;
Cb= 1;
if (doall)
  {
  if (1==DoesInterFitCluster(cmoveX,cmoveY,crotZ))
    {
    floatpoi.X= CIx;
    floatpoi.Y= CIy;
    irotZ= 3600-crotZ;
    if (irotZ>=3600) irotZ-=3600;
    rotfloatpoi(irotZ);
    ilocX= fx1-floatpoi.X;
    ilocY= fy1-floatpoi.Y;
    cpybuf(&SSet.var[10*numPhysSel],&ilocX,4);
    cpybuf(&SSet.var[(10*numPhysSel)+4],&ilocY,4);
    cpybuf(&SSet.var[(10*numPhysSel)+8],&irotZ,2);
    numPhysSel++;
    if (numPhysSel>((MAXGLOBALSEL*4)/10)-2) Ca= 20000;
    }
  }
else
  {
  if (1==DoesInterFitCluster(cmoveX,cmoveY,crotZ))
    {
    Ca= 30000;
    Cb= 0;
    }
  }
if (Cb&&NorS!=WALLSTRIP)
  {
  floatpoi.X= fx2;
  floatpoi.Y= fy2;
  rotfloatpoi(crotZ);
  cmoveX= CIx-floatpoi.X;
  cmoveY= CIy-floatpoi.Y;
  if (doall)
    {
    if (1==DoesInterFitCluster(cmoveX,cmoveY,crotZ))
      {
      floatpoi.X= CIx;
      floatpoi.Y= CIy;
      irotZ= 3600-crotZ;
      if (irotZ>=3600) irotZ-=3600;
      rotfloatpoi(irotZ);
      ilocX= fx2-floatpoi.X;
      ilocY= fy2-floatpoi.Y;
      cpybuf(&SSet.var[10*numPhysSel],&ilocX,4);
      cpybuf(&SSet.var[(10*numPhysSel)+4],&ilocY,4);
      cpybuf(&SSet.var[(10*numPhysSel)+8],&irotZ,2);
      numPhysSel++;
      if (numPhysSel>((MAXGLOBALSEL*4)/10)-2) Ca= 20000;
      }
    }
  else
    {
    if (1==DoesInterFitCluster(cmoveX,cmoveY,crotZ)) Ca= 30000;
```

Appendix Page B-30

```c
        }
      }
    }
    if (Ca==30001)
      {
      SelByte[numPhysSel]= ret;
      cpybuf(&menu.var[ret],T_Iarr,10);    ret+= 10;
      cpybuf(&menu.var[ret],T_Uarr,10);    ret+= 10;
      sprintf(s,"%3d%c %s",CIbase.CInum-3000,CIbase.rev,CIbase.name);
      if (s[0]==' ') s[0]= '0';
      if (s[1]==' ') s[1]= '0';
      s[15]= '\0';
      cpybuf(&menu.var[ret],s,15);
      ret+= 20;
      numPhysSel++;
      }
  return(ret);
  }

COUNT DoesInterFitCluster(float cmoveX, float cmoveY, COUNT crotZ)
  {
  COUNT   Ca, Cb,
          match,
          ret;

for (Ca=1; Ca<=CIbase.numCIpoi; Ca++)
    {
    cpybuf(&CIpoi.z,&PHframe.used[(Ca-1)/7][11*( Ca-1-(7*((Ca-1)/7)) )],11);
    match= 0;
    Cb= ACTIVE;
    inittarg();
    cpybuf(targ,&Cb,2);
    if (0==FRSSET(T_ISAMTYP,TFRMKEY(T_ISAMTYP,targ),&T_isam,2))
      {
      if (T_isam.graphic==101||T_isam.graphic==102||T_isam.graphic==108)
        {
        match= T_isamCIpoiFit(cmoveX,cmoveY,crotZ);
        }
      while (match==0&&0==NXTSET(T_ISAMTYP,&T_isam))
        {
        if (T_isam.graphic==101||T_isam.graphic==102||T_isam.graphic==108)
          {
          match= T_isamCIpoiFit(cmoveX,cmoveY,crotZ);
          }
        }
      }
    if (match==0) Ca= 30000;
    }
  if (Ca==30001) ret= 0;
  else ret= 1;
  return(ret);
  }

COUNT T_isamCIpoiFit(float cmoveX, float cmoveY, COUNT crotZ)
  {
  COUNT   ret,
          frotZ,
          rot2;
  float   fx1,
          fx2,
          fy1,
          fy2;
```

Appendix Page B-31

```
ret= 0;
if (CIpoi.z<=T_isam.gH)
{
  floatpoi.X= T_isam.locX;
  floatpoi.Y= T_isam.locY;
  if (T_isam.graphic==108)
  {
     frotZ= T_isam.rotZ+900;
     if (frotZ>2700) frotZ-= 3600;
     switch(frotZ)
        {
          case 0:     floatpoi.X-= 48;  floatpoi.Y+= 0.25;  break;
          case 900:   floatpoi.Y-= 48;  floatpoi.X-= 0.25;  break;
          case 1800:  floatpoi.X+= 48;  floatpoi.Y-= 0.25;  break;
          case 2700:  floatpoi.Y+= 48;  floatpoi.X+= 0.25;  break;
          default:    err(ERR_XCLU_T,251);
        }
  }
  rotfloatpoi(crotZ);
  fx1= floatpoi.X+cmoveX;
  fy1= floatpoi.Y+cmoveY;
  rot2= T_isam.rotZ+crotZ;
  if (rot2>=3600) rot2-= 3600;
  if (fabs(CIpoi.x1-fx1)<FTOL&&fabs(CIpoi.y1-fy1)<FTOL) ret= 1;
  if (ret==0&&T_isam.graphic!=108)
  {
     switch(rot2)
        {
          case 0:     fx2= fx1+T_isam.gW;  fy2= fy1;            break;
          case 900:   fx2= fx1;  fy2= fy1+T_isam.gW;            break;
          case 1800:  fx2= fx1-T_isam.gW;  fy2= fy1;            break;
          case 2700:  fx2= fx1;  fy2= fy1-T_isam.gW;            break;
          default:    err(ERR_XCLU_T,202);                      break;
        }
     if (fabs(CIpoi.x1-fx2)<FTOL&&fabs(CIpoi.y1-fy2)<FTOL) ret= 1;
  }
}
return(ret);
} void CluMenu_InteriorAction(COUNT Snum, COUNT Mnum)
{
  COUNT Ca;
  if (Snum<numPhysSel-1)
  {
     initCitem();
     Ca= atoi(&menu.var[34+(40*Snum)+20])+3000;
     sprintf(s,"I%4d%c",Ca,menu.var[34+(40*Snum)+23]);
     strcpy(&Citem.part[1],s);
     Citem.part[0]= '%';
     T_added= 0;
     IFpartNoACTout= 1;
     initT_isam();
     T_isam.DBAin= Ca;
     T_isam.DBAinrev= menu.var[34+(40*Snum)+23];
     T_isam.type= TYPE_INTERIOR;
     T_isam.graphic= GRAPHIC_INTERIOR;
     if (Mnum==-2) SetT_isamInteriorInfo(Ca,NORTH);
     else if (Mnum==-3) SetT_isamInteriorInfo(Ca,SOUTH);
     else SetT_isamInteriorInfo(Ca,WALLSTRIP);
     DoIFpartCluster(INTERIOR);
     curOpt= -1;
     AddItem(INTERIOR);
  }
```

Appendix Page B-32

```
void SetT_isamInteriorInfo(COUNT Inum, COUNT NorS)
{
COUNT            Sa, Sb, Sc, rz, rz2;
struct T_isam_qs ST_isam;
char             ch;
float            lx, ly, lx2, ly2;

cpybuf(&ST_isam,&T_isam,T_ISAMRECLEN);
if (0!=GetCI(Inum,'A',0)) err(ERR_XCLU_T,206);
numPhysSel= 0;
CheckAddToInterMenu(100,NorS,1);
cpybuf(&T_isam,&ST_isam,T_ISAMRECLEN);
if (numPhysSel==0) err(ERR_XCLU_T,208);
for (Sa=0; Sa<numPhysSel; Sa++)
  {
  cpybuf(&lx,&SSet.var[Sa*10],4);
  cpybuf(&ly,&SSet.var[(Sa*10)+4],4);
  cpybuf(&rz,&SSet.var[(Sa*10)+8],2);
  for (Sb=Sa+1; Sb<numPhysSel; Sb++)
    {
    cpybuf(&lx2,&SSet.var[Sb*10],4);
    cpybuf(&ly2,&SSet.var[(Sb*10)+4],4);
    cpybuf(&rz2,&SSet.var[(Sb*10)+8],2);
    if (fabs(lx-lx2)<FTOL&&fabs(ly-ly2)<FTOL&&rz==rz2)
      {
      for (Sc=Sb; Sc<numPhysSel-1; Sc++)
        {
        cpybuf(&SSet.var[Sc*10],&SSet.var[(Sc+1)*10],4);
        cpybuf(&SSet.var[(Sc*10)+4],&SSet.var[((Sc+1)*10)+4],4);
        cpybuf(&SSet.var[(Sc*10)+8],&SSet.var[((Sc+1)*10)+8],2);
        }
      numPhysSel--;
      }
    }
  }

Sa= 0;
if (numPhysSel==1)
  {
  TempDrawT_isamInterior(Sa,UDADD_ON);
  }
else
  {
  GetPenState(&pState);
  ProtectRect(&mR);
  BackColor(CoMqueB);
  PenColor(CoMqueF);
  MoveTo(5,mtextY*(2));
  DrawString("<SPACE> to cycle thru locs");
  MoveTo(5,mtextY*(3));
  DrawString("<RETURN> to accept");
  ProtectOff();
  SetPenState(&pState);
  ch= 0;
  TempDrawT_isamInterior(Sa,UDADD_ON);
  while(ch!=13)
    {
    ch= getch();
    if (ch==32)
      {
      TempDrawT_isamInterior(Sa,UD_OFF);
      if (Sa<numPhysSel-1) Sa++;
      else Sa= 0;
```

Appendix Page B-33

```
            TempDrawT_isamInterior(Sa,UDADD_ON);
        }
    }
}
    cpybuf(&Citem.GtileN[0],&T_isam.locX,4);
    cpybuf(&Citem.GtileN[4],&T_isam.locY,4);
    cpybuf(&Citem.GtileS[3],&T_isam.rotZ,2);
} void TempDrawT_isamInterior(COUNT num, COUNT mode)
{
    cpybuf(&T_isam.locX,&SSet.var[num*10],4);
    cpybuf(&T_isam.locY,&SSet.var[(num*10)+4],4);
    cpybuf(&T_isam.rotZ,&SSet.var[(num*10)+8],2);
    DrawT_isam(mode);
}
```

Appendix Page B-34

```
/*      XINT_ACT.C                                                      */
/*                                                                      */
/*      Funtions for manipulating and using PHframe records in response */
/*      to non-zero action variables.                                   */ void DoActHigh()
{
    /* This functions is called from XMENU.C when ACTvar[xACTHIGH]>0 in order */
    /* to cause the variables 1XVERT01-1XVERT30 to be set for menu logic.    */
    for (Da=0; Da<30; Da++)
    {
        maxV[Da]= 0;
        defV[Da]= 0;
    }
    if (0!=GetT_isam(curEframe)) err(ERR_XINT_ACT,30);
    SetPHadj();
    SetV0();
    SetV1_6();
    SetV5_6();
    SetV7_8();
    SetV9_10_29();
    SetV11_12();
    SetV13_14();
    SetV15_16();
    SetV17_18();
    SetV19_20();
    if (ACTvar[xACTHIGH]>1)
    {
        X1var[x1XVERT01]= defV[0];      X1var[x1XVERT16]= defV[15];
        X1var[x1XVERT02]= defV[1];      X1var[x1XVERT17]= defV[16];
        X1var[x1XVERT03]= defV[2];      X1var[x1XVERT18]= defV[17];
        X1var[x1XVERT04]= defV[3];      X1var[x1XVERT19]= defV[18];
        X1var[x1XVERT05]= defV[4];      X1var[x1XVERT20]= defV[19];
        X1var[x1XVERT06]= defV[5];      X1var[x1XVERT21]= defV[20];
        X1var[x1XVERT07]= defV[6];      X1var[x1XVERT22]= defV[21];
        X1var[x1XVERT08]= defV[7];      X1var[x1XVERT23]= defV[22];
        X1var[x1XVERT09]= defV[8];      X1var[x1XVERT24]= defV[23];
        X1var[x1XVERT10]= defV[9];      X1var[x1XVERT25]= defV[24];
        X1var[x1XVERT11]= defV[10];     X1var[x1XVERT26]= defV[25];
        X1var[x1XVERT12]= defV[11];     X1var[x1XVERT27]= defV[26];
        X1var[x1XVERT13]= defV[12];     X1var[x1XVERT28]= defV[27];
        X1var[x1XVERT14]= defV[13];     X1var[x1XVERT29]= defV[28];
        X1var[x1XVERT15]= defV[14];
    }
    else
    {
        X1var[x1XVERT01]= maxV[0];      X1var[x1XVERT16]= maxV[15];
        X1var[x1XVERT02]= maxV[1];      X1var[x1XVERT17]= maxV[16];
        X1var[x1XVERT03]= maxV[2];      X1var[x1XVERT18]= maxV[17];
        X1var[x1XVERT04]= maxV[3];      X1var[x1XVERT19]= maxV[18];
        X1var[x1XVERT05]= maxV[4];      X1var[x1XVERT20]= maxV[19];
        X1var[x1XVERT06]= maxV[5];      X1var[x1XVERT21]= maxV[20];
        X1var[x1XVERT07]= maxV[6];      X1var[x1XVERT22]= maxV[21];
        X1var[x1XVERT08]= maxV[7];      X1var[x1XVERT23]= maxV[22];
        X1var[x1XVERT09]= maxV[8];      X1var[x1XVERT24]= maxV[23];
```

```
   X1var[x1XVERT10]= maxV[9];      X1var[x1XVERT25]= maxV[24];
   X1var[x1XVERT11]= maxV[10];     X1var[x1XVERT26]= maxV[25];
   X1var[x1XVERT12]= maxV[11];     X1var[x1XVERT27]= maxV[26];
   X1var[x1XVERT13]= maxV[12];     X1var[x1XVERT28]= maxV[27];
   X1var[x1XVERT14]= maxV[13];     X1var[x1XVERT29]= maxV[28];
   X1var[x1XVERT15]= maxV[14];
   }
}
```

Appendix Page B-35

```
void SetPHacross(COUNT num)
{
  if (0!=GetPHframe(num)) err(ERR_XINT_ACT,35);
  initPHacross();
  UpdatePHacross();
} void initPHacross()
{
  COUNT Ia;
  for (Ia=0; Ia<86; Ia++) PHacross[Ia]= 127;
} void UpdatePHacross()
{
  COUNT Sa, Sb;
  for (Sa=0; Sa<86; Sa++)
    {
    if (Sa<PHframe.height)
      {
      for (Sb=0; Sb<PHframe.width; Sb++)
        if (PHacross[Sa]>PHframe.used[Sb][Sa])
          PHacross[Sa]= PHframe.used[Sb][Sa];
      }
    else PHacross[Sa]= 0;
    }
} unsigned char maxV_PHacross(unsigned char inval)
{
  COUNT         ma, mb, mc;
  unsigned char curV, maxV;
  maxV= 0;
  curV= 0;
  mb= X1var[x1XDITEM];
  for (ma=6; ma<86; ma++)
    {
    mc= PHacross[ma];
    if (mc>=mb) curV++;
    else curV= 0;
    if (curV>maxV) maxV= curV;
    }
  if (X1var[x1XDIGTYP]==inval+1) cpybuf(&PHdig[0],&PHacross[0],86);
  return(maxV);
} unsigned char defV_PHacross()
{
  COUNT         ma, mb, mc;
  unsigned char defV;
  defV= 1;
  mb= X1var[x1XDITEM];
  for (ma=ACTvar[xACTHIGH]-1; ma>ACTvar[xACTHIGH]-1-X1var[x1XHITEM]; ma--)
    {
    mc= PHacross[ma];
    if (ma<6||mc<mb)
      {
      defV= 0;
      break;
      }
    }
  return(defV);
```

Appendix Page B-36

```
void SetV0()

SetPHacross(PHadj[0].number);
  maxV[0]= maxV_PHacross(0);
  defV[0]= defV_PHacross();

void SetV1_6()

switch(PHadj[0].width)

case 24:  maxV[1]= maxV[0];   defV[1]= defV[0];
               if (X1var[x1XDIGTYP]==2) cpybuf(&PHdig[0],&PHacross[0],86);
               break;
     case 30:  maxV[2]= maxV[0];   defV[2]= defV[0];
               if (X1var[x1XDIGTYP]==3) cpybuf(&PHdig[0],&PHacross[0],86);
               break;
     case 36:  maxV[3]= maxV[0];   defV[3]= defV[0];
               if (X1var[x1XDIGTYP]==4) cpybuf(&PHdig[0],&PHacross[0],86);
               break;
     case 42:  maxV[4]= maxV[0];   defV[4]= defV[0];
               if (X1var[x1XDIGTYP]==5) cpybuf(&PHdig[0],&PHacross[0],86);
               SetPHacrossMR(PHadj[0].number,32);
               maxV[21]= maxV_PHacross(21);
               defV[21]= defV_PHacross();
               SetPHacrossML(PHadj[0].number,32);
               maxV[22]= maxV_PHacross(22);
               defV[22]= defV_PHacross();
               break;
     case 48:  maxV[5]= maxV[0];   defV[5]= defV[0];
               maxV[6]= maxV[0];   defV[6]= defV[0];
               if (X1var[x1XDIGTYP]==6||X1var[x1XDIGTYP]==7)
                  cpybuf(&PHdig[0],&PHacross[0],86);
               SetPHacrossMR(PHadj[0].number,32);
               maxV[23]= maxV_PHacross(23);
               defV[23]= defV_PHacross();
               SetPHacrossML(PHadj[0].number,32);
               maxV[24]= maxV_PHacross(24);
               defV[24]= defV_PHacross();
               break;
     default:  err(ERR_XINT_ACT,32);
               break;
     }
  } void SetV5_6()
  {
  COUNT Sa;
  if (PHadj[0].width==24)
     {
     for (Sa=1; Sa<numPHadj; Sa++)
        {
        if (PHadj[Sa].left==1&&PHadj[Sa].orthog==0&&
           PHadj[Sa].dist_left==-24&&PHadj[Sa].width==24)
           {
           HangMatch(5,0,Sa,0,0);
           HangMatch(23,2,Sa,0,0);
           }
        else if (PHadj[Sa].left==2&&PHadj[Sa].orthog==0&&
           PHadj[Sa].dist_left==24&&PHadj[Sa].width==24)
           {
```

Appendix Page B-37

```c
            HangMatch(6,0,Sa,0,0);
            HangMatch(24,1,Sa,0,0);
            }
        }
    }
} void SetV7_8()
{
    COUNT Sa;
    if (PHadj[0].width==24)
    {
        for (Sa=1; Sa<numPHadj; Sa++)
        {
            if (PHadj[Sa].left==1&&PHadj[Sa].orthog==0&&
                PHadj[Sa].dist_left==-36&&PHadj[Sa].width==36)
            {
                HangMatch(7,0,Sa,0,0);
                HangMatch(25,2,Sa,0,0);
            }
            else if (PHadj[Sa].left==2&&PHadj[Sa].orthog==0&&
                PHadj[Sa].dist_left==24&&PHadj[Sa].width==36)
            {
                HangMatch(8,0,Sa,0,0);
                HangMatch(26,1,Sa,0,0);
            }
        }
    }
    else if (PHadj[0].width==36)
    {
        for (Sa=1; Sa<numPHadj; Sa++)
        {
            if (PHadj[Sa].left==1&&PHadj[Sa].orthog==0&&
                PHadj[Sa].dist_left==-24&&PHadj[Sa].width==24)
            {
                HangMatch(7,0,Sa,0,0);
                HangMatch(25,2,Sa,0,0);
            }
            else if (PHadj[Sa].left==2&&PHadj[Sa].orthog==0&&
                PHadj[Sa].dist_left==36&&PHadj[Sa].width==24)
            {
                HangMatch(8,0,Sa,0,0);
                HangMatch(26,1,Sa,0,0);
            }
        }
    }
    else if (PHadj[0].width==30)
    {
        for (Sa=1; Sa<numPHadj; Sa++)
        {
            if (PHadj[Sa].left==1&&PHadj[Sa].orthog==0&&
                PHadj[Sa].dist_left==-30&&PHadj[Sa].width==30)
            {
                HangMatch(7,0,Sa,0,0);
                HangMatch(25,2,Sa,0,0);
            }
            else if (PHadj[Sa].left==2&&PHadj[Sa].orthog==0&&
                PHadj[Sa].dist_left==30&&PHadj[Sa].width==30)
            {
                HangMatch(8,0,Sa,0,0);
                HangMatch(26,1,Sa,0,0);
            }
        }
    }
}
```

Appendix Page B-38

```c
void SetV9_10_29()
{
  Sb= Sc= Sd= Se= Sf= Sg= Sh= Si= Sj= Sk= Sl= Sm= 0;
  for (Sa=1; Sa<numPHadj; Sa++)
  {
    if (PHadj[Sa].left==1&&PHadj[Sa].orthog==0&&
      PHadj[Sa].dist_left==-48&&PHadj[Sa].width==48) Sf= Sa;
    else if (PHadj[Sa].left==2&&PHadj[Sa].orthog==0&&
      PHadj[Sa].dist_left==24&&PHadj[Sa].width==48) Sg= Sa;
    else if (PHadj[Sa].left==1&&PHadj[Sa].orthog==0&&
      PHadj[Sa].dist_left==-24&&PHadj[Sa].width==24) Sb= Sa;
    else if (PHadj[Sa].left==1&&PHadj[Sa].orthog==0&&
      PHadj[Sa].dist_left==-48&&PHadj[Sa].width==24) Sc= Sa;
    else if (PHadj[Sa].left==2&&PHadj[Sa].orthog==0&&
      PHadj[Sa].dist_left==PHadj[0].width&&PHadj[Sa].width==24) Sd= Sa;
    else if (PHadj[Sa].left==2&&PHadj[Sa].orthog==0&&
      PHadj[Sa].dist_left==48&&PHadj[Sa].width==24) Se= Sa;
    else if (PHadj[Sa].left==1&&PHadj[Sa].orthog==0&&
      PHadj[Sa].dist_left==-30&&PHadj[Sa].width==30) Sh= Sa;
    else if (PHadj[Sa].left==2&&PHadj[Sa].orthog==0&&
      PHadj[Sa].dist_left==42&&PHadj[Sa].width==30) Si= Sa;
    else if (PHadj[Sa].left==1&&PHadj[Sa].orthog==0&&
      PHadj[Sa].dist_left==-42&&PHadj[Sa].width==42) Sj= Sa;
    else if (PHadj[Sa].left==2&&PHadj[Sa].orthog==0&&
      PHadj[Sa].dist_left==30&&PHadj[Sa].width==42) Sk= Sa;
    else if (PHadj[Sa].left==1&&PHadj[Sa].orthog==0&&
      PHadj[Sa].dist_left==-36&&PHadj[Sa].width==36) Sl= Sa;
    else if (PHadj[Sa].left==2&&PHadj[Sa].orthog==0&&
      PHadj[Sa].dist_left==36&&PHadj[Sa].width==36) Sm= Sa;
  }
  switch(PHadj[0].width)
  {
    case 24:
      if (Sf>0)
        {
          HangMatch(9,0,Sf,0,0);
          HangMatch(27,2,Sf,0,0);
        }
      if (Sg>0)
        {
          HangMatch(10,0,Sg,0,0);
          HangMatch(28,1,Sg,0,0);
        }
      if (Sb>0&&Sc>0)
        {
          HangMatch(9,0,Sb,Sc,0);
          HangMatch(27,2,Sb,Sc,0);
        }
      if (Sd>0&&Se>0)
        {
          HangMatch(10,0,Sd,Se,0);
          HangMatch(28,1,Sd,Se,0);
        }
      if (Sb>0&&Sd>0)
        {
          HangMatch(29,0,Sb,Sd,0);
        }
      break;
    case 48:
      if (Sb>0)
        {
          HangMatch(9,0,Sb,0,0);
          HangMatch(27,2,Sb,0,0);
        }
```

Appendix Page B-39

```
        if (Sd>0)
          {
          HangMatch(10,0,Sd,0,0);
          HangMatch(28,1,Sd,0,0);
          }
        break;
      case 30:
        if (Sj>0)
          {
          HangMatch(9,0,Sj,0,0);
          HangMatch(27,2,Sj,0,0);
          }
        if (Sk>0)
          {
          HangMatch(10,0,Sk,0,0);
          HangMatch(28,1,Sk,0,0);
          }
        break;
      case 42:
        if (Sh>0)
          {
          HangMatch(9,0,Sh,0,0);
          HangMatch(27,2,Sh,0,0);
          }
        if (Si>0)
          {
          HangMatch(10,0,Si,0,0);
          HangMatch(28,1,Si,0,0);
          }
        break;
      case 36:
        if (Sl>0)
          {
          HangMatch(9,0,Sl,0,0);
          HangMatch(27,2,Sl,0,0);
          }
        if (Sm>0)
          {
          HangMatch(10,0,Sm,0,0);
          HangMatch(28,1,Sm,0,0);
          }
        break;
      }
  } void SetV11_12()
  {
  COUNT Sa;
  if (PHadj[0].width==30)
    {
    for (Sa=1; Sa<numPHadj; Sa++)
      {
      if (PHadj[Sa].left==1&&PHadj[Sa].orthog==1&&PHadj[Sa].dist_left==0&&
        PHadj[Sa].width==30&&PHadj[Sa].dist_orthog==30)
        {
        HangMatch(11,0,Sa,0,0);
        }
      else if (PHadj[Sa].left==2&&PHadj[Sa].orthog==1&&
        PHadj[Sa].dist_left==30&&PHadj[Sa].width==30&&
        PHadj[Sa].dist_orthog==0)
        {
        HangMatch(12,0,Sa,0,0);
        }
      }
    }
```

Appendix Page B-40

```
void SetV13_14()
{
  COUNT Sa;
  if (PHadj[0].width==36)
    {
    for (Sa=1; Sa<numPHadj; Sa++)
      {
      if (PHadj[Sa].left==1&&PHadj[Sa].orthog==1&&PHadj[Sa].dist_left==0&&
        PHadj[Sa].width==36&&PHadj[Sa].dist_orthog==36)
        {
        HangMatch(13,0,Sa,0,0);
        }
      else if (PHadj[Sa].left==2&&PHadj[Sa].orthog==1&&PHadj[Sa].dist_left==36&&
        PHadj[Sa].width==36&&PHadj[Sa].dist_orthog==0)
        {
        HangMatch(14,0,Sa,0,0);
        }
      }
    }
} void SetV15_16()
{
  COUNT Sa;
  if (PHadj[0].width==42)
    {
    for (Sa=1; Sa<numPHadj; Sa++)
      {
      if (PHadj[Sa].left==1&&PHadj[Sa].orthog==1&&PHadj[Sa].dist_left==0&&
        PHadj[Sa].width==42&&PHadj[Sa].dist_orthog==42)
        {
        HangMatch(15,0,Sa,0,0);
        }
      else if (PHadj[Sa].left==2&&PHadj[Sa].orthog==1&&
        PHadj[Sa].dist_left==42&&PHadj[Sa].width==42&&PHadj[Sa].dist_orthog==0)
        {
        HangMatch(16,0,Sa,0,0);
        }
      }
    }
} void SetV17_18()
{
  Sb= Sc= Sd= Se= Sf= Sg= Sh= Si= 0;
  for (Sa=1; Sa<numPHadj; Sa++)
    {
    if (PHadj[Sa].left==1&&PHadj[Sa].orthog==1&&PHadj[Sa].dist_left==0&&
      PHadj[Sa].width==48&&PHadj[Sa].dist_orthog==48) Sf= Sa;
    else if (PHadj[Sa].left==2&&PHadj[Sa].orthog==1&&PHadj[Sa].dist_left==
      PHadj[0].width&&PHadj[Sa].width==48&&PHadj[Sa].dist_orthog==0) Sg= Sa;
    else if (PHadj[Sa].left==1&&PHadj[Sa].orthog==1&&PHadj[Sa].dist_left==0&&
      PHadj[Sa].width==24&&PHadj[Sa].dist_orthog==24) Sb= Sa;
    else if (PHadj[Sa].left==1&&PHadj[Sa].orthog==1&&PHadj[Sa].dist_left==0&&
      PHadj[Sa].width==24&&PHadj[Sa].dist_orthog==48) Sc= Sa;
    else if (PHadj[Sa].left==2&&PHadj[Sa].orthog==1&&PHadj[Sa].dist_left==
      PHadj[0].width&&PHadj[Sa].width==24&&PHadj[Sa].dist_orthog==0) Sd= Sa;
    else if (PHadj[Sa].left==2&&PHadj[Sa].orthog==1&&PHadj[Sa].dist_left==
      PHadj[0].width&&PHadj[Sa].width==24&&PHadj[Sa].dist_orthog==24) Se= Sa;
    else if (PHadj[Sa].left==1&&PHadj[Sa].orthog==0&&PHadj[Sa].dist_left==-24&&
      PHadj[Sa].width==24) Sh= Sa;
```

Appendix Page B-41

```
    else if (PHadj[Sa].left==2&&PHadj[Sa].orthog==0&&PHadj[Sa].dist_left==24&&
      PHadj[Sa].width==24) Si= Sa;

if (PHadj[0].width==48)
      {
      if (Sf>0)          HangMatch(17,0,Sf,0,0);
      if (Sg>0)          HangMatch(18,0,Sg,0,0);
      if (Sb>0&&Sc>0)    HangMatch(17,0,Sb,Sc,0);
      if (Sd>0&&Se>0)    HangMatch(18,0,Sd,Se,0);
      }
    else if (PHadj[0].width==24)
      {
      if (Sh>0&&Sg>0)              HangMatch(18,0,Sh,Sg,0);
      if (Sh>0&&Sd>0&&Se>0)        HangMatch(18,0,Sh,Sd,Se);
      if (Si>0&&Sf>0)              HangMatch(17,0,Si,Sf,0);
      if (Si>0&&Sb>0&&Sc>0)        HangMatch(17,0,Si,Sb,Sc);
      }
    } void SetV19_20()
    {
    Sb= Sc= Sd= Se= Sf= Sg= Sh= Si= Sj= Sk= Sl= Sm= Sn= So= Sp= Sq= Sr= Ss= 0;
    for (Sa=1; Sa<numPHadj; Sa++)
      {
      if (PHadj[Sa].left==1&&PHadj[Sa].orthog==1&&PHadj[Sa].dist_left==0&&
        PHadj[Sa].width==30&&PHadj[Sa].dist_orthog==30) Sb= Sa;
      else if (PHadj[Sa].left==1&&PHadj[Sa].orthog==1&&PHadj[Sa].dist_left==0&&
        PHadj[Sa].width==30&&PHadj[Sa].dist_orthog==60) Sc= Sa;
      else if (PHadj[Sa].left==2&&PHadj[Sa].orthog==1&&
        PHadj[Sa].dist_left==PHadj[0].width&&PHadj[Sa].width==30&&
        PHadj[Sa].dist_orthog==0) Sd= Sa;
      else if (PHadj[Sa].left==2&&PHadj[Sa].orthog==1&&
        PHadj[Sa].dist_left==PHadj[0].width&&PHadj[Sa].width==30&&
        PHadj[Sa].dist_orthog==30) Se= Sa;
      else if (PHadj[Sa].left==1&&PHadj[Sa].orthog==0&&
        PHadj[Sa].dist_left==-30&&PHadj[Sa].width==30) Sf= Sa;
      else if (PHadj[Sa].left==2&&PHadj[Sa].orthog==0&&
        PHadj[Sa].dist_left==30&&PHadj[Sa].width==30) Sg= Sa;
      else if (PHadj[Sa].left==1&&PHadj[Sa].orthog==1&&PHadj[Sa].dist_left==0&&
        PHadj[Sa].width==24&&PHadj[Sa].dist_orthog==24) Sh= Sa;
      else if (PHadj[Sa].left==1&&PHadj[Sa].orthog==1&&PHadj[Sa].dist_left==0&&
        PHadj[Sa].width==24&&PHadj[Sa].dist_orthog==60) Si= Sa;
      else if (PHadj[Sa].left==1&&PHadj[Sa].orthog==1&&PHadj[Sa].dist_left==0&&
        PHadj[Sa].width==36&&PHadj[Sa].dist_orthog==36) Sj= Sa;
      else if (PHadj[Sa].left==1&&PHadj[Sa].orthog==1&&PHadj[Sa].dist_left==0&&
        PHadj[Sa].width==36&&PHadj[Sa].dist_orthog==60) Sk= Sa;
      else if (PHadj[Sa].left==2&&PHadj[Sa].orthog==1&&
        PHadj[Sa].dist_left==PHadj[0].width&&PHadj[Sa].width==24&&
        PHadj[Sa].dist_orthog==0) Sl= Sa;
      else if (PHadj[Sa].left==2&&PHadj[Sa].orthog==1&&
        PHadj[Sa].dist_left==PHadj[0].width&&PHadj[Sa].width==24&&
        PHadj[Sa].dist_orthog==36) Sm= Sa;
      else if (PHadj[Sa].left==2&&PHadj[Sa].orthog==1&&
        PHadj[Sa].dist_left==PHadj[0].width&&PHadj[Sa].width==36&&
        PHadj[Sa].dist_orthog==0) Sn= Sa;
      else if (PHadj[Sa].left==2&&PHadj[Sa].orthog==1&&
        PHadj[Sa].dist_left==PHadj[0].width&&PHadj[Sa].width==36&&
        PHadj[Sa].dist_orthog==24) So= Sa;
      else if (PHadj[Sa].left==1&&PHadj[Sa].orthog==0&&PHadj[Sa].dist_left==-24&&
        PHadj[Sa].width==24) Sp= Sa;
      else if (PHadj[Sa].left==1&&PHadj[Sa].orthog==0&&PHadj[Sa].dist_left==-36&&
        PHadj[Sa].width==36) Sq= Sa;
      else if (PHadj[Sa].left==2&&PHadj[Sa].orthog==0&&PHadj[Sa].dist_left==36&&
        PHadj[Sa].width==24) Sr= Sa;
      else if (PHadj[Sa].left==2&&PHadj[Sa].orthog==0&&PHadj[Sa].dist_left==24&&
```

```
          PHadj[Sa].width==36) Ss= Sa;
     }
  switch(PHadj[0].width)
     {
     case 30:
        if (Sf>0&&Sd>0&&Se>0)    HangMatch(20,0,Sf,Sd,Se);
        if (Sf>0&&Sl>0&&So>0)    HangMatch(20,0,Sf,Sl,So);
        if (Sf>0&&Sn>0&&Sm>0)    HangMatch(20,0,Sf,Sn,Sm);
        if (Sg>0&&Sb>0&&Sc>0)    HangMatch(19,0,Sg,Sb,Sc);
        if (Sg>0&&Sh>0&&Sk>0)    HangMatch(19,0,Sg,Sh,Sk);
        if (Sg>0&&Sj>0&&Si>0)    HangMatch(19,0,Sg,Sj,Si);
        break;
     case 24:
        if (Sq>0&&Sd>0&&Se>0)    HangMatch(20,0,Sq,Sd,Se);
        if (Sq>0&&Sl>0&&So>0)    HangMatch(20,0,Sq,Sl,So);
        if (Sq>0&&Sn>0&&Sm>0)    HangMatch(20,0,Sq,Sn,Sm);
        if (Ss>0&&Sb>0&&Sc>0)    HangMatch(19,0,Ss,Sb,Sc);
        if (Ss>0&&Sh>0&&Sk>0)    HangMatch(19,0,Ss,Sh,Sk);
        if (Ss>0&&Sj>0&&Si>0)    HangMatch(19,0,Ss,Sj,Si);
        break;
     case 36:
        if (Sp>0&&Sd>0&&Se>0)    HangMatch(20,0,Sp,Sd,Se);
        if (Sp>0&&Sl>0&&So>0)    HangMatch(20,0,Sp,Sl,So);
        if (Sp>0&&Sn>0&&Sm>0)    HangMatch(20,0,Sp,Sn,Sm);
        if (Sr>0&&Sb>0&&Sc>0)    HangMatch(19,0,Sr,Sb,Sc);
        if (Sr>0&&Sh>0&&Sk>0)    HangMatch(19,0,Sr,Sh,Sk);
        if (Sr>0&&Sj>0&&Si>0)    HangMatch(19,0,Sr,Sj,Si);
        break;
     }
  } void SetPHacrossML(COUNT num, COUNT farr)
  {
  if (0!=GetPHframe(num)) err(ERR_XINT_ACT,84);
  initPHacross();
  UpdatePHacrossML(farr);
  } void UpdatePHacrossML(COUNT farr)
  {
  COUNT Sa, Sb;
  char oPH;
  for (Sa=0; Sa<86; Sa++)
     {
     if (Sa<PHframe.height)
        {
        for (Sb=0; Sb<PHframe.width; Sb++)
           {
           oPH= PHacross[Sa];
           if (PHacross[Sa]>PHframe.used[Sb][Sa])
              PHacross[Sa]= PHframe.used[Sb][Sa];
           if (Sb<farr&&PHacross[Sa]==-100) PHacross[Sa]= oPH;
           }
        }
     else PHacross[Sa]= 0;
     }
  } void SetPHacrossMR(COUNT num, COUNT farr)
  {
  if (0!=GetPHframe(num)) err(ERR_XINT_ACT,85);
  initPHacross();
  UpdatePHacrossMR(farr);
```

Appendix Page B-43

```c
void UpdatePHacrossMR(COUNT farr)
   {
   COUNT Sa, Sb, Sc;
   char oPH;
   Sc= PHframe.width;
   for (Sa=0; Sa<86; Sa++)
      {
      if (Sa<PHframe.height)
         {
         for (Sb=0; Sb<PHframe.width; Sb++)
            {
            oPH= PHacross[Sa];
            if (PHacross[Sa]>PHframe.used[Sb][Sa])
               PHacross[Sa]= PHframe.used[Sb][Sa];
            if (Sb>Sc-farr&&PHacross[Sa]==-100) PHacross[Sa]= oPH;
            }
         }
      else PHacross[Sa]= 0;
      }
   } void DoActVert1()
   {
   /* This functions is called from XMENU.C when ACTvar[xACTVERT1]>0 in order */
   /* to cause the variable 1XVERT01 to be set for menu logic.                */
   maxV[0]= 0;
   defV[0]= 0;
   if (0!=GetT_isam(curEframe)) err(ERR_XINT_ACT,300);
   initPHadj();
   PHadj[0].number= T_isam.number;
   PHadj[0].width= T_Isam.gW;
   PHadj[0].left= 0;
   PHadj[0].orthog= 0;
   PHadj[0].dist_left= 0;
   PHadj[0].dist_orthog= 0;
   numPHadj= 1;
   SetVert1V0();
   if (ACTvar[xACTVERT1]>1) X1var[x1XVERT01]= defV[0];
   else X1var[x1XVERT01]= maxV[0];
   } void DoActFloor()
   {
   /* This functions is called from XMENU.C when ACTvar[xACTVERT1]>0 in order */
   /* to cause the variable 1XVERT01 to be set for menu logic.                */
   if (0!=GetT_isam(curEframe)) err(ERR_XINT_ACT,301);
   initPHadj();
   PHadj[0].number= T_isam.number;
   PHadj[0].width= T_Isam.gW;
   PHadj[0].left= 0;
   PHadj[0].orthog= 0;
   PHadj[0].dist_left= 0;
   PHadj[0].dist_orthog= 0;
   numPHadj= 1;
   SetPHacross(PHadj[0].number);
   uc= 0;
   Db= X1var[x1XDITEM];
   for (Da=0; Da<PHframe.height; Da++)
      {
      Dc= PHacross[Da];
      if (Dc>=Db) uc++;
```

Appendix Page B-44

```
    else Da= 30000;
    )
  X1var[x1XVERT01]= uc;
} void HangMatch(COUNT type, COUNT set_type, COUNT a, COUNT b, COUNT c)
{
  switch(set_type)
    {
    case 0:  SetPHacross(PHadj[0].number);       break;
    case 1:  SetPHacrossML(PHadj[0].number,32);  break;
    case 2:  SetPHacrossMR(PHadj[0].number,32);  break;
    }
  if (0!=GetPHframe(PHadj[a].number)) err(ERR_XINT_ACT,1000);
  if (PHadj[0].width==24&&set_type>0)
    {
    if (set_type==1) UpdatePHacrossML(8);
    else UpdatePHacrossMR(8);
    }
  else UpdatePHacross();
  if (b!=0)
    {
    if (0!=GetPHframe(PHadj[b].number)) err(ERR_XINT_ACT,1001);
    UpdatePHacross();
    }
  if (c!=0)
    {
    if (0!=GetPHframe(PHadj[c].number)) err(ERR_XINT_ACT,1002);
    UpdatePHacross();
    }
  maxV[type]= maxV_PHacross(type);
  defV[type]= defV_PHacross();
} void SetVert1V0()
{
  COUNT            ma, mb, mc;
  SetPHacross(PHadj[0].number);
  maxV[0]= maxV_PHacross(0);
  defV[0]= 1;
  mb= X1var[x1XDITEM];
  for (ma=ACTvar[xACTVERT1]-1; ma>ACTvar[xACTVERT1]-1-X1var[x1XHITEM]; ma--)
    {
    mc= PHacross[ma];
    if (ma<6||mc<mb)
      {
      defV[0]= 0;
      break;
      }
    }
}
```

Appendix Page B-45

```
/*      XINT_PH.C
/*
/*      Funtions for manipulating and using PHframe records void UpdatePHframeFromT_isam(COUNT NewOld, COUNT Upnum)

/* Uses the current T_isam structure to perform an update to all of the
/* affected PHframe records in the PHframe ISAM file.
DframeUp= 0;
Tnumber=        T_isam.number;
Torddes=        T_isam.orddes;
Tgraphic=       T_isam.graphic;
TdestEframe=    T_isam.destEframe;
TgW=            T_isam.gW;
TgH=            T_isam.gH;
TgD=            T_isam.gD;
TlocZ=          T_isam.locZ;
TItype=         T_isam.height[2];
TtransY=        T_isam.height[3];
if (TItype==2)  TlocZ= TgH;
if (T_isam.graphic>124&&T_isam.graphic<129) Tmiter= 1;
else Tmiter= 0;
Tleft= 0;
switch(TItype)
  {
    case 1:
      if (T_isam.concur==3) Tleft= 1;
      else if (T_isam.concur!=1) err(ERR_XINT_PH,0);
      break;
    case 3:
    case 4:
      while (T_isam.orddes!=T_isam.destEframe)
        {
        if (0!=GetT_isam(T_isam.orddes)) err(ERR_XINT_PH,1);
        }
      if (T_isam.concur==3) Tleft= 1;
      else if (T_isam.concur!=1) err(ERR_XINT_PH,2);
      preEframe_width= T_isam.gW;
      break;
  }
if (Tleft==1&&Tmiter==1) Tmiter= 2;

if (0!=GetT_isam(TdestEframe)) err(ERR_XINT_PH,3);
switch(TItype)
  {
    case 1:
    case 4:
      if (Tleft==0) Tleft_to_left= 0;
      else Tleft_to_left= -1*(TgW-T_isam.gW);
      if (Tleft_to_left>0) err(ERR_XINT_PH,5);
      if (TItype==4&&TgW!=preEframe_width) err(ERR_XINT_PH,6);
      break;
    case 2:
      Tleft_to_left= TtransY;
      break;
    case 3:
      if (Tleft==0) Tleft_to_left= TtransY;
      else Tleft_to_left= (-1*(preEframe_width-T_isam.gW))+TtransY;
      break;
  } if (NewOld==NEW) SetPHadj();
if (NewOld==NEW&&Upnum==ALL)
  {
  switch(TItype)
```

Appendix Page B-46

```
      case 1:
      case 2:
        UpdateT_isamDframe(TgW,TgD,Tleft_to_left,Tnumber,Tleft);
        break;
      case 3:
      case 4:
        if (0!=GetT_isam(Torddes)) err(ERR_XINT_PH,133);
        ordDframe1= T_isam.Dframe1;
        ordDframe2= T_isam.Dframe2;
        DframeUp= 1;
        break;

if (Tgraphic>122&&Tgraphic<129)
      {
      UpdatePHadjPHframes(TgW,2,TgD,TlocZ,Tmiter,Tleft_to_left,Upnum);
      if (Tmiter>0)
         {
         if (Tleft)
            {
            UpdatePHadjPHframes(2,TgH,TgD,TlocZ,Tmiter,Tleft_to_left,Upnum);
            Tleft_to_left+= TgW-TgD;
            UpdatePHadjPHframes(TgD,TgH,TgD,TlocZ,Tmiter,Tleft_to_left,Upnum);
            }
         else
            {
            UpdatePHadjPHframes(TgD,TgH,TgD,TlocZ,Tmiter,Tleft_to_left,Upnum);
            Tleft_to_left+= TgW-2;
            UpdatePHadjPHframes(2,TgH,TgD,TlocZ,Tmiter,Tleft_to_left,Upnum);
            }
         }
      else
         {
         UpdatePHadjPHframes(2,TgH,TgD,TlocZ,Tmiter,Tleft_to_left,Upnum);
         Tleft_to_left+= TgW-2;
         UpdatePHadjPHframes(2,TgH,TgD,TlocZ,Tmiter,Tleft_to_left,Upnum);
         }
      }
   else UpdatePHadjPHframes(TgW,TgH,TgD,TlocZ,Tmiter,Tleft_to_left,Upnum);
   if (0!=GetT_isam(Tnumber)) err(ERR_XINT_PH,100);
   if (DframeUp)
      {
      T_isam.Dframe1= ordDframe1;
      T_isam.Dframe2= ordDframe2;
      if (0!=SaveT_isam(OLD)) err(ERR_XINT_PH,134);
      }
   } void SetPHadj()
   {
   startEframe= T_isam.number;
   initPHadj();
   numPHadj= 0;
   PHadj[0].number= startEframe;
   PHadj[0].width= T_isam.gW;
   PHadj[0].left= 0;
   PHadj[0].orthog= 0;
   PHadj[0].dist_left= 0;
   PHadj[0].dist_orthog= 0;
   numPHadj++;
   PHadjLeft();
   if (0!=GetT_isam(startEframe)) err(ERR_XINT_PH,10);
   PHadjRight();
   }
```

Appendix Page B-47

```
void PHadjLeft()
  {
  COUNT           Pa,
                  LeftIsGood,
                  dist_orthog,
                  dist_left;
  unsigned char   orthog;

orthog= 0;
  dist_left= 0;
  dist_orthog= 0;
  Pa= (MAXPHADJ-1)/2;
  LeftIsGood= 1;
  while(LeftIsGood&&numPHadj<Pa)
    {
    if (GetT_isamLeft())
      {
      switch(T_isam.graphic)
        {
        case 120:
          PHadj[numPHadj].number= T_isam.number;
          PHadj[numPHadj].width= T_Isam.gW;
          PHadj[numPHadj].left= 1;
          if (orthog==0)
            {
            dist_left-= T_isam.gW;
            PHadj[numPHadj].orthog= 0;
            PHadj[numPHadj].dist_left= dist_left;
            PHadj[numPHadj].dist_orthog= 0;
            }
          else
            {
            dist_orthog+= T_isam.gW;
            PHadj[numPHadj].orthog= 1;
            PHadj[numPHadj].dist_left= dist_left;
            PHadj[numPHadj].dist_orthog= dist_orthog;
            }
          numPHadj++;
          break;
        case 122:
          if (orthog==0) dist_left-= 3;
          else dist_orthog+= 3;
          break;
        case 121:
          if (orthog==1||(T_isam.concur==2&&T_isam.condes==2)||
              (T_isam.concur==1&&T_isam.condes==1)) LeftIsGood= 0;
          else orthog= 1;
          break;
        default:
          err(ERR_XINT_PH,11);
          break;
        }
      }
    else LeftIsGood= 0;
    }
  } void PHadjRight()
  {
  COUNT           RightIsGood,
                  dist_orthog,
                  dist_left;
  unsigned char   orthog;
```

Appendix Page B-48

```
    orthog= 0;
    dist_orthog= 0;
    dist_left= T_isam.gW;
    RightIsGood= 1;
    while(RightIsGood&&numPHadj<MAXPHADJ-1)
      {
      if (GetT_isamRight())
        {
        switch(T_isam.graphic)
          {
          case 120:
            PHadj[numPHadj].number= T_isam.number;
            PHadj[numPHadj].width= T_isam.gW;
            PHadj[numPHadj].left= 2;
            if (orthog==0)
              {
              PHadj[numPHadj].orthog= 0;
              PHadj[numPHadj].dist_left= dist_left;
              PHadj[numPHadj].dist_orthog= 0;
              dist_left+= T_isam.gW;
              }
            else
              {
              PHadj[numPHadj].orthog= 1;
              PHadj[numPHadj].dist_left= dist_left;
              PHadj[numPHadj].dist_orthog= dist_orthog;
              dist_orthog+= T_isam.gW;
              }
            numPHadj++;
            break;
          case 122:
            if (orthog==0) dist_left+= 3;
            else dist_orthog+= 3;
            break;
          case 121:
            if (orthog==1||(T_isam.concur==2&&T_isam.condes==2)||
                (T_isam.concur==1&&T_isam.condes==1)) RightIsGood= 0;
            else orthog= 1;
            break;
          default:
            err(ERR_XINT_PH,15);
            break;
          }
        }
      else RightIsGood= 0;
      }
    }

COUNT GetT_isamLeft()
  {
  COUNT   ret,
          OtherSide,
          OrddesSetDir,
          LeftCon;

ret= 1;
  switch(T_isam.graphic)
    {
    case 120:
      if (T_isam.number==LeastItem||T_isam.concur==2)
        {
        OrddesSetDir= 1;
        LeftCon= 1;
        }
```

Appendix Page B-49

```
            else OrddesSetDir= 0;
         break;
      case 121:
         if (T_isam.condes==1)
            {
            OrddesSetDir= 1;
            if (T_isam.concur==1) LeftCon= 2;
            else LeftCon= 1;
            }
         else OrddesSetDir= 0;
         break;
      case 122:
         if (T_isam.condes==1)
            {
            OrddesSetDir= 1;
            if (T_isam.concur==1) LeftCon= 3;
            else LeftCon= 1;
            }
         else OrddesSetDir= 0;
         break;
      default:
         err(ERR_XINT_PH,12);
         break;
      } if (OrddesSetDir)
      {
      OtherSide= 0;
      cpybuf(targ,&T_isam.number,2);
      if (0==FRSSET(T_ISAMORD,TFRMKEY(T_ISAMORD,targ),&old_T_isam,2))
         {
         cpybuf(&T_isam,&old_T_isam,T_ISAMRECLEN);
         if (T_isam.condes==LeftCon&&T_isam.graphic>119&&T_isam.graphic<123)
            OtherSide= T_isam.number;
         else
            {
            while (OtherSide==0&&0==NXTSET(T_ISAMORD,&old_T_isam))
               {
               cpybuf(&T_isam,&old_T_isam,T_ISAMRECLEN);
               if (T_isam.condes==LeftCon&&T_isam.graphic>119&&T_isam.graphic<123)
                  OtherSide= T_isam.number;
               }
            }
         if (OtherSide==0) ret= 0;
         }
      else ret= 0;
      }
   else
      {
      if (0!=GetT_isam(T_isam.orddes)) ret= 0;
      }
   return(ret);
   }

COUNT GetT_isamRight()
   {
   COUNT   ret,
           OtherSide,
           OrddesSetDir,
           RightCon;

ret= 1;
   switch(T_isam.graphic)
      {
      case 120:
```

```
     : (T_isam.number==LeastItem||T_isam.concur==1)

OrddesSetDir= 1;
       RightCon= 2;

else OrddesSetDir= 0;
     break;
   case 121:
     if (T_isam.condes==2)
       {
       OrddesSetDir= 1;
       if (T_isam.concur==1) RightCon= 2;
       else RightCon= 1;
       }
     else OrddesSetDir= 0;
     break;
   case 122:
     if (T_isam.condes==2)
       {
       OrddesSetDir= 1;
       if (T_isam.concur==1) RightCon= 3;
       else RightCon= 1;
       }
     else OrddesSetDir= 0;
     break;
   default:
     err(ERR_XINT_PH,13);
     break;
   } if (OrddesSetDir)
   {
   OtherSide= 0;
   cpybuf(targ,&T_isam.number,2);
   if (0==FRSSET(T_ISAMORD,TFRMKEY(T_ISAMORD,targ),&old_T_isam,2))
     {
     cpybuf(&T_isam,&old_T_isam,T_ISAMRECLEN);
     if (T_isam.condes==RightCon&&T_isam.graphic>119&&T_isam.graphic<123)
       OtherSide= T_isam.number;
     else
       {
       while (OtherSide==0&&0==NXTSET(T_ISAMORD,&old_T_isam))
         {
         cpybuf(&T_isam,&old_T_isam,T_ISAMRECLEN);
         if (T_isam.condes==RightCon&&T_isam.graphic>119&&T_isam.graphic<123)
           OtherSide= T_isam.number;
         }
       }
     if (OtherSide==0) ret= 0;
     }
   else ret= 0;
   }
 else
   {
   if (0!=GetT_isam(T_isam.orddes)) ret= 0;
   }
 return(ret);
 } void UpdatePHadjPHframes(unsigned char gW, unsigned char gH, unsigned char gD,
   unsigned char locZ, unsigned char miter, COUNT left_to_left, COUNT Upnum)
 {
 iT= locZ;
 iB= locZ-gH;
 for (Ua=0; Ua<numPHadj; Ua++)
```

Appendix Page B-51

```
if (Upnum==ALL||Upnum==PHadj[Ua].number)
  {
   if (0!=GetPHframe(PHadj[Ua].number)) err(ERR_XINT_PH,20);
   if (PHadj[Ua].orthog==0)
     {
      iD= 0;
      iM= 0;
      iL= left_to_left-PHadj[Ua].dist_left;
      iR= iL+gW;
     }
   else
     {
      if (PHadj[Ua].left==1)
        {
         iD= left_to_left-PHadj[Ua].dist_left;
         if (miter==1) iM= 1;
         else iM= 0;
         iL= PHadj[Ua].dist_orthog-gD;
         iR= PHadj[Ua].dist_orthog;
        }
      else
        {
         iD= PHadj[Ua].dist_left-left_to_left-gW;
         if (miter==2) iM= 1;
         else iM= 0;
         iL= -1*PHadj[Ua].dist_orthog;
         iR= iL+gD;
        }
     }
   PHw= PHframe.width;
   PHh= PHframe.height;
   if (iL<PHw&&iR>0&&iB<PHh)
     {
      if (iL<0) w_start= 0;
      else w_start= iL;
      if (iR>PHw) w_end= PHw;
      else w_end= iR;
      h_start= iB;
      if (iT>PHh) h_end= PHh;
      else h_end= iT;
      for (Uw=w_start; Uw<w_end; Uw++)
        {
         for (Uh=h_start; Uh<h_end; Uh++)
           {
            if (Uw>=iL&&Uw<iR&&Uh>=iB&&Uh<iT)
              {
               if (iD<6&&iM) PHframe.used[Uw][Uh]= -100;
               else if (iM==0)
                 {
                  if (PHframe.used[Uw][Uh]>iD) PHframe.used[Uw][Uh]= iD;
                 }
              }
           }
        }
      if (0!=RWTREC(PHFRAMEDAT,&PHframe)) err(ERR_XINT_PH,21);
     }
  }
 }
} void NewPHframeInserted()
 {
  if (0!=GetPHframe(T_isam.number)) err(ERR_XINT_PH,399);
  NewPHframe= PHframe.number;
```

```
SetPHadj();
New_numPHadj= numPHadj;
for (Na=0; Na<New_numPHadj; Na++) New_PHadjNumbers[Na]= PHadj[Na].number;
for (Na=1; Na<New_numPHadj; Na++)
  {
  if (0!=GetT_isam(New_PHadjNumbers[Na])) err(ERR_XINT_PH,5000);
  SetPHadj();
  if (0!=FRSREC(T_ISAMNUM,&T_isam)) err(ERR_XINT_PH,5001);
  while (0==NXTREC(T_ISAMNUM,&T_isam))
    {
    if (T_isam.destEframe==New_PHadjNumbers[Na])
      {
      if (T_isam.nodraw==0&&T_isam.height[2]>0)
        UpdatePHframeFromT_isam(OLD,NewPHframe);
      }
    }
  }
} void UpdateT_isamDframe(unsigned char gW, unsigned char gD, COUNT left_to_left,
  COUNT Tnum, COUNT Tleft)
{
if (0!=GetT_isam(Tnum)) err(ERR_XINT_PH,600);
Uc= 0;
for (Ua=1; Ua<numPHadj; Ua++)
  {
  Ub= 0;
  if (PHadj[Ua].orthog==0)
    {
    iL= left_to_left-PHadj[Ua].dist_left;
    iR= iL+gW;
    Ub= 1;
    }
  else
    {
    if (PHadj[Ua].left==1&&Tleft==0&&((T_isam.graphic>128&&
      T_isam.graphic<133)||(T_isam.graphic>141&&T_isam.graphic<146)))
      {
      iL= PHadj[Ua].dist_orthog-gD;
      iR= PHadj[Ua].dist_orthog;
      Ub= 2;
      }
    else if (PHadj[Ua].left==2&&Tleft==1&&((T_isam.graphic>128&&
      T_isam.graphic<133)||(T_isam.graphic>141&&T_isam.graphic<146)))
      {
      iL= -1*PHadj[Ua].dist_orthog;
      iR= iL+gD;
      Ub= 3;
      }
    }
  if (Ub>0)
    {
    PHw= PHadj[Ua].width;
    if (iL<PHw&&iR>0)
      {
      switch(Ub)
        {
        case 1:
          switch(Uc)
            {
            case 0: T_isam.Dframe1= PHadj[Ua].number; break;
            case 1: T_isam.Dframe2= PHadj[Ua].number; break;
            }
          Uc++;
          break;
```

Appendix Page B-53

```
          case 2:
          case 3:  break;
          }
        }
      }
    }
    if (Uc>0)
      if (0!=SaveT_isam(OLD)) err(ERR_XINT_PH,602);
}
```

Appendix Page B-54

```
/*      XINT_WS.C
/*
/*      Funtions for setting worksurface and freestanding variable values
void SetSuspVar(COUNT set)
{
  if (T_isam.graphic>122&&T_isam.graphic<129)
    {
    Tnum= T_isam.number;
    TgD= T_isam.gD;
    TgW= T_isam.gW;
    TlocZ= T_isam.locZ;
    Tconcur= T_isam.concur;
    HdigZ= TlocZ-2;
    if (set)
      {
      if (0!=GetT_isam(T_isam.destEframe)) err(ERR_XINT_WS,0);
      SetPHadj();
      }
    if (Tconcur==3) left_to_left= -1*(TgW-PHadj[0].width);
    else left_to_left= 0;
    for (Sa=0; Sa<HDIGLEN; Sa++) Hdig[Sa]= 0;
    for (Sa=0; Sa<numPHadj; Sa++)
      {
      if (PHadj[Sa].orthog==0)
        {
        Sb= PHadj[Sa].dist_left-left_to_left;
        if (Sb>=0&&Sb<TgW)
          {
          if (0!=GetPHframe(PHadj[Sa].number)) err(ERR_XINT_WS,1);
          for (Sc=0; Sc<PHadj[Sa].width; Sc++)
            {
            Sd= 0;
            for (Se=TlocZ-3; Se>=0; Se--)
              {
              Sf= PHframe.used[Sc][Se];
              if (Sf>=TgD) Sd++;
              else Se= -30000;
              }
            if (Sb+Sc<TgW) Hdig[Sb+Sc]= Sd;
            else Sc= 30000;
            }
          }
        }
      }
    Sa= 0;
    Sb= 0;
    Sc= 0;
    Sd= 0;
    Xlvar[xlXSUSP02]= 0;
    Xlvar[xlXSUSP08]= 0;
    Xlvar[xlXSUSP14]= 0;
    Xlvar[xlXSUSP20]= 0;
    for (Se=0; Se<TgW; Se++)
      {
      if (Hdig[Se]>=2)  Sa++; else Sa= 0;
      if (Hdig[Se]>=8)  Sb++; else Sb= 0;
      if (Hdig[Se]>=14) Sc++; else Sc= 0;
      if (Hdig[Se]>=20) Sd++; else Sd= 0;
      if (Xlvar[xlXSUSP02]<Sa) Xlvar[xlXSUSP02]= Sa;
      if (Xlvar[xlXSUSP08]<Sb) Xlvar[xlXSUSP08]= Sb;
      if (Xlvar[xlXSUSP14]<Sc) Xlvar[xlXSUSP14]= Sc;
      if (Xlvar[xlXSUSP20]<Sd) Xlvar[xlXSUSP20]= Sd;
      }
    if (0!=GetT_isam(Tnum)) err(ERR_XINT_WS,5);
```

Appendix Page B-55

```
void SetFreeVar()
   COUNT          Sa, Sb, Sc, Sd, Se,
                  Tnum;

if (T_isam.graphic==120)
      {
      HdigZ= -1;
      Tnum= T_isam.number;
      SetPHadj();
      for (Sa=0; Sa<HDIGLEN; Sa++) Hdig[Sa]= 0;
      for (Sa=0; Sa<numPHadj; Sa++)
         {
         if (PHadj[Sa].orthog==0&&PHadj[Sa].left!=1)
            {
            Sb= PHadj[Sa].dist_left;
            if (Sb>=0&&Sb<HDIGLEN)
               {
               if (0!=GetPHframe(PHadj[Sa].number)) err(ERR_XINT_WS,6);
               for (Sc=0; Sc<PHadj[Sa].width; Sc++)
                  {
                  Sd= 0;
                  for (Se=0; Se<PHframe.height; Se++)
                     {
                     if (PHframe.used[Sc][Se]>=20) Sd++;
                     else Se= 30000;
                     }
                  if (Sb+Sc<HDIGLEN) Hdig[Sb+Sc]= Sd;
                  else Sc= 30000;
                  }
               }
            }
         }
      Sa= 0;
      Sb= 0;
      Sc= 0;
      Sd= 0;
      Xlvar[x1XFREE24]= 0;
      Xlvar[x1XFREE27]= 0;
      Xlvar[x1XFREE42]= 0;
      Xlvar[x1XFREE54]= 0;
      for (Se=0; Se<HDIGLEN; Se++)
         {
         if (Hdig[Se]>=24)  Sa++;  else Sa= 0;
         if (Hdig[Se]>=27)  Sb++;  else Sb= 0;
         if (Hdig[Se]>=42)  Sc++;  else Sc= 0;
         if (Hdig[Se]>=54)  Sd++;  else Sd= 0;
         if (Xlvar[x1XFREE24]<Sa) Xlvar[x1XFREE24]= Sa;
         if (Xlvar[x1XFREE27]<Sb) Xlvar[x1XFREE27]= Sb;
         if (Xlvar[x1XFREE42]<Sc) Xlvar[x1XFREE42]= Sc;
         if (Xlvar[x1XFREE54]<Sd) Xlvar[x1XFREE54]= Sd;
         }
      if (0!=GetT_isam(Tnum)) err(ERR_XINT_WS,5);
      }
   } void SetBelowVar()
   {
   if (T_isam.height[2]==1)
      {
      DoMe[0]= T_isam.destEframe;
```

```
DoMe[1]= T_isam.Dframe1;
DoMe[2]= T_isam.Dframe2;
maxh= 100;
for (Sa=0; Sa<3; Sa++)
   {
   if (DoMe[Sa]!=0)
      {
      if (0!=GetPHframe(DoMe[Sa])) err(ERR_XINT_WS,50);
      for (Sc=0; Sc<PHframe.width; Sc++)
         {
         Sd= 0;
         for (Se=T_isam.locZ-T_isam.gH-1; Se>=0; Se--)
            {
            Sb= PHframe.used[Sc][Se];
            Sf= T_isam.gD;
            if (Sb>=Sf) Sd++;
            else Se= -30000;
            }
         if (maxh>Sd) maxh= Sd;
         }
      }
   }
Xlvar[x1XVERT01]= maxh;
}
```

Appendix Page B-57

```
/*      XINT_DEL.C                                                      */
/*                                                                      */
/*      Funtion for deleting an item from an interior design database by */
/*      method one.                                                     */ void DeleteInteriorByNumber(COUNT DeleteNumber)
   {
   SSet.numSel= 0;
   Upnum= 0;
   theorddes= 0;
   thecondes= 0;
   thetype= 0;
   nextLeast= 0;
   nextordItem= 0;
   leaveordItem= ordItem;
   canDelete= 1;
   if (0!=GetT_isam(DeleteNumber)) err(ERR_XINT_DEL,43);
   if (T_isam.number==LeastItem)
      {
      canDelete= 0;
      while (canDelete==0&&0==NXTREC(T_ISAMNUM,&T_isam))
         {
         if (T_isam.type==ACTIVE&&((T_isam.graphic==120||T_isam.graphic==121||
            T_isam.graphic==122)||(T_isam.destEframe!=DeleteNumber&&
            T_isam.Dframe1!=DeleteNumber&&T_isam.Dframe2!=DeleteNumber)))
            {
            nextLeast= T_isam.number;
            canDelete= 1;
            }
         }
      if (0!=GetT_isam(DeleteNumber)) err(ERR_XINT_DEL,143);
      }
   if (canDelete)
      {
      if (DeleteNumber==ordItem)
         {
         if (DeleteNumber!=LeastItem) nextordItem= T_isam.orddes;
         else nextordItem= nextLeast;
         leaveordItem= nextordItem;
         }
      thetype= T_isam.type;
      theorddes= T_isam.orddes;
      thegraphic= T_isam.graphic;
      thedestEframe= T_isam.destEframe;
      theDframe1= T_isam.Dframe1;
      theDframe2= T_isam.Dframe2;
      if (0!=GetItem(DeleteNumber)) err(ERR_XINT_DEL,151);
      RestoreIvar();
      thecondes= Iitem.Uvar[I_1Ass+x1ACONDES];
      if (nextLeast>0)
```

```
{
LeastItem= nextLeast;
cpybuf(targ,&T_isam.number,2);
if (0!=FRSSET(T_ISAMORD,TFRMKEY(T_ISAMORD.targ),&old_T_isam,2))
   err(ERR_XINT_DEL,333);
cpybuf(&T_isam,&old_T_isam,T_ISAMRECLEN);
if (T_isam.type!=ACTIVE)
  {
  DCa= 1;
  while(DCa)
    {
    if (0!=NXTSET(T_ISAMORD,&old_T_isam)) err(ERR_XINT_DEL,334);
    cpybuf(&T_isam,&old_T_isam,T_ISAMRECLEN);
    if (T_isam.type==ACTIVE) DCa= 0;
    }
  }
```

Appendix Page B-58

```
if (0!=GetItem(T_isam.number)) err(ERR_XINT_DEL,335);
T_isam.deletable-= 1;
IItem.deletable-= 1;
if (Iitem.Uvar[I_1Ass+x1ACONCUR]<9)
  {
  for (DCa=0; DCa<EI_sX8I; DCa++) Iitem.Uvar[I_8ss+(9*DCa)+
    Iitem.Uvar[I_1Ass+x1ACONCUR]]= 0;
  }
if (Iitem.Uvar[I_1Ass+x1ACONCUR]<5)
  {
  for (DCa=0; DCa<EI_sX4I; DCa++) Iitem.Uvar[I_4ss+(5*DCa)+
    Iitem.Uvar[I_1Ass+x1ACONCUR]]= 0;
  }
if (Iitem.Uvar[I_1Ass+x1ACONCUR]<3)
  {
  for (DCa=0; DCa<EI_sX2I; DCa++) Iitem.Uvar[I_2ss+(3*DCa)+
    Iitem.Uvar[I_1Ass+x1ACONCUR]]= 0;
  T_isam.height[Iitem.Uvar[I_1Ass+x1ACONCUR]-1]= 0;
  }
if (0!=RWTVREC(ITEMDAT,&Iitem,I_len)) err(ERR_XINT_DEL,336);
if (0!=SaveT_isam(OLD)) err(ERR_XINT_DEL,336);
}
else
  {
  if (0!=GetT_isam(theorddes)) err(ERR_XINT_DEL,145);
  if (0!=GetItem(theorddes)) err(ERR_XINT_DEL,146);
  if (thetype==ACTIVE)
    {
    T_isam.deletable-= 1;
    IItem.deletable-= 1;
    }
  else DowndateIitemCloseVar();
  if (thecondes<9)
    {
    for (DCa=0; DCa<EI_sX8I; DCa++) Iitem.Uvar[I_8ss+(9*DCa)+
      thecondes]= 0;
    }
  if (thecondes<5)
    {
    for (DCa=0; DCa<EI_sX4I; DCa++) Iitem.Uvar[I_4ss+(5*DCa)+
      thecondes]= 0;
    }
  if (thecondes<3)
    {
    for (DCa=0; DCa<EI_sX2I; DCa++) Iitem.Uvar[I_2ss+(3*DCa)+
      thecondes]= 0;
    T_isam.height[thecondes-1]= 0;
    }
  if (0!=RWTVREC(ITEMDAT,&Iitem,I_len)) err(ERR_XINT_DEL,489);
  if (0!=SaveT_isam(OLD)) err(ERR_XINT_DEL,490);
  }
```

```
cpybuf(targ,&DeleteNumber,2);
if (0==FRSSET(T_ISAMORD,TFRMKEY(T_ISAMORD,targ),&T_isam,2))
   {
   if (T_isam.type!=ACTIVE)
      {
      KillInteriorT_isam();
      }
   while(0==NXTSET(T_ISAMORD,&T_isam))
      {
      if (T_isam.type!=ACTIVE)
         {
         KillInteriorT_isam();
         }
      }
   }
```

Appendix Page B-59

```
if (thegraphic==120)
   {
   numIframe--;
   cpybuf(targ,&DeleteNumber,2);
   if (0==FRSSET(T_ISAMEFR,TFRMKEY(T_ISAMEFR,targ),&T_isam,2))
      {
      if (T_isam.graphic!=120&&T_isam.graphic!=121&&T_isam.graphic!=122)
         {
         KillInteriorT_isam();
         }
      while(0==NXTSET(T_ISAMEFR,&T_isam))
         {
         if (T_isam.graphic!=120&&T_isam.graphic!=121&&T_isam.graphic!=122)
            {
            KillInteriorT_isam();
            }
         }
      }
   }
if (0!=FRSREC(T_ISAMNUM,&T_isam)) err(ERR_XINT_DEL,4030);
while (0==NXTREC(T_ISAMNUM,&T_isam))
   {
   if (T_isam.Dframe1==DeleteNumber)
      {
      DCa= DeleteDframeT_isam(1,leaveordItem);
      if (DCa>0) leaveordItem= nextordItem= DCa;
      }
   }
if (0!=FRSREC(T_ISAMNUM,&T_isam)) err(ERR_XINT_DEL,4040);
while (0==NXTREC(T_ISAMNUM,&T_isam))
   {
   if (T_isam.Dframe2==DeleteNumber)
      {
      DCa= DeleteDframeT_isam(2,leaveordItem);
      if (DCa>0) leaveordItem= nextordItem= DCa;
      }
   }
if (0!=GetT_isam(DeleteNumber)) err(ERR_XINT_DEL,155);
if (thegraphic==120||thegraphic==121||thegraphic==122)
   {
   if (nextLeast>0) LeastItem= T_isam.number;
   DCa= 1;
   if (GetT_isamLeft())
      {
      if (T_isam.graphic==120)  {Upnum= T_isam.number;  DCa= 0;}
      else if (GetT_isamLeft())
         {
         if (T_isam.graphic!=120) err(ERR_XINT_DEL,720);
         Upnum= T_isam.number;
         DCa= 0;
         }
      }
```

```
if (DCa)
  {
  if (0!=GetT_isam(DeleteNumber)) err(ERR_XINT_DEL,721);
  if (GetT_isamRight())
    {
    if (T_isam.graphic==120)  {Upnum= T_isam.number;  DCa= 0;}
    else If (GetT_isamRight())
      {
      if (T_isam.graphic!=120) err(ERR_XINT_DEL,722);
      Upnum= T_isam.number;
      DCa= 0;
      }
    }
  }
```

Appendix Page B-60

```
  if (nextLeast>0) LeastItem= nextLeast;
  if (0!=GetT_isam(DeleteNumber)) err(ERR_XINT_DEL,724);
  }
else Upnum= thedestEframe;
KillInteriorT_isam();

DCc= 0;
if (nextLeast==0&&theorddes!=leaveordItem)
  {
  if (0!=GetT_isam(theorddes)) err(ERR_XINT_DEL,157);
  DrawT_isam(UD_ON);
  DCc= theorddes;
  }
else if (theorddes==leaveordItem)
  {
  if (0!=GetT_isam(theorddes)) err(ERR_XINT_DEL,2158);
  DrawT_isam(UD_HIGHL);
  DCc= theorddes;
  }
else if (nextordItem>0)
  {
  if (0!=GetT_isam(nextordItem)) err(ERR_XINT_DEL,158);
  DrawT_isam(UD_HIGHL);
  DCc= nextordItem;
  }
if (thedestEframe!=DeleteNumber&&thedestEframe!=theorddes)
  {
  if (0!=GetT_isam(thedestEframe)) err(ERR_XINT_DEL,1040);
  DrawT_isam(UD_ON);
  }
if (theDframe1!=0)
  {
  if (0!=GetT_isam(theDframe1)) err(ERR_XINT_DEL,1041);
  DrawT_isam(UD_ON);
  }
if (theDframe2!=0)
  {
  if (0!=GetT_isam(theDframe2)) err(ERR_XINT_DEL,1042);
  DrawT_isam(UD_ON);
  }
for (DCa=0; DCa<SSet.numSel; DCa++)
  {
  cpybuf(&DCb,&SSet.var[DCa*2],2);
  if (DCb!=DCc)
    {
    if (0!=GetT_isam(DCb)) err(ERR_XINT_DEL,3000);
    DrawT_isam(UD_ON);
    }
  }
```

```
if (thegraphic==120)
{
    for (DCa=0; DCa<numEframe; DCa++)
    {
        if (Eframe[DCa][0]==DeleteNumber)
        {
            for (DCb=DCa; DCb<numEframe-1; DCb++)
            {
                Eframe[DCb][0]= Eframe[DCb+1][0];
                Eframe[DCb][1]= Eframe[DCb+1][1];
                Eframe[DCb][2]= Eframe[DCb+1][2];
            }
            numEframe--;
            DCa= 30000;
        }
    }
}
```

Appendix Page B-61

```
if (Upnum!=0) DeleteIntPHframeUpdate(Upnum);

else err(ERR_XINT_DEL,6600);
crdItem= leaveordItem;
```

Appendix Page B-62

We claim:

1. An expert system for designing a connected collection of components, where each said component can be described by at least one constant characteristic and at least one variable characteristic, said expert system comprising:
 a knowledge base, said knowledge base comprising:
  a first record pertaining to a first connectable component having at least one constant characteristic and also a variable characteristic, where the state of the variable characteristic determines whether or not a second connectable component can be connected to said first connectable component,
  a second record pertaining to said second connectable component, connectable to said first component by an allowed connection determined by the state of the variable characteristic of said first record, and
  a rule for connecting said first connectable component and said second connectable component, said rule including a test for said variable characteristic of said first record;
 an inference engine, said inference engine comprising:
  means for selecting said first record for said first component,
  means for testing the state of said variable characteristic of said first record and determining whether said first and second components can be connected,
  means for selecting said second record for said second component if said connection is allowed,
  means for selecting said allowed connection between the first and the second connectable components to form a connected collection; and
  means for storing information about said connected collection.

2. The expert system of claim 1, wherein said means for storing information stores information in a design database made of records, said means for storing information further comprising
 means for identifying each component in said connected collection,
 means for storing information about each component and how it is connected to a next connected component to form a component pair,
 means for recording linkages between components of said component pair,
 means for identifying the component to which each respective component is linked in said component pair, and
 means for recording the geometric relationship between each component of said component pair.

3. The expert system of claim 2, including means for selecting a component from said connected collection and designating it an active component;
 means for selectively deleting said active component;
 means for selectively modifying said active component;
 means for adding and connecting a third connectable component to said active component.

4. The expert system of claim 3 further comprising
 means to display a menu as a visual display on a graphical interface, and
 means to store a menu database having stored menus to control said visual display and present user selectable options, the display of which is dependent on the value of at least one variable characteristic, whereby all available action options are displayed in a menu in said visual display and no unavailable action options, said at least one variable characteristic pertaining to the current status of said active component including whether or not a location is available on the active component to which an additional connectable component might be connected, whereby for any available location said menu database includes information to control said visual display listing all possible actions which can be performed at said location.

5. The expert system of claim 2, wherein said means for recording the geometric relationship between each component of said component pair records vector information associated with each component, said vector information pertaining to the location on each component where it is connected to the other component of the component pair.

6. The expert system of claim 2 further comprising means for storing a plurality of status variables, wherein said means for storing information includes
- means for storing, in said means for storing a plurality of status variables, information about a plurality of variable characteristics including the current linkages, identity and geometric relationships between each component pair in the connected collection and
- means for storing a subset of said status variables in said design database after adding a component to said collection.

7. The expert system of claim 2 wherein said knowledge base further comprises
- a third record pertaining to a third connectable component having a constant characteristic and also a second variable characteristic, the state of which determines whether or not a fourth connectable component can be connected to said third connectable component,
- a fourth record pertaining to said fourth connectable component, connectable to said third component by an allowed connection determined by the state of the second variable characteristic of said third record, and
- a rule for connecting said third connectable component and said fourth connectable component, said rule including a test for said second variable characteristic, and wherein said inference engine further comprises
- means for selecting said third and fourth connectable components to form a second connected collection,
- means for storing information about said second connected collection as a subassembly,
- means for selecting said subassembly and connecting it to said connected collection of said first and said second connectable components to form a modified first connected collection, and
- means for storing information about said modified first connected collection in said design database wherein said design database stores information fully determining each connected collection.

8. The expert system of claim 2 wherein said at least one constant characteristic is selected from the group consisting of a component name, test describing said first component, part number, options available, graphic to draw on screen, parametric graphic values, graphic to use in commercial CAD systems, price, weight, volume, active menu number, manufacturer identification number, price information, availability information, dimension, color and texture.

9. The expert system of claim 2 wherein said information about said connected collection includes information about how said second component is connected to a first component.

10. The expert system of claim 2 wherein said information about said connected collection includes information about wherein said second component is connected to said first component.

11. The expert system of claim 2 wherein said at least one variable characteristic is selected from the group consisting of
- information about the alignment of connection vectors,
- information about a reference coordinate system,
- component number is the connected collection,
- assigned variable name of said first component,
- geometry of a building shell,
- options regarding whether said first component corresponds to a record in a part database,
- a variable stored which records information about the component's logical conditions in relation to said connected collection, and
- information about whether said second component has been selected and, if so, information about said second component and how and where the second component is connected to said first component, 12. The expert system of claim 2 wherein said rule tests for a certain value of said variable characteristic of said first record, 13. The expert system of claim 2 further comprising means for checking said connected collection and identifying a point where an additional component is required to be connected.

14. The expert system of claim 2 further comprising means to draw said connected collection or a selected portion of said connected collection on a computer monitor or printer.

15. The expert system of claim 14 further comprising means to draw on screen with a selected field of view, scale, orientation or perspective.

16. The expert system of claim 2 further comprising means for generating output suitable for use by a CAD program.

17. The expert system of claim 2 further comprising means for generating a list of components included in all of selected portions of the system.

18. An expert system for specifying a physical having at least two attributes, each of which can be described by a corresponding parameter, said expert system comprising
- a knowledge base, said knowledge base comprising:
  - a first record pertaining to a first parameter corresponding to a first attribute of said object, said first record including a variable characteristic, the state of which determines whether or not a second attribute can be combined in said object together with said first attribute,
  - a second record pertaining to a second parameter corresponding to said second attribute of said object, and
  - a rule for combining said first attribute and said second attribute in said object, said rule including a test for the value of said variable characteristic; and
- an inference engine, said inference engine comprising:
  - means for selecting said first record for said first attribute,
  - means for testing said variable characteristic and determining whether said second attribute can be combined with said first attribute in said object,
  - means for selecting said second record for said second attribute; and
  - means for storing information about said object and said selected attributes.

19. A method of designing a connected collection of components where each said component can be described by a least one constant characteristic and at least one variable characteristic, said method comprising
using a computer-based expert system which includes information about a first connectable component and a second connectable component, each capable of being connected to the other determined by the state of a variable characteristic of said first component, a stored value for said variable characteristic of said first component, and a rule for connecting said first and second connectable components, providing a first list of components which can be used to begin designing a connected collection, said first list including said first component, selecting said first component from said first list, testing the value of said variable characteristic of said first component to determine whether said first component can be combined with said second component, and if so providing a second list of components which can be connected to said first component, said second list including said second component, and selecting said second component from said second list to form a connected collection.

20. The method of claim 19 wherein said first component can be connected to said second component at a plurality of locations said method further comprising providing information regarding said plurality of locations, and selecting one said location.

21. The method of claim 20 further comprising storing information sufficient to specify said selected location.

22. The method of claim 19 further comprising checking a collection for completeness, missing parts or unterminated features.

23. The method of claim 19 further comprising outputting data suitable for use by a CAD program.

24. The method of claim 19 further comprising outputting data suitable for use by a AutoCAD.

* * * * *